(12) United States Patent
Fukuoka et al.

(10) Patent No.: US 7,189,576 B2
(45) Date of Patent: *Mar. 13, 2007

(54) METHOD FOR MEASURING SUBSTANCE AND TESTING PIECE

(75) Inventors: Takao Fukuoka, Kyoto (JP); Atsuko Katayama, Kyoto (JP); Kenji Yamamoto, Kyoto (JP); Satoshi Yonehara, Kyoto (JP)

(73) Assignee: Arkray Inc., Kyoto (JP)

(*) Notice: Subject to any disclaimer, the term of this patent is extended or adjusted under 35 U.S.C. 154(b) by 217 days.

This patent is subject to a terminal disclaimer.

(21) Appl. No.: 10/384,757

(22) Filed: Mar. 11, 2003

(65) Prior Publication Data

US 2003/0175985 A1    Sep. 18, 2003

Related U.S. Application Data

(62) Division of application No. 09/068,050, filed as application No. PCT/JP96/03188 on Oct. 30, 1996, now abandoned.

(30) Foreign Application Priority Data

| Oct. 30, 1995 | (JP) | ................................... 7-282146 |
| Oct. 30, 1995 | (JP) | ................................... 7-282147 |
| Oct. 30, 1995 | (JP) | ................................... 7-282148 |
| Sep. 10, 1996 | (JP) | ................................... 8-239510 |
| Sep. 12, 1996 | (JP) | ................................... 8-241677 |
| Sep. 26, 1996 | (JP) | ................................... 8-254944 |
| Oct. 11, 1996 | (JP) | ................................... 8-270354 |
| Oct. 22, 1996 | (JP) | ................................... 8-279661 |

(51) Int. Cl.
*G01N 31/00* (2006.01)

(52) U.S. Cl. ..................... 436/170; 436/184; 436/169; 422/56; 422/57

(58) Field of Classification Search ................ 422/56, 422/57; 436/164, 169, 178
See application file for complete search history.

(56) References Cited

U.S. PATENT DOCUMENTS 3,350,175 A    10/1967   McConnaughey et al.

(Continued)

FOREIGN PATENT DOCUMENTS

EP          0 337 053         10/1989

(Continued)

OTHER PUBLICATIONS

Database WPI, Section Ch, Week 198813, Derwent Publications Ltd., London, GB; AN1988-088337 XP002209949 & JP 63 039599 A, Feb. 20, 1988, Abstract.

(Continued)

*Primary Examiner*—Jill Warden
*Assistant Examiner*—Sam P. Siefke
(74) *Attorney, Agent, or Firm*—Wenderoth, Lind & Ponack, L.L.P.

(57) ABSTRACT

A method of measuring an analyte, comprising a step of measuring a detectable substance by using a reaction system including a formation reaction of the detectable substance based on a chemical reaction of the analyte contained in a sample, wherein a layered inorganic compound is caused to exist in the reaction system including the formation reaction of the detectable substance, whereby high-sensitivity measurement is made possible, the detectable substance can be stabilized to improve accuracy of the measurement, a rate of a chemical reaction is increased to enable quick measurement, and high-sensitivity measurement is made possible even in a reaction system which forms an insoluble substance. Also, it can be provided an analytical testing piece for measuring an analyte, by measuring a detectable substance by using a reaction system including a formation reaction of the detectable substance based on a chemical reaction of the analyte contained in a sample, wherein the testing piece comprises at least one test portion having a detection portion for detecting the detectable substance and contains a layered inorganic compound at least in the test portion, whereby diffusion and elution of a dyestuff or the like is prevented, more sensitive and accurate simple, analysis is made possible, and easy handling is possible.

16 Claims, 17 Drawing Sheets

U.S. PATENT DOCUMENTS

| | | | |
|---|---|---|---|
| 3,672,845 A | 6/1972 | Verbeck | |
| 3,904,373 A | 9/1975 | Harper | |
| 4,015,937 A | 4/1977 | Miyamoto et al. | 23/230 |
| 4,042,335 A | 8/1977 | Clement | 23/253 |
| 4,252,782 A | 2/1981 | Bailey | |
| 4,418,037 A | 11/1983 | Katsuyama et al. | |
| 4,421,719 A | 12/1983 | Burleigh | |
| 4,587,102 A | 5/1986 | Nagatomo et al. | |
| 4,803,162 A | 2/1989 | Smith et al. | 435/36 |
| 5,047,351 A * | 9/1991 | Makiuchi et al. | 436/169 |
| 5,124,128 A | 6/1992 | Hildenbrand et al. | 422/56 |
| 5,240,571 A * | 8/1993 | Heineman et al. | 205/777.5 |
| 5,420,047 A | 5/1995 | Brandt et al. | |

FOREIGN PATENT DOCUMENTS

| | | |
|---|---|---|
| GB | 1 388 531 | 3/1975 |
| GB | 1 519 465 | 7/1975 |
| JP | 57-035753 | 2/1982 |
| JP | 03-015399 | 1/1991 |
| JP | 599 927 | 4/1993 |
| JP | 6 222 061 | 8/1994 |

OTHER PUBLICATIONS

Database WPI, Section Ch, Week 199110, Derwent Publications Ltd., London, GB; AN 1991-068321 XP002209950 & JP 03 015399 A, Jan. 23, 1991, Abstract.

Database WPI, Section Ch, Week 198625, Derwent Publications Ltd., London, GB; AN 1986-159440 XP002209951 & JP 61 092598, May 10, 1986.

* cited by examiner

F I G. 1
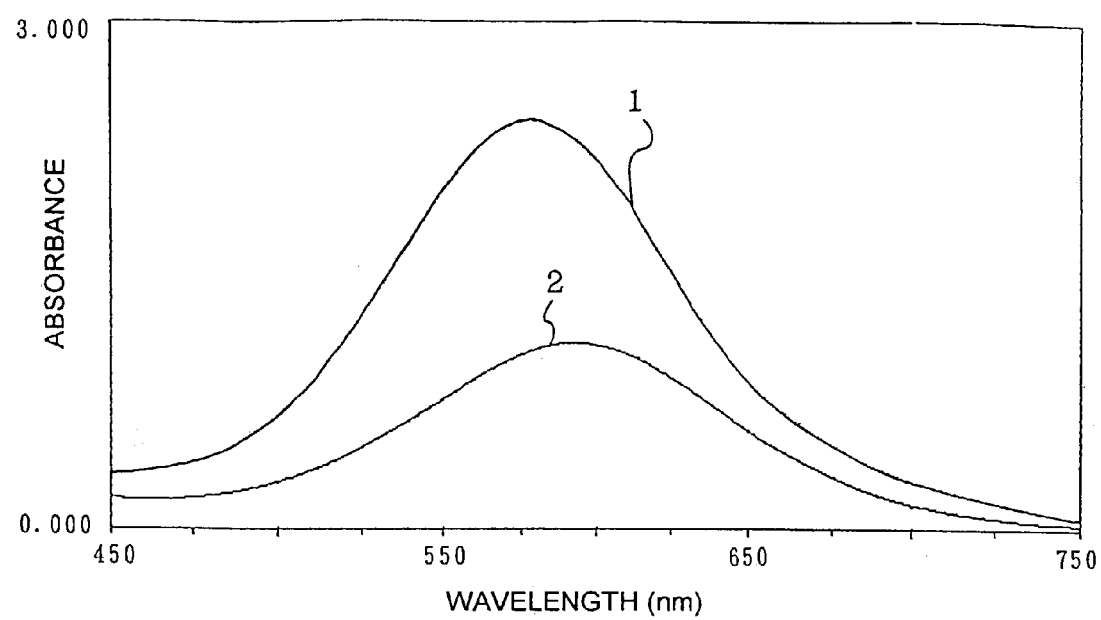

F I G. 1 4
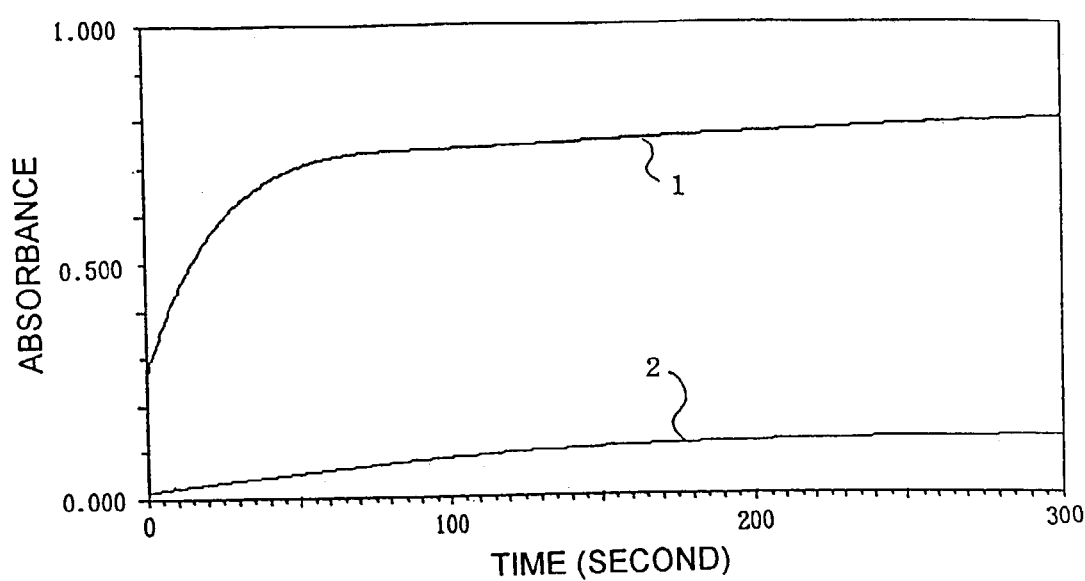

F I G. 21
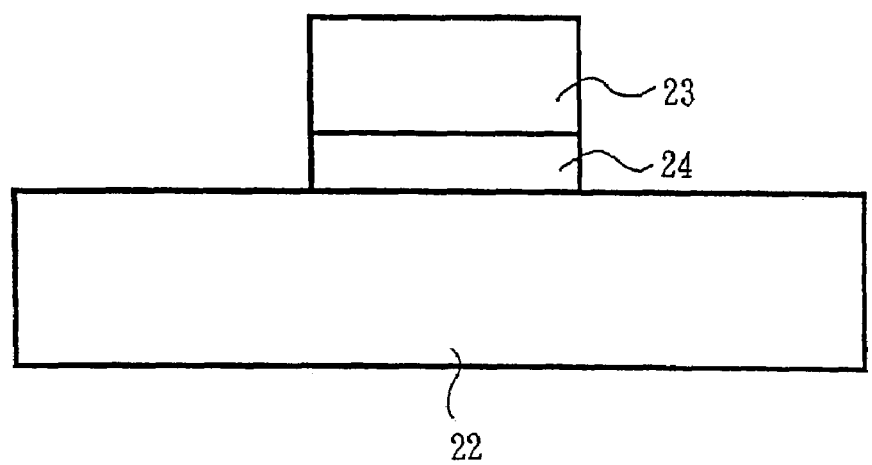

METHOD FOR MEASURING SUBSTANCE AND TESTING PIECE

This application is a divisional of Ser. No. 09/068,050 filed Apr. 29, 1998, now abandoned, which is a U.S. national stage of International Application No. PCT/JP96/03188 filed Oct. 30, 1996.

FIELD OF THE INVENTION

The present invention relates to a method for measuring an analyte such as a biological component or environmental substance by using a reaction system which forms a detectable substance such as a dyestuff based on the chemical reaction of the analyte contained in a sample and measuring the detectable substance, and to a testing piece for use in the method.

BACKGROUND OF THE INVENTION

Methods of detecting and determining an analyte which is contained in a sample, for example, a bio-component in the body fluid such as urine and blood, a trace amount of a substance existent in food, medicine, or natural environment, an industrial chemical substance, a trace amount of a substance contained in waste, or the like include ones for measuring a detectable substance such as a dyestuff formed by a reaction system in which the analyte is involved.

One of the methods is, for example, a method comprising subjecting hydrogen peroxide formed by the chemical reaction of the analyte and a reactive color coupler (dyestuff precursor) to an oxidation-reduction reaction in the presence of peroxidase (POD) and determining the formed dyestuff compound by colorimetry. This method is frequently used in clinical diagnosis and the like because of its simplicity. Another one of the methods is a method of measuring an analyte based on an electrochemical reaction for reducing/oxidizing with an electrode the oxidized/reduced form of an electron carrier (mediator) formed by an oxidation-reduction reaction between the electron carrier and the analyte caused by an enzyme or the like.

However, in the above conventional methods, as measurement sensitivity is not sufficiently high when the amount of the analyte is very small, a highly accurate measurement result cannot be obtained. Therefore, the development of a highly accurate measuring method having improved measurement sensitivity has been desired.

Further, since measurement takes long as a reaction takes time, or it takes time for a detection reaction to reach a termination, a rating method for carrying out quantitative determination from a reaction rate has such a problem that the accuracy of quantitative determination is low. To cope with this, to increase the reaction rate, the reaction system is heated, or the concentration of a reagent for the reaction is increased. However, in the method for heating the reaction system, a heat source is required for heating and analysis is thereby complicated. When the formed substance is thermally instable, detection is difficult and this means cannot be employed. The method for increasing the concentration of the reagent is not practical because it leads to a rise in the background of detection and an increase in the cost of analysis. There is also a method for adding a catalyst to increase the reaction rate. However, since there are many detection reactions for which preferred catalysts are unknown yet, this method is not practical as well. As described above, most of the conventional methods are still unsatisfactory and a novel method which enables quick measurement by increasing the reaction rate more simply has been eagerly desired.

When a reaction which forms a substance insoluble in a reaction solvent is included in the reaction system which forms a detectable substance, there is such inconvenience as enumerated below and called in question.

(1) In measurement in which optical detection is carried out using a liquid reagent, for example, in a batch type automatic biochemical test apparatus, when a dyestuff formed by a reaction is insoluble in a solvent, it separates out and adheres to the wall of a measurement cell to shield incident light or transmitted light or cause the pollution of a dispensing nozzle, and abnormality in absorption coefficient, diffusion or light shielding by agglomeration, thereby making measurement difficult.

(2) Similarly, in measurement in which optical detection is carried out using a liquid reagent, when an insoluble by-product is formed, it adheres to the wall of a measurement cell to shield incident light or transmitted light or cause the pollution of a dispensing nozzle, and diffusion or light shielding by agglomeration, thereby making measurement difficult.

(3) In measurement in which a dyestuff formed by a reaction caused by dropping onto or infiltrating a sample to be measured into a testing piece is optically detected, when the formed dyestuff is insoluble in a sample solvent, the dyestuff deposits on the substrate of the testing piece nonuniformly, or the agglomeration of the dyestuff occurs, thereby deteriorating measurement accuracy.

(4) In electrode measurement using a liquid reagent, for example, in a batch type automatic biochemical test apparatus, when an insoluble by-product is formed, the pollution of an electrode is caused by covering the surface of the electrode with the insoluble deposit, thereby reducing biochemical response and deteriorating measurement accuracy.

The difference between the words "insoluble" and "hardly soluble" indicates a difference in the degree of insolubility in a solvent. In the present invention, the word "insoluble" may be interchanged by "hardly soluble" in the following description.

Particularly, when the formed detectable substance is insoluble in a reaction solvent, reaction rate may be reduced, or measurement sensitivity may be lowered because the reaction system which forms the detectable substance is not uniform and the reaction does not proceed quickly in the prior art method. For example, in the reaction system using an enzyme, the reaction product may deposit near the enzyme or impede the reaction.

Therefore, a measuring method using a reaction which forms a by-product insoluble in a reaction solvent in which the reaction is carried out has rarely been employed. Accordingly, it has been necessary to select a reaction which does not form an insoluble product as a detection system or to develop a new detection reaction system by synthetic chemical means so that the product becomes soluble in a reaction solvent. However, these circumstances have limited a reaction system used. Meanwhile, much time and labor have been required for the research and development of a reaction system which forms only a soluble substance. Further, it has been necessary to add a surfactant for solubilizing, emulsifying or dispersing the product. However, the addition of a surfactant is disadvantageous from the view point of measurement cost and may produce an adverse effect such as interruption of a reaction. Therefore, it cannot be said that it is a perfect solution. Then, a novel method which solves this problem easily and enables measurement in the presence of an insoluble product has been ardently desired.

The method of measuring an analyte using a reaction system which forms hydrogen peroxide as described above is an important measuring method as there are many reactions which form hydrogen peroxide as a substance produced by oxidation. However, accurate measurement has not always been easy in the prior art methods for the following reasons. That is, in these measuring methods, the amount or concentration of a detectable substance such as a dyestuff compound must have a quantitative correlation with a specific substance such as hydrogen peroxide in some cases. However, an oxidation-reduction system in colorimetry is affected by the strong oxidizing activity of excessive hydrogen peroxide or the strong reducing activity of ascorbic acid or the like contained in a biological sample, and the above detectable substance such as a dyestuff compound decomposes, whereby a measurement error may be produced.

For example, in these measuring methods, when an excessive amount of hydrogen peroxide is temporarily formed from an analyte such as glucose by an oxidase such as glucose oxidase, a reaction between the formed dyestuff and hydrogen peroxide occurs in addition to a reaction between a dyestuff precursor and hydrogen peroxide. As a result, the formed dyestuff is decomposed by hydrogen peroxide as soon as it is formed and discolored.

When an enzyme such as peroxidase for producing active oxygen species such as a superoxide having high reactivity from hydrogen peroxide, or transition metal ions and a complex thereof exerting a similar function are existent in a sample, the active oxygen species react with the formed dyestuff, decomposes and discolors it. This interference has affected measurement adversely. When a reaction which forms a detectable substance such as a dyestuff is carried out while it is exposed to the air, the formed dyestuff may be oxidized by oxygen contained in the air or oxygen dissolved in a reaction solution, decomposed and discolored.

Therefore, various attempts have been made such as the research of a dyestuff precursor which provides a stable substance which is hardly decomposed and the addition of various stabilizers but these are still unsatisfactory.

Reducing substances such as ascorbic acid, uric acid and bilirubin contained in a biological sample have a great influence on an oxidation-reduction reaction. Particularly, how to measure an analyte accurately in the presence of ascorbic acid has been a significant theme in the field of clinical analysis for long time. Various interference suppression means such as selective decomposition with an enzyme, decomposition by the addition of periodic acid, oxidation decomposition with iron-ethylene diamine tetraacetate chelate, and selective separation with a semipermeable membrane have been tried in addition to the research of the above-described dyestuff precursor and the like (see Yoshihide Ohta, Yutaka Ogawa, Rinsho Kensa, 34 (4), 502–504 (1990); Japanese Patent Publication No. 1-41223 (1989); Japanese Patent Publication No. 2-4861 (1990); Japanese Patent Publication No. 4-18630 (1992); Japanese Patent Application Laid-open No. 5-95797 (1993); and Japanese Patent Application Laid-open No. 7-155196 (1995)).

There are further methods of measuring a specific analyte by forming a dyestuff (for example, an azo dyestuff) having quantitative relationship with the specific analyte by various known reactions other than the oxidation-reduction reaction (for example, condensation reactions such as an acid-base reaction and the coupling reaction of a diazonium salt, a complex forming reaction and the like) and optically determining the formed dyestuff. These methods are important measuring methods detailed in Bunseki Kagaku Binran (ed. by the Japan Society for Analytical Chemistry), for example. However, some of the thus formed dyestuffs may be an instable compound which is decomposed by oxygen in the atmosphere, an oxidizing or reducing substance contained in a sample, hydrogen ions or bases contained in the sample, light or the like. To measure this substance, for example, quick operation is required, or operation must be carried out in an atmosphere substituted by nitrogen or light shaded environment. Otherwise, an error may be given to measurement.

Methods using an electron carrier (mediator) include one in which an analyte is measured with high sensitivity by carrying out an enzyme reaction for a predetermined time to oxidize/reduce the electron carrier during that time, thereby accumulating the oxidized/reduced form of the electron carrier, and reducing/oxidizing the accumulated oxidized/reduced form of the electron carrier with an electrode after the predetermined time to produce great electrochemical response. Conventionally, the accumulated oxidized/reduced form of the electron carrier has been subjected to a decomposition reaction such as reduction/oxidation by a reducing substance or oxidizing substance which is coexistent with the accumulated oxidized/reduced form of the electron carrier, whereby an error may be given to measurement.

When the detectable substance is stable without being decomposed, the quantitative relationship is ensured at the time of measurement and a more excellent S/B ratio (signal-to-background ratio) can be obtained by carrying out time integration, whereby the accuracy of analysis can be improved and sensitivity can be increased. Therefore, to develop a reaction system which forms a detectable substance which is stable and can be measured easily, many efforts have been made so far. Various reagents which have been developed so far as reaction substances which form such a stable detectable substance are listed in many handbooks, Bunseki Kagaku Binran, for example.

However, the research of a reaction system which forms such a stable substance takes much time and labor, and efforts are still being made to search for a reaction system which forms a detectable substance which is always stable and can be measured easily. Therefore, even in currently used measurement methods, there are many cases where an instable substance which is decomposed by pH, moisture content, coexistent substance such as an oxidizing/reducing substance, light or the like must be measured as the detectable substance.

An analytical testing piece, used to examine and analyze a component contained in a liquid sample such as urine, for measuring an analyte by measuring a detectable substance such as a formed dyestuff based on the chemical reaction of the analyte contained in a sample, generally comprises a test portion which is a functional portion for carrying out a series of analytical processes such as the absorption, diffusion, reaction, detection and the like of the liquid sample and a support portion for supporting the test portion, and further has a sensor, sample solution suction apparatus and the like as required. The above test portion comprises layers or areas for carrying out various functions. Generally speaking, the test portion comprises a sample suction portion for sucking the sample and introducing it thereinto; a diffusion and infiltration portion for diffusing and infiltrating the sample uniformly in the test portion; a reagent portion containing a reagent which reacts with the analyte contained in the sample; a reaction portion where a reaction such as a detection reaction occurs; a developing portion for separating a component contained in the sample, a dyestuff formed by the detection reaction or the like by a chromatography-like function such as adsorption or distribution; a time control portion for adjusting the proceeding of a reaction making use of a time during which the sample moves; a holding portion for trapping or removing a component contained in the sample, formed dyestuff or the like by an adsorption function; a detection portion for detecting a dyestuff or the like by reflectance, transmission/absorption or fluorescence; an absorbing portion for absorbing excess of a sample solution, added washing solution and developing solution to prevent a back flow, and the like.

In an actual testing piece, these portions having the above functions are not always existent independently. For example, like litmus paper in which the detection portion is the same as the sample suction portion, the reagent portion and the reaction portion, there is a case where one portion has multiple functions.

For example, there are single-layered and multi-layered testing pieces which comprise a diffusion layer which also serves as a sample suction layer, a detection layer which also serves as a reagent layer and a reaction layer, or comprise a detection layer independent from a reaction layer which also serves as a reagent layer. Most of them are bonded to a base by an adhesive layer. There is a testing piece which has a developing layer or a holding layer having a function to remove an interfering component between a reaction layer and a detection layer. There is also a testing piece in which a diffusion layer also serves as a developing layer-and is in contact with a reagent layer by an adhesive layer. When detection is carried out by measuring reflectance, a reflection layer may be formed before or after a detection layer. The sample is dropped onto the diffusion layer which also serves as the sample suction layer and diffused uniformly to dissolve a reagent contained in the reagent layer, whereby a reaction proceeds. Thus, for example, a dyestuff is produced from a dyestuff precursor. When the reagent layer and the reaction layer also serve as the detection layer, the dyestuff is directly measured. However, when an independent detection layer is provided, the produced dyestuff or the like further infiltrates and moves into the detection layer and is measured at that point (see H. G. Curme, et al., Clinical Chemistry, 24 (8), 1335–1342 (1978); B. Walter, Analytical Chemistry, 55 (4), 498A (1983); Asaji Kondo, Bunseki, 1984 (7), 534; Asaji Kondo, Bunseki, 1986 (6), 387; Bunseki Kagaku Binran, p. 8 (edited by the Japan Society for Analytical Chemistry: fourth revised edition, Maruzen (1991); and Japanese Patent Application Laid-open No. 6-213886 (1994) (Masao Kitajima et al.)).

There is also a testing piece which comprises an infiltration portion of a developing solution at an end of the testing piece on a small piece of filter paper; a sample suction portion adjacent to the infiltration portion; a reaction portion which also serves as a reagent portion (having-an enzyme immobilized thereto) near the center of the testing piece; and a detection portion which also serves as a reagent portion (having a dyestuff precursor or the like immobilized thereto), a reaction portion and a holding portion after the reaction portion and makes use of the plane movement of the sample or the like. In this case, after the sample is dropped onto the sample suction portion, the developing solution is infiltrated from the end of the testing piece to move the sample by a capillary action, the sample reacts with the enzyme in the reaction portion which also serves as the first reagent portion (having the enzyme immobilized thereto) to produce hydrogen peroxide which is then moved by the developing solution to color the dyestuff precursor or the like in the detection portion which also serves as the second reagent portion (having the dyestuff precursor or the like immobilized thereto), the reaction portion and the holding portion, and adsorb and hold the produced dyestuff or the like (detectable substance). Since the hydrogen peroxide moves along with the movement of the developing solution and a coloration reaction occurs along with the movement, when the amount of the analyte increases, the length of coloration expands, whereby the substance can be measured. (see M. P. Allen, et al., Clinical Chemistry, 36 (9), 1591–1597 (1990); D. Noble, Analytical Chemistry, 65 (23), 1037A (1993).)

This testing piece is used in a urine test, a biochemical test, an immunochromatography test and the like. In an example of a testing piece for immunochromatography, when one end of filter paper having an antibody immobilized thereto (it can be said that the entire surface thereof serves as a reagent portion, a reaction portion, a developing portion, a holding portion and a detection portion) is immersed in a developing solution prepared by mixing a sample containing an antigen (analyte) and an enzyme-linked antigen as a reagent to develop with a color developing solution which is a second reagent (containing a dyestuff precursor), a portion containing the enzyme-linked antigen which has been developed and captured is colored like a belt. The length of the colored belt is proportional to the amount of the antigen contained in the sample. (see R. F. Zuk, et al., Clinical Chemistry, 31 (7), 1144–1150 (1985).)

As another example of a testing piece for immunochromatography, there is a testing piece which comprises a reagent portion (first antibody immobilized colored latex) which also serves as a sample suction portion at one end on a small piece of a membrane filter, a reagent portion (second antibody which recognizes the same antigen as that of the first antibody but is different in epitope) which also serves as a developing portion near the center, a developing portion and further a detection portion which also serves as a reagent portion (anti-first antibody antibody) and a holding portion. When a sample is dropped onto the sample suction portion, an antigen-antibody reaction between an antigen (analyte) and the first antibody occurs, an immuno-complex directly moves along with the movement of the sample, and a sandwich reaction between the immuno-complex and the second antibody occurs in the reagent portion which also serves as a developing portion. However, excess of the first antibody which does not form an immuno-complex passes through the developing portion along with the movement of the sample and is captured in the detection portion which also serves as the reagent portion, (anti-first antibody antibody) and the holding portion. The analyte can be measured by measuring the coloration of the colored latex (containing a dyestuff as a detectable substance) to which the first antibody is immobilized. (see I. W. Davidson, Analytical Proceedings, 29, 459 (1992).)

However, in the above testing pieces, a dyestuff or the like produced by a reaction with a component to be analyzed has solubility in a sample solution, reaction solution or the like in many cases with the result of such inconvenience as the elution of the dyestuff or the like into a bulk solution, a back flush to the diffusion layer, and the adhesion of the dyestuff or the like to the adjacent test portion in multi-item test paper having a plurality of test portions. Due to the movement of the dyestuff or the like toward the edge of the test portion by drying, there occurs such a phenomenon that the concentration of a center portion becomes low and that of a peripheral portion becomes high.

Such an inconvenient phenomenon that deteriorates measurement sensitivity, precision and accuracy is particularly marked in urine test paper or the like which is immersed in a sample solution for measurement but is very common irrespective of the type of sample.

Meanwhile, there have been proposed a method for preventing the elution of a reagent by covering a test portion (Japanese Patent Application Laid-open No. 2-38861 (1990)), a method for preventing liquid junction between adjacent test portions by causing the test portions composed of a porous structure (such as a porous layer or a porous film) having high absorptivity to uniformly absorb a sample (Japanese Patent Application Laid-open No. 2-6541 (1990)), a method for selecting a reaction for forming an insoluble dyestuff, a method for capturing a formed dyestuff using an insoluble and hydrophobic binder (fixing agent) (Japanese Patent Application Laid-open No. 7-181174 (1995)), a method for increasing the distance between adjacent test portions in the multi-item test paper, a method for controlling and adjusting immersion time, a method for controlling time so that measurement is carried out before diffusion, and the like. However, covering a test portion or preparing a porous structure by a precipitation-solidification method makes a test paper production process complicated. When a reaction for forming an insoluble dyestuff is selected, a product inhibition of enzyme activity occurs. A testing piece prepared by using a hydrophobic polymer as a binder has such a defect that the absorptivity of an aqueous sample solution deteriorates. A multi-item testing piece has such a defect that when the distance between adjacent test portions is increased, a larger area is required or it is disadvantageous for the movement of the sensor as a single sensor moves through a plurality of test portions to measure reflected light. The other methods have respective problems to be solved. For example, the method for controlling immersion time is troublesome in an urine test, the method for controlling time is not easy because of the relationship between control time and reaction time. Satisfactory solutions to these problems are yet to be found.

A method for measuring an analyte from electrochemical response at the time of oxidation-reduction using the above electron carrier (mediator), a method for measuring ions as an analyte by measuring the potential of a membrane upon the movement of a complex compound formed by using a ligand (ionophore) which is coordinately bonded or ion bonded to a specific ion in a liquid film electrode, and the like are known as important measuring methods. Generally speaking, in an electrode composed of an oxidized/reduced form of an electron carrier or a complex compound, the elution or diffusion of the electron carrier or ligand is prevented by adding the electron carrier or ligand to an insoluble polymer, and the electron carrier or ligand is held near the surface of the electrode so that electrons can move quickly at the same time. Since the movement of a substance in a polymer is limited, a reaction between an analyte contained in the sample or an intermediate substance produced from the analyte and the electron carrier or ligand contained in the insoluble polymer is interrupted. A satisfactory solution to this fundamental problem is yet to be found as well.

DISCLOSURE OF THE INVENTION

It is an object of the present invention to provide a high-sensitivity measuring method for measuring an analyte by measuring a detectable substance such as a dyestuff or the like formed based on the chemical reaction of the analyte. The term "measurement" comprehends both quantitative and qualitative measurements.

It is another object of the present invention to provide a method which can improve measurement accuracy and increase measurement sensitivity by stabilizing the detectable substance in the above method for measuring the analyte.

It is still another object of the present invention to provide a novel method which enables quick measurement by increasing the reaction rate of a chemical reaction in the above measuring method.

It is a further object of the present invention to provide a high-sensitivity measuring method in the above method using a reaction system including the formation reaction of an insoluble substance.

It is a still further object of the present invention to provide an analytical testing piece which can suppress the diffusion and elution of a dyestuff or the like, enables accurate examination and analysis, and is easy to use.

The inventors of the present invention have found that the above problems can be solved by carrying the formation reaction of a detectable substance in the presence of a layered inorganic compound and by allowing a layered inorganic compound to be contained in a test portion, such as a detection portion for detecting a detectable substance, of a testing piece. The present invention has been accomplished based on the above finding.

Thus, the present invention provides a method for measuring an analyte, comprising a step of measuring a detectable substance by using a reaction system including a formation reaction of a detectable substance based on a chemical reaction of the analyte contained in a sample, wherein a layered inorganic compound is caused to exist in the reaction system including the formation reaction of the detectable substance. This method will be referred to as "measuring method of the present invention" hereinafter.

The present invention also provides the above-mentioned method for measuring the substance comprising a step of adding the layered inorganic compound to the reaction system to allow the layered inorganic compound to adsorb the detectable substance. This method will be referred to as "first method of the present invention" hereinafter.

In the first method of the present invention, high-sensitivity measurement is made possible by allowing the layered inorganic compound to adsorb the formed detectable substance. That is, for example, the detectable substance is adsorbed to the layered inorganic compound and settles, whereby measurement sensitivity in optical or electrochemical detection is improved. In this case, the detectable substance may be adsorbed to the layered inorganic compound and settle as a colloidal agglomerate. However, it does not always need to be agglomerated.

The present invention also provides the method for measuring the analyte, wherein the layered inorganic compound is caused to exist in the reaction system to suppress the decomposition of the detectable substance. This method will be referred to as "second method of the present invention" hereinafter.

In the second method of the present invention, by causing the layered inorganic compound to exist in the reaction system which forms the detectable substance to be measured, a complex between the detectable substance and the layered inorganic compound is formed almost at the same time when the detectable substance is formed or before it is decomposed by a coexistent substance with the result that the decomposition of the detectable substance by the function of the coexistent substance in the reaction system can be suppressed.

The present invention further provides the method for measuring the analyte, wherein the formation reaction of the detectable substance is carried out in the presence of the layered inorganic compound to increase a reaction rate of the formation reaction. This method will be referred to as "third method of the present invention" hereinafter.

In the third method of the present invention, by carrying out the formation reaction of the detectable substance in the presence of the layered inorganic compound, the reaction rate of the formation reaction is increased and quick measurement is made possible, thereby greatly shortening measurement time and also a time required for the detection reaction to reach a termination with the result that the determination accuracy of a rating method for quantity determination from a reaction rate can be improved. The reason for an increase in the rate of the formation reaction of the detectable substance is not always clear but it is considered that the reaction rate is increased by the adsorption of a reaction starting substance or a reaction intermediate of the formation reaction to the surface of the layered inorganic compound and the concentration thereof on the surface.

The present invention further provides the method for measuring the analyte wherein at least one of reactions constituting the reaction system is the formation reaction of a substance insoluble in a reaction solvent. This method will be referred to as "fourth method of the present invention" hereinafter.

In the fourth method of the present invention, it is possible to make a reaction proceed quickly like a uniform system by causing a layered inorganic compound to exist in the reaction system including the formation reaction of the detectable substance preferably in a dispersed state even when the detectable substance or a by-product of the reaction is insoluble in a reaction solvent. It is considered that this is because the formed insoluble detectable substance or the insoluble by-product is adsorbed to the layered inorganic compound and uniformly dispersed in the reaction system together with the layered inorganic compound. In the present invention, the detectable substance or the by-product can be prevented from separating out into the reaction system and becoming difficult to be handled at the time of detection by allowing the detectable substance or the by-product insoluble in a solvent to be adsorbed by the layered inorganic compound.

Cases where the detectable substance or the by-product are prevented from becoming difficult to be handled at the time of detection may be as follows.

(1) In measurement in which optical detection is carried out using a liquid reagent, for example, in a batch type automatic biochemical test apparatus, when a dyestuff formed by a reaction is insoluble in a solvent, by allowing the dyestuff to be adsorbed by the layered inorganic compound, it is possible to prevent the dyestuff from separating out and adhering to the wall of a measurement cell to shield incident light or transmitted light and cause the pollution of a dispensing nozzle and abnormality in absorption coefficient, scattering or light shielding. Thus, it is possible to prevent measurement from becoming difficult.

(2) Similarly, in measurement in which optical detection is carried out using a liquid reagent, when an insoluble by-product is formed, by allowing the by-product to be adsorbed by the layered inorganic compound, it is possible to prevent the by-product from adhering to the wall of a measurement cell to shield incident light or transmitted light and cause the pollution of a dispensing nozzle and scattering or light shielding by agglomeration. Thus, it is possible to prevent measurement from becoming difficult.

(3) In measurement in which a reaction is carried out by dropping onto or infiltrating a sample to be measured into a testing piece and the formed dyestuff is optically detected, when the formed dyestuff is insoluble in a sample solvent, by allowing the dyestuff to be adsorbed by the layered inorganic compound, it is possible to prevent the dyestuff from nonuniformly depositing on the reaction portion or the detection portion of the testing piece and from being agglomerated, thereby eliminating deterioration in measurement accuracy.

(4) In electrode measurement using a liquid reagent, for example, in a batch type automatic biochemical test apparatus, when an insoluble by-product is formed, by allowing the by-product to be adsorbed by the layered inorganic compound, it is possible to prevent the insoluble deposit from covering the surface of the electrode to cause the pollution of the electrode and lower electrochemical response, thereby eliminating deterioration in measurement accuracy.

A measuring method which the present invention is applied to is not particularly limited if it is a method for measuring an analyte by measuring a detectable substance by using a reaction system including the formation reaction of the detectable substance based on the chemical reaction of the analyte contained in a sample. The detectable substance may be the analyte as a matter of course. Further, the method may be a method for measuring an analyte qualitatively by measuring a detectable substance or a method for measuring an analyte quantitatively by using a reaction system including the formation reaction of a detectable substance having a quantitative correlation with the analyte. Moreover, not only a case where a reaction system which forms a detectable substance directly by the chemical reaction of an analyte is used but also a case where the chemical reaction of the analyte and the formation reaction of the detectable substance are indirectly connected to each other through another chemical reaction are included. Out of these methods, the method of the present invention is preferably applied to a measuring method using a reaction system in which the detectable substance is a dyestuff or electron carrier formed by an oxidation-reduction reaction, a measuring method using a reaction system in which the formed detectable substance is a dyestuff such as an azo dyestuff or a complex between an ionophore and an analyte, and the like.

Particularly, a method of optically measuring a dyestuff formed quantitatively by an oxidation-reduction reaction between hydrogen peroxide formed from a biological component by an oxidizing enzyme reaction and a reactive color-producing reagent is used in the quantitative determination of each component contained in the body fluid in clinical examination, environmental analysis and the like. By applying the measuring method of the present invention in these analytical and detection methods, highly sensitive measurement is made possible.

Speaking of the second method of the present invention in particular, in an oxidation-reduction reaction system, for example, an oxidizing substance, a reducing substance or a peroxidase-like substance often exists in the reaction system as a reaction intermediate or an impurity in a sample, and a detectable substance may be decomposed by the function of these existent substances in the reaction system. In this case, the second method of the present invention is useful.

According to the second method of the present invention, in the above measuring method using an oxidation-reduction reaction between hydrogen peroxide and a reactive color-producing reagent, such a problem that a measurement error is made by the decomposition and discoloration of a dyestuff or the like caused by the function of an oxidizing substance such as excessive hydrogen peroxide or a reducing substance such as ascorbic acid, uric acid and bilirubic acid existent in the reaction system can be overcome.

The third method of the present invention makes it possible to adsorb a reaction starting substance or a reaction intermediate to the surface of a layered inorganic compound by adding the layered inorganic compound having cationic exchange ability to a reaction system particularly when the starting substance or the intermediate of the formation reaction of a detectable substance is a cationic compound, whereby the formation reaction rate can be improved and quick measurement is made possible. Therefore, the third method of the present invention is useful for a measuring method using the above reaction system.

The fourth method of the present invention is not particularly limited if it is a method using a reaction system including the formation reaction of a detectable substance insoluble in a reaction solvent or an insoluble by-product.

The measuring method of the present invention is used in a method of detecting and determining an analyte, preferably a biological component in the body fluid such as urine and blood, a trace amount of a substance existent in food, medicine, or natural environment, an industrial chemical substance, or a trace amount of a substance contained in waste, from a sample containing the same.

The present invention provides a analytical testing piece for measuring an analyte by measuring a detectable substance by using a reaction system including a formation reaction of the detectable substance based on a chemical reaction of the analyte contained in a sample, wherein the testing piece comprises at least one test portion having a detection portion for detecting the detectable substance and contains a layered inorganic compound at least in the test portion. The testing piece will be referred to as "testing piece of the present invention" hereinafter.

The testing piece of the present invention may comprise at least one test portion composed of two or more layers including a detection layer for detecting a detectable substance as the detection portion and contain the layered inorganic compound at least in the detection layer. The testing piece of the present invention may be one in which the test portion further include a diffusion layer for diffusing a sample so that the sample passes through the diffusion layer to be diffused and reaches the detection layer. The testing piece of the present invention may comprise at least one test portion having a detection area for detecting the detectable substance as the detection portion and contain the layered inorganic compound at least in the detection area. The testing piece of the present invention may be one in which the test portion has a diffusion area for diffusing the sample so that the sample passes through the diffusion area to be diffused and reaches the detection area. Further, the testing piece of the present invention may be one in which the detection area composed of at least two layers including a detection layer for detecting the detectable substance. Moreover, the testing piece of the present invention may be one in which the test portion has a reaction portion where the analyte contained in the sample reacts with a reagent react, and the detectable substance is formed in the reaction portion. Further, the testing piece of the present invention may be one in which the detection portion is provided at a location which the sample reaches after the sample is diffused and passes through the reaction portion. Still further, the testing piece of the present invention may be one in which the detectable substance is formed by a reaction between the analyte contained in the sample and a reagent in the detection portion.

In the testing piece of the present invention, it is considered that a dyestuff or the like formed by a reaction between an analyte and a reagent is adsorbed to a layered inorganic compound by including the layered inorganic compound in the test portion with the result that the diffusion or elution of the dyestuff or the like by a sample solution or a reaction solution can be suppressed, and highly sensitive and highly accurate analysis is made possible.

The testing piece of the present invention is applied to a method for analyzing a component contained in a liquid using a solid phase, particularly analysis of glucose, bilirubin or the like contained in urine. In the analysis of the component contained in the liquid, a dyestuff or the like formed by a reaction between an analyte and a reagent may readily dissolve in a sample, diffuse and elute. Therefore, the testing piece of the present invention is effective.

The reagent is not particularly limited if it causes a detectable reaction with an analyte. It is preferably a reagent capable of forming a detectable substance such as a dyestuff compound, an oxidized/reduced form of an electron carrier or a complex compound of an ionophore and an ion by reacting with the analyte. The formation reaction of a dyestuff compound may be any reaction if it forms an optical detectable substance. It may be a reaction which causes not only color development but also color change, fluorescence and emission. When the formed dyestuff compound or the like is water-soluble, it is often diffused and eluted by a sample solution, a reaction solution or the like. Therefore, the testing piece of the present invention is particularly preferably applied to a method using a reagent for forming such a water-soluble dyestuff compound.

BRIEF DESCRIPTION OF THE DRAWINGS

FIG. 1 shows absorption spectra measured in Example 1.

FIG. 14 shows time-cource of absorbance measured in Example 11.

FIG. 21 schematically shows a testing piece in Example 16.

Figure 2:
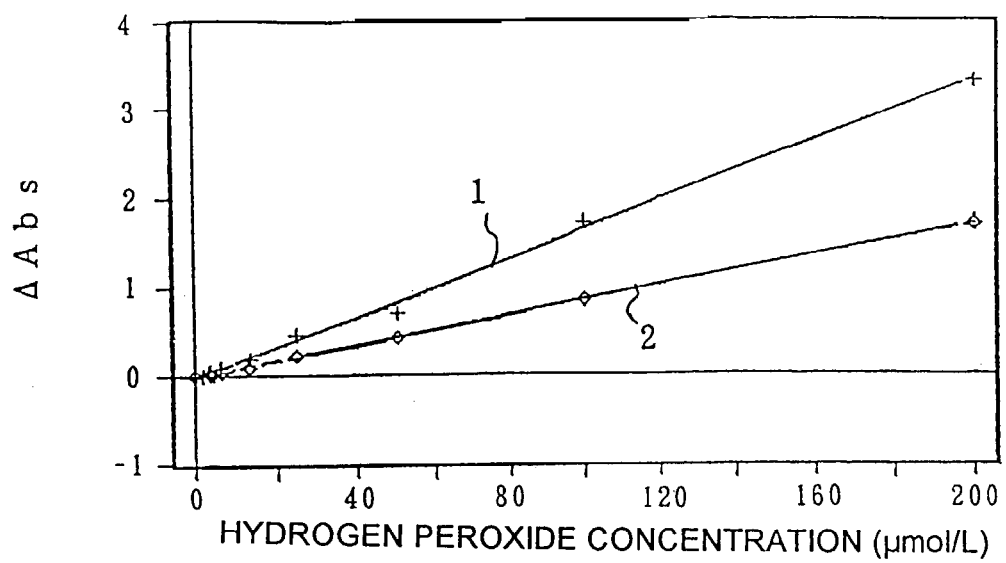
FIG. 2 shows the calibration curves of hydrogen peroxide obtained in Examples 2 and 3.

In these figures, reference numeral 1 is a case where smectite is added, 2 is a case where smectite is not added and 3 is a case where smectite is added and hydrogen peroxide is not added. 4 is a case where the concentration of nitrous acid is 33 μmol/l, 5 is a case where the concentration of nitrous acid is 16 μmol/l, 6 is a case where the concentration of nitrous acid is 8 μmol/l, and 7 is a case where the concentration of nitrous acid is 0 μmol/l. 8 is sample No. 1, 9 is sample No. 2, 10 is sample No. 3, 11 is sample No. 4, and 12 is sample No. 5. 13 is a case where the concentration of sodium nitrite is 50.0 μmol/l, 14 is a case where the concentration of sodium nitrite is 25.0 μmol/l, 15 is a case where the concentration of sodium nitrite is 12.5 μmol/l, 16 is a case where the concentration of sodium nitrite is 6.3 μmol/l, and 17 is a case where the concentration of sodium nitrite is 1.6 μmol/l. 18 is a spot of a dyestuff, 19 is a color developing solution from which a dyestuff is removed, 20 is glass, 21 is a coating film, and 22 is PET. 23 is filter paper impregnated with a reagent (detection layer), 24 is adhesive double-coated tape (adhesive layer), 25 is filter paper impregnated with a dispersion of a layered inorganic compound, 26 is filter paper impregnated with a reagent and 27 is filter paper. 28 is a sample suction area, 29 is a diffusion area, 30 is a reaction area, 31 is an area for controlling reaction time, 32 is a holding area and 33 is an area for absorbing excess of a sample.

BEST MODE FOR CARRYING OUT THE INVENTION

I. Measuring Method of the Present Invention

The measuring method of the present invention is a method for measuring an analyte by measuring a detectable substance by using a reaction system including the formation reaction of the detectable substance based on the chemical reaction of the analyte contained in a sample.

1. Detectable Substance

The reaction system used in the present invention includes the formation reaction of the detectable substance as shown below.

The detectable substance is not particularly limited if it can be adsorbed by the layered inorganic compound according to the present invention. Examples of the detectable substance which can be adsorbed by the layered inorganic compound include amines such as amine and polyamine; imines such as imine and polyimine; polyenes; aromatic compounds such as aniline derivatives, benzoquinone derivatives and aromatic condensed ring compounds; heterocyclic compounds such as xantene, azine and thiazine; complexes between ions and cyclic ligands such as crown ether and valinomycin; and the like. These substances may contain a quaternary nitrogen atom, phenolic hydroxyl group, sulfonic acid group or carboxyl group in the molecule.

The substance which can be adsorbed by the layered inorganic compound is detailed in, for example, Chapter XI "Interaction of Clays and Organic Compounds" of "An Introduction to Clay Colloid Chemistry, Second Edition" written by H. Van Olphen (Krieger Publishment, Malabar). Japanese Patent Publication No. 50-8462 (1975) (Tadayoshi Kato) introduces many adsorbable compounds. They include substances which can be detected by an optical method and an electrochemical method.

(1) Substances which can be Detected by an Optical Method

Substances which can be detected by an optical method include dyestuffs. The dyestuffs include fluorescent dyestuffs, luminescent substances and the like. The formation reaction of the dyestuff may be the formation reaction of an optically detectable substance, for example, a reaction causing color development, color change, fluorescence, light emission or the like.

Preferred dyestuffs include dyestuff compounds, fluorescent substances and luminescent substances formed from dyestuff precursors by various coloration reactions such as an oxidation-reduction reaction, an acid-base reaction and a condensation reaction, dyestuff complexes and fluorescent complexes formed by coordinate bonding or ion bonding, and the like.

Preferred dyestuffs formed by an oxidation-reduction reaction are compounds having a conjugate system such as an aromatic ring, such as dyestuffs formed by the oxidation condensation of a coupler such as 4-amino-1,2-dihydro-1, 5-dimethyl-2-phenyl-3H-pyrazol-3-one(4-aminoantipyrin: to be abbreviated as 4-AA hereinafter) and a hydrogen donor (Trinder's reagent such as N-ethyl-N-(3-sulfopropyl)-3,5-dimethylaniline); color-producing dyestuffs by oxidation such as o-tolidine and benzidines (such as 3,3',5,5'-tetramethyl-benzidine); dyestuffs formed by the oxidation of leuco substances such as 2,6-dichloro-4-[(4-hydroxyphenyl) imino]-2,5-cyclohexadien-1-one; fluorescent substances formed by the oxidation of 4-hydroxyphenyl acetate; luminescent substances such as chemiluminescent substances and exciting substances thereof; formazans which are reducing dyestuffs of tetrazolium salts; dyestuffs formed by the reduction of 1,1'-dimethyl-4,4'-bipyridinium salts and the like; and the like.

The hydrogen donor is a compound such as phenol which forms a quinone dyestuff when it is condensed with 4-amino-1,2-dihydro-1,5-dimethyl-2-phenyl-3H-pyrazol-3-one(4-AA) or 3-methyl-2-benzothiazoline hydrazone by the function of peroxidase in the presence of hydrogen peroxide. Examples of the hydrogen donor include dichlorophenol, o-methoxyphenol, 1,2,3-trihydroxybenzene, dimethylaniline, N-ethyl-N-sulfopropyl-m-anisidine, N-ethyl-N-sulfopropylaniline, N-ethyl-N-(3-sulfopropyl)-3,5-dimethoxyaniline, N-ethyl-N-(3-sulfopropyl)-3,5-dimethylaniline, N-ethyl-N-sulfopropyl-m-toluidine, N-ethyl-N-(2-hydroxy-3-sulfopropyl)-m-anisidine, N-ethyl-N-(2-hydroxy-3-sulfopropyl)aniline, N-ethyl-N-(2-hydroxy-3-sulfopropyl)-3,5-dimethoxyaniline, N-(2-hydroxy-3-sulfopropyl)-3,5-dimethoxyaniline, N-ethyl-N-(2-hydroxy-3-sulfopropyl)-3,5-dimethylaniline, N-ethyl-N-(2-hydroxy-3-sulfopropyl)-m-toluidine, N-(3-sulfopropyl) aniline and the like.

In a method using a reaction system which forms a quinone dyestuff by a reaction between the above 4-AA and a hydrogen donor in the presence of hydrogen peroxide, an analyte is measured by measuring hydrogen peroxide indirectly by measuring the formed quinone dyestuff with an absorptiometer.

o-Tolidine and benzidines include o-tolidine, dianisidine, 3,3'-diaminobenzidine, 3,3',5,5'-tetra-methylbenzidine, N-(3-sulfopropyl)-3,3',5,5'-tetra-methylbenzidine and the like.

The leuco substance is an achromatic dyestuff precursor which becomes a dyestuff and develops color when it is oxidized. Examples of the dyestuff obtained by oxidizing the leuco substance include 2,6-dichloro-4-[(4-hydroxyphenyl) imino]-2,5-cyclohexadien-1-one, 2,6-dichloro-4-[(3-chloro-4-hydroxyphenyl)imino]-2,5-cyclo-hexadien-1-one, 7-(diethylamino)-3-imino-8-methyl-3H-phenoxazine salt, 3-(diethylamino)-7-amino-5-phenylphenazinium salt, 3,7-bis(dimethylamino)-phenothiazin-5-ium salt, 1-hydroxy-5-methylphenazinium salt, and 7-hydroxy-3H-phenoxazin-3-one-10-oxide. Examples of the leuco substance include 4,4'-benzylidenebis(N,N-dimethylaniline), 4,4'-bis[N-ethyl-N-(3-sulfopropylamino)-2,6-dimethylphenyl]methane, 1-(ethylaminothiocarbonyl)-2-(3,5-dimethoxy-4-hydroxyphenyl)-4,5-bis(4-diethylaminophenyl)imidazole, 4,4'-bis (dimethylamino)diphenylamine, N-(carboxymethylaminocarbonyl)-4,4'-bis(dimethylamino)-diphenylamine salt, 10-(carboxymethylaminocarbonyl)-3,7-bis(dimethylamino) phenothiazine salt and the like.

Other examples of the dyestuff precursor which develops color when it is oxidized include 4-methoxyphenol, 4-ethoxyphenol, 2-ethoxyphenol, 1-(2-hydroxy-5-methoxyphenyl) ethanone, 2-hydroxy-5-methoxybenzoic acid, 2-hydroxy-5-methoxybenzaldehyde, 2-hydroxy-5-methoxymethylbenzoic acid, 4-methoxy-2-nitrophenol, 2-chloro-4-methoxyphenol, 4-hydroxy-3-methoxybenzaldehyde, 4-hydroxy-3-methoxybenzoic acid and the like.

3-(4-Hydroxyphenyl)-2-propenoic acid, 2-hydroxyphenylacetic acid, 3-hydroxyphenylacetic acid, 4-hydroxyphenylacetic acid, 3-hydroxybenzoic acid, 4-hydroxybenzoic acid, 2-aminobenzoic acid, 3-aminobenzoic acid, 4-aminobenzoic acid, 3,4-diaminobenzoic acid, 3,5-diaminobenzoic acid, 4-amino-2-chlorobenzoic acid, 4-amino-3-methylbenzoic acid, 4-amino-3-methoxybenzoic acid, 4-aminophthalic acid and the like are further included in the above examples.

2,4-Diamino-6-hydroxypyrimidine, 4,5-diamino-6-hydroxypyrimidine, 4-amino-2,6-dihydroxypyrimidine, 6-hydroxy-2,4,5-triaminopyrimidine, 4,5-diamino-2,6-dihydroxypyrimidine, 4-amino-6-hydroxy-2-methylpyrimidine, 4-amino-6-hydroxypyrimidine, 4-amino-6-hydroxy-2-methoxypyrimidine and the like are also included.

Fluorescent substances may be formed by oxidizing 4-hydroxyphenylacetic acid and the like. Examples thereof include fluorescent substances formed by oxidizing 4-hydroxyphenylacetic acid, (4-hydroxy-3-methoxyphenyl)acetic acid, 3-(4-hydroxyphenyl)propionic acid, 4-hydroxy-(2-aminoethyl)-phenol, 4-hydroxy-N,N,N-trimethylbenzenemetaminium, α-amino-p-hydroxyhydrocinnamic acid, 4-hydroxyphenethylamine, N-(4-hydroxyphenyl)acetoanilide, 2,7-dichlorofluorescein diacetate and the like.

Luminescent substances such as chemiluminescent substances include firefly luciferin, Cypridina luciferin, aequorin, lucigenin derivatives, luminol derivatives, acridinium esters, peroxalic acid esters and the like.

For example, in the above method using a reaction system in which the benzidine or leuco substance is oxidized in the presence of hydrogen peroxide and develops color, an analyte is measured by measuring hydrogen peroxide indirectly by measuring the formed dyestuff with an absorptiometer.

In the above method using a reaction system in which a fluorescent substance or a luminescent substance is formed, an analyte is measured by measuring hydrogen peroxide indirectly with a fluorophotometer or a luminophotometer.

In the oxidation reaction which forms a dyestuff, an oxidizing agent used for the oxidation reaction is not limited to hydrogen peroxide but various known oxidizing agents may be used. An oxidizing enzyme such as peroxidase may be added. Prior to the oxidation reaction which forms a dyestuff, a reaction for forming the oxidizing agent may take place.

The tetrazolium salts include 2,3,5-triphenyl-tetrazolium salt, 2,5-diphenyl-3-(1-naphthyl)-2H-tetrazolium salt, 3,3'-(3,3'-dimethoxy-4,4'-biphenylene)-bis[2-(p-nitrophenyl)-5-phenyl-2H-tetrazolium]salt, 3,3'-[3,3'-dimethoxy-(1,1'-biphenyl)-4,4'-diyl]-bis(2,5-diphenyl-2H-tetrazolium)salt, 2-(4-iodophenyl)-3-(4-nitrophenyl)-5-phenyl-2H-tetrazolium salt, 2-(4-iodophenyl)-3-(4-nitrophenyl)-5-(2,4-disulfophenyl)-2H-tetrazolium salt, 2-(4-iodophenyl)-3-(2,4-dinitrophenyl)-5-(2,4-disulfophenyl)-2H-tetrazolium salt, 3,3'-(1,1'-biphenyl-4,4'-diyl)-bis(2,5-diphenyl-2H-tetrazolium)salt, 3-(4,5-dimethyl-2-thiazolyl)-2,5-diphenyl-2H-tetrazolium salt and the like.

The dyestuffs formed by reduction include reduced forms of 1,1'-dimethyl-4,4'-bipyridinium salt, 1,1'-dibenzyl-4,4'-bipyridinium salt and the like. Fluorescent substances may be formed by reducing 7-hydroxy-3H-phenoxazin-3-one-10-oxide and the like. Examples thereof include fluorescent substances formed by reducing 7-hydroxy-3H-phenoxazin-3-one-10-oxide, 5-cyano-2,3-bis(4-methylphenyl)-2H-tetrazol salt, 2,3-bis(4-cyanophenyl)-5-cyano-2H-tetrazolium salt and the like.

For example, in the above method using a reaction system in which the tetrazolium salt or the leuco substance is reduced in the presence of a reducing agent and develops color, an analyte is measured by measuring the reducing agent indirectly by measuring the formed dyestuff with a colorimenter or fluorophotometer. Prior to the reduction reaction which forms a dyestuff, a reaction for forming a reducing agent may take place.

In the above reduction reaction which forms a dyestuff, nicotinamide adenine dinucleotide or nicotineamide adenine dinucleotide phosphate is preferably used as the reducing agent used for the reduction reaction. However, the present invention is not limited to this but various known reducing agents may be used.

Dyestuffs formed by an acid-base reaction include compounds which develop color or change their colors by pH variations, such as Bromocresol Green. The compounds include sulfone phthalein dyestuffs such as Bromophenol Blue, Phenol Red, Bromopyrogallol Red and Pyrogallol Red; triphenylmethane dyestuffs such as Malachite Green and rosolic acid; quinoline dyestuffs such as Quinaldine Red, N-(p-hydroxyphenyl)-2,6-dichloro-p-benzoquinoneimine; oxazone dyestuffs such as 7-hydroxy-3H-phenoxazin-3-one 10-oxide; coumarin dyestuffs such as 6,7-dihydroxy-4-methylcoumarin; conductive polymer compounds such as aniline oligomer, and the like, in addition to Bromocresol Green.

For example, in the method using a reaction system in which a compound which develops color or changes in color by pH variations develops color or changes its color by an acid or a base, an analyte is measured by measuring an acid or base indirectly by measuring the formed dyestuff with an absorptiometer. In the method using a reaction system in which a compound which develops color or changes in color by pH variations develops color or changes its color by hydrogen ions, an analyte is measured by measuring the concentration of hydrogen ions by measuring the formed dyestuff with an absorptiometer.

Other dyestuffs which are formed by various reactions known as a coloration reaction and the like include azo dyestuffs formed by the coupling of a diazonium salt such as 2-methoxy-4-morpholino-benzenediazonium salt; dyestuffs formed by various known coloration reactions such as a reaction between aldehyde and 2,3-dimethyl-2,3-bis(hydroxyamino)butane; fluorescent substances formed by various known reactions such as a reaction between histamine and o-phthalaldehyde; and dyestuffs and fluorescent substances formed by the reaction of an enzyme substrate such as 4-methylumbelliferyl phosphate by an enzyme.

The azo dyestuffs formed by the coupling of a diazonium salt include azo dyestuff formed by coupling between indoxyl and 2-methoxy-4-morpholinobenzene-diazonium salt, azo dyestuff formed by coupling between urobilinogen and 3,3'-dimethoxybiphenyl-4,4'-diazonium salt, azo dyestuff formed by a reaction between 4-aminobenzenearsonic acid and N-1-naphthylethylene diamine in the presence of a nitrite, azo dyestuff formed by a reaction between 2,4-dichloroaniline and N,N-diethyl-N'-1-naphthylnaphthylethylene diamine oxalate in the presence of a nitrite, and the like.

In the above method using a reaction system in which an azo dyestuff is formed, an analyte (indoxyl, urobilinogen and nitrite in the above examples) as the starting substance of a reaction is measured by measuring the formed dyestuff with an absorptiometer or the like. The formation reaction of an azo dyestuff is not limited to the above examples but various known formation reactions of azo dyestuffs are suitably applied.

Dyestuffs formed by various known coloration reactions include dyestuffs formed by the following known coloration reactions, but the present invention is not limited to these as a matter of course. The coloration reactions include a reaction between hydrogen peroxide and 1,4-diaminobenzene for detecting aldehyde, the reaction of 2,3-dimethyl-2,3-bis(hydroxyamino)butane for detecting aldehyde, a reaction between 3-methyl-2-benzothiazolinonehydrazone and an oxidizing agent for detecting aldehyde, a reaction between 10H-phenothiazine and bromine for detecting secondary amine, the reaction of 2,2'-dithiodipyridine for detecting thiol and the like.

In the above method using a known coloration reaction, an analyte (aldehyde, secondary amine and thiol in the above examples) as the starting substance of a reaction is measured by measuring the formed dyestuff with an absorptiometer or the like. The known coloration reaction usable is not limited to the above examples as a matter of course.

Fluorescent substances formed by various known reactions include fluorescent substances formed by known detection reactions which are carried out using the following reagents. However, the present invention is not limited to these as a matter of course. The reagents used in the detection reactions which form fluorescent substances include 2-hydroxy-1,2-diphenylethanone for detecting a guanidino compound, o-phthalaldehyde for detecting histamine, o-phthalaldehyde for detecting spermidine, 1,2-diamino-4,5-dimethoxybenzene for detecting α-keto acid and the like.

In the above method using a known detection reaction, an analyte (guanidino compound, histamine, spermidine and α-keto acid in the above examples) as the starting substance of a reaction is measured by measuring the formed fluorescent substances with a fluorophotometer or the like. The known detection reaction usable is not limited to the above examples as a matter of course.

Enzyme substrates which form dyestuffs and fluorescent substances when they react in the presence of enzymes include N-tosyl-L-phenylalanine-2-amidoacridone as the substrate of chymotrypsin, L-alanine-2-amidoacridone as the substrate of aminopeptidase, 7-acetoxy-N-methylquinolinium salt for measuring esterase, 7-acetoxy-3H-phenoxazin-3-one as the substrate of esterase, 4-methylumbelliferyl phosphate as the substrate of phosphatase, 5,10,15,20-tetrakis(4-phosphonooxyphenyl)porphine as the substrate of phosphatase and the like. The present invention is not limited to these as a matter of course.

For example, in the above method using a reaction in which an enzyme substrate is decomposed by an enzyme, an analyte is measured by measuring an enzyme indirectly by measuring the formed dyestuff or the fluorescent substance with an absorptiometer or a fluorophotometer. The enzyme or the enzyme substrate may be chemically bonded to an antibody or a fragment thereof, for example.

Dyestuff complexes and fluorescent complexes formed by coordinate bonding and ion bonding include compounds which develop color or change their colors, such as dyestuffs and fluorescent substances produced by forming complexes by ion bonding or coordinate bonding between a metal ion or anion and a compound such as a ligand. The compounds which develop color or change their colors and form complexes with a metal ion include compounds known as metal indicators and chromoionophores and compounds which are colored by forming complexes with a colored transition metal ion. Specifically, the compounds include ethylene diamine tetraacetic acid, 2,2-bipyridine, 1-hydroxy-2-(2-hydroxyphenylazo)benzene, dibenzo-18-crown-6, dicyclohexyl-18-crown-6, cyclic polyamines, calix[4]arene, 3-[N,N-bis-(carboxymethyl)aminomethyl]-1,2-dihydroxyanthraquinone, 5',5"-dibromopyrogallolsulfone phthalein, 2-hydroxy-1-(1-hydroxy-2-naphthylazo)-6-nitro-4-naphthalene sulfonate, 2,6-dichloro-4'-hydroxy-3,3"-dimethyl-fuchsone-5',5"-dicarboxylate, 3,3'-bis[N,N-bis-(carboxymethyl)aminomethyl]fluorescein, 8-[N,N-bis(carboxymethyl)aminomethyl]-4-methylumbelliferone, 2,7-bis(2-arsonophenylazo)-1,8-dihydroxy-3,6-naphthalene disulfonic acid, 5-chloro-2-hydroxy-3-(2,4-dihydroxyphenylazo)benzenesulfonic acid, 5-[(hexahydro-2,4,6-trioxo-5-pyrimidinyl)imino]-2,4,6-(1H,3H,5H)-pyrimidinetrione salt, 2-(5-bromo-2-pyridylazo)-5-[N-propyl-N-(3-sulfopropyl)amino]aniline salt, 1,8-dihydroxy-2-(2-pyridylazo)-3,6-naphthalene disulfonate, 2-nitroso-5-[N-propyl-N-(3-sulfopropyl)amino]phenol and the like.

Compounds which form colored complexes with monovalent cations specifically include tetrakis[3,5-bis-(trifluoromethyl)phenyl] borate salt, tetraphenylphosphonium salt and the like.

Compounds which form fluorescent complexes with calcium ions specifically include 1-[2-amino-5-(2,7-dichloro-6-hydroxy-3-oxy-9-xanthenyl)phenoxy]-2-(2,7amino-5- methylphenoxy)ethane-N,N,N',N'-tetraacetate, 1-[2-amino-5-(2,7-dichloro-6-hydroxy-3-oxy-9-xanthenyl)phenoxy]-2-(2-amino-5-methylphenoxy)ethane-N,N,N',N'-tetraacetic acid-pentaacetoxymethyl ester, 1-[6-amino-2-(5-carboxy-2-oxazoyl)-5-benzofuranyloxy]-2-(2-amino-5-methylphenoxy)ethane-N,N,N',N'-tetraacetate, 1-[6-amino-2-(5-carboxy-2-oxazoyl)-5-benzofuranyloxy]-2-(2-amino-5-methylphenoxy)ethane-N,N,N',N'-tetraacetic acid-pentaacetoxymethyl ester, 1-[2-amino-5-(6-carboxy-2-indolyl)phenoxy]-2-(2-amino-5-methylphenoxy)ethane-N,N,N',N'-tetraacetate, 1-[2-amino-5-(6-carboxy-2-indolyl)phenoxy]-2-(2-amino-5-methylphenoxy)ethane-N,N,N',N'-tetraacetic acid-pentaacetoxymethyl ester, 8-amino-2-[(2-amino-5-methylphenoxy)methyl]-6-methoxyquinoline-N,N,N',N'-tetraacetate, 8-amino-2-[(2-amino-5-methylphenoxy)methyl]-6-methoxyquinoline-N,N,N',N'-tetraacetic acid-pentaacetoxymethyl ester, 3,3'-bis[N,N-bis(carboxymethyl)aminomethyl]fluorescein, 8-[N,N-bis(carboxymethyl)aminomethyl]-4-methyl-umbelliferone and the like.

Further, a tetraphenylarsonium salt which forms a colored complex with an anion, N-ethoxycarbonylmethyl-6-methoxyquinolinium bromide whose fluorescent intensity is reduced when it forms a complex with a chloride ion, 8-hydroxy-1-(salicylideneamino)-3,6-naphthalene disulfonate which forms a complex with boron and the like are also included.

In the above method using the formation reaction of a complex, an analyte (ions in most cases) is measured by measuring the amount of a dyestuff or a fluorescent substance formed by an ion and a ligand with an absorptiometer or a fluorophotometer.

(2) Electrochemically Detectable Substances

A description is subsequently given of electrochemically detectable substances.

Substances which can be detected by electrochemical methods include electron carriers (mediators) and complexes between ionophores and ions.

The electron carrier is a chemical substance which oxidizes/reduces an analyte with an enzyme or the like and receives/gives electrons directly from/to the analyte at the same time. The analyte can be measured from electrochemical response when the oxidized/reduced form of the electron carrier is oxidized/reduced by an electrode. The electron carrier does not need to receive/give electrons directly from/to the analyte and may be a chemical substance which oxidizes/reduces the analyte with an enzyme or the like and receives/gives electrons indirectly from/to the analyte at the same time. The analyte is measured from electrochemical response when the oxidized/reduced form of the electron carrier having quantitative relationship with the analyte is reduced/oxidized by an electrode.

The electron carrier is preferably oxidized/reduced by a potential within a range which can be measured by the used electrode (generally $-1.2$ V to $+1.0$ V in the case of a carbon electrode). The electron carrier is exemplified by 1,1'-dimethyl-4,4'-bipyridinium salt, 1,1'-dibenzyl-4,4'-bipyridinium salt, 1,4-diaminobenzene, 2-methyl-1,4-naphthoquinone, N-methylphenazinium salt, 1-hydroxy-5-methylphenazinium salt, 1-methoxy-5-methylphenazinium salt, 9-dimethylaminobenzo-α-phenoxazin-7-ium salt, ferrocene derivative, hexacyano iron(II) salt, 7-hydroxy-3H-phenoxazin-3-one-10-oxide, 3,7-diamino-5-phenylphenazinium salt, 3-(diethylamino)-7-amino-5-phenylphenazinium salt, 1,4-benzenediol, 1,4-dihydroxy-2,3,5-trimethylbenzene, N,N,N',N'-tetramethyl-1,4-benzenediamine, Δ2,2'-bi-1,3-dithiol, 2,6-dimethyl-benzoquinone, 2,5-dimethylbenzoquinone, 2,3,5,6-tetramethyl-2,5-cyclohexadiene-1,4-dione, 2,6-dichloro-4-[(4-hydroxyphenyl)imino]-2,5-cyclohexadien-1-one, 2,6-dichloro-4-[(3-chloro-4-hydroxyphenyl)imino]-2,5-cyclohexadien-1-one, 7-(diethylamino)-3-imino-8-methyl-3H-phenoxazine salt, 3,7-bis(dimethylamino)-phenothiazine-5-ium salt and the like.

Detectable substances in this case are oxidized/reduced forms of the above electron carriers, and the formation reaction of these detectable substances is the oxidation/reduction reaction of the electron carriers. As described above, an analyte can be measured by measuring electrochemical response such as an oxidation/reduction current when the oxidized/reduced form of an electron carrier existent having quantitative relationship with the analyte is reduced/oxidized by an electrode. For example, the analyte can be indirectly measured from the result of electrochemical response measured when the electron carrier is oxidized/reduced on an electrode as an electron donor/receptor like ascorbic acid or hydrogen peroxide.

The ionophore is a compound such as a ligand which is coordinately bonded or ion bonded selectively to a specific ion as an analyte to become a complex and it is particularly well known that the ionophore is used in a liquid film electrode.

Examples of the ionophore which forms a complex with a cation include tetrakis[3,5-bis(trifluoromethyl)phenyl]borate salt, tetraphenylphosphonium salt, valinomycin, cyclo(N',N'-dioctyl-D-asparaginyl-L-prolyl-L-alanyl)$_2$, bis(benzo-15-crown-5), bis[(benzo-15-crown-5)-4-methyl]pimelate, bis(12-crown-4), bis[(12-crown-4)methyl]-2-dodecyl-2-methylmalonate, 14-crown-4, dodecyl-methyl-14-crown-4,6,6-dibenzyl-1,4,8,11-tetraoxacyclotetradecane, dibenzo-18-crown-6, dicyclohexyl-18-crown-6, 4,16-di-N-octadecylcarbamoyl-3-oxabutyryl-1,7,10,13,19-pentaoxa-4, 16-diazacyclohenicosane and the like.

Examples of the ionophore which forms a complex with an anion include tetraphenylarsonium salt, 6-methoxy-N-(3-sulfopropyl)quinolinium salt and the like.

The liquid film electrode is used in a method of measuring a specific ion as an analyte, by measuring a membrane potential produced when a porous polymer layer is formed on the surface of an electrode, and an ionophore is infiltrated into the polymer layer, bonded to the specific ion contained in a sample and moved in the polymer layer to selectively separate the specific ion. It is a matter of course that the use of the ionophore in the electrochemical detection method is not limited to this liquid film electrode.

A specific ion as an analyte can be measured by measuring a membrane potential produced when the specific ion is bonded to an ionophore in a bulk solution and the ion is selectively separated in an electrode having a polymer layer in which unbonded ions cannot move and only a complex produced by bonding can move.

In this case, the detectable substance is a complex between the ionophore and the specific ion, and the formation reaction of the detectable substance is a complex formation reaction between the ionophore and the specific ion by coordinate bonding or ion bonding. An analyte is measured by electrochemically measuring a membrane potential produced according to the concentration of a specific ion which is the analyte as described above.

2. Measuring Method which the Present Invention is Applied to

The measuring method of the present invention is preferably applied to the method using a reaction system which forms such a detectable substance, more preferably to the following methods.

(a) A method using a reaction system including the formation reaction of hydrogen peroxide or an oxidization reaction using hydrogen peroxide as an oxidizing agent, specifically a method for measuring a dyestuff compound produced by forming hydrogen peroxide from an analyte through an oxidase reaction system and carrying out an oxidation-reduction reaction between the hydrogen peroxide and a reactive color producer (dyestuff precursor) in the presence of peroxidase.

(b) A method using a reaction system including the formation reaction of nicotinamide adenine dinucleotide (NADH) or nicotinamide adenine dinucleotide phosphate (NADPH) or a reaction using NADH or NADPH as a reducing agent, specifically a method for measuring a dyestuff compound produced by forming NADH or NADPH from an analyte through a dehydrogenase reaction system and reducing it by making it act on a dyestuff precursor in the presence of an electron carrier.

(c) A method for measuring a nitrite, diazonium salt or coupling compound by producing a diazonium salt by allowing a nitrite to react with an aromatic primary amine under an acidic condition to produce a diazonium salt, allowing the produced diazonium salt to react with a reagent to be coupled to produce an azo dyestuff and measuring the produced azo dyestuff.

(d) A method for measuring a substance labeled with a fluorescent enzyme substrate or an alkali phosphatase by measuring fluorescence generated by producing a fluorescent substance by isolating a phosphate from a fluorescent enzyme substrate such as 4-methyl-umbelliferone having a phosphoric acid ester by the function of alkali phosphatase and irradiating the fluorescent substance with excitation light.

(e) A method for measuring an oxidase/reductase and a substance labeled with an oxidase/reductase by measuring a current response when a mediator such as 1,4-diaminobenzene is oxidized/reduced by the oxidase/reductase and the produced oxidized/reduced form of the mediator is reduced/oxidized by an electrode reaction.

The detectable substance may be the analyte. As an example thereof, an analyte is measured by measuring electrochemical response when glucose dissolved in water is oxidized on the surface of an electrode.

The fourth measuring method of the present invention may be particularly a measuring method using a reaction system which forms a detectable substance in a solvent and including the formation reaction of a substance insoluble in the solvent, preferably to a measuring method in which an insoluble detectable substance is formed, particularly preferably to a measuring method in which the detectable substance is an optically detectable substance.

The solvent is not particularly limited and conventionally known solvents can be used. Examples of the solvent include water such as distilled water, alcohols such as ethanol, ketones such as acetone, ethers such as diethyl ether, esters such as ethyl acetate, halogenated hydrocarbons such as chloroform, aromatic hydrocarbons such as benzene and toluene, and the like. A solvent suitable for an analyte and a detection reaction system thereof can be selected from these. Out of these, water is preferred. It is known in dry chemistry that a sample liquid such as blood, saliva and urine containing an analyte can be used as a reaction solvent.

The measuring method using the formation reaction of a substance insoluble in a reaction solvent in which the reaction is carried out is not particularly limited. Examples thereof include a method using a reaction which forms an optically detectable substance insoluble in a reaction solvent, a method using a reaction which forms an optically detectable substance and a by-product insoluble in a solvent in which the reaction is carried out, and a method using a reaction which forms an electrochemically detectable substance and a by-product insoluble in a reaction solvent.

The measuring method using a reaction which forms an optically detectable substance insoluble in a reaction solvent is not particularly limited but it may be one of the following detection reactions.

Oxidation reactions include a reaction for detecting hydrogen peroxide by the oxidation condensation of phenol and 4-amino-1,2-dihydro-1,5-dimethyl-2-phenyl-3H-pyrazol-3-one in an aqueous solution, a reaction for detecting hydrogen peroxide which forms N-methylacridone, a fluorescent substance insoluble in water, by oxidizing N-methylacridine-9-carboxylate in an aqueous solution, a reaction for detecting hydrogen peroxide comprising a reaction for oxidizing an aqueous solution of 10-(carboxymethyl-aminocarbonyl)-3,7-bis(dimethylamino)phenothiazine salt in the presence of alkane sulfonate and causing it to develop color, and the like.

Reduction reactions include a reaction for detecting a reducing substance which forms 7-hydroxy-3H-phenoxazin-3-one, a fluorescent substance insoluble in an acidic aqueous solution by reducing 7-hydroxy-3H-phenoxazin-3-one-10-oxide, a reaction for detecting a reducing substance which forms a formazan dyestuff insoluble in water by reducing 3,3'-(3,3'-dimethoxy-4,4'-biphenylene)-bis[2-(p-nitrophenyl)-5-phenyl-2H-tetrazolium]salt 5-cyano-2,3-bis(4-methylphenyl)-2H-tetrazolium salt, 2,3-bis(4-cyanophenyl)-5-cyano-2H-tetrazolium salt or the like, and the like.

Other reactions include a reaction for detecting allyl sulfatase through a reaction between 4-methyl-umbelliferyl sulfate and aryl sulfatase in a weak acidic aqueous solution, a reaction for detecting β-glucosidase through a reaction between 2-chloro-4-nitrophenyl-β-D-glucopyranoside and β-glucosidase in an aqueous solution, a reaction for detecting aldehyde through a condensation reaction between azobenzene-p-phenylhydrazinesulfonic acid and aldehyde, a reaction for detecting nitrous acid including diazo coupling between a diazonium salt and 2-naphthol, a reaction for detecting a cobalt ion through a colored insoluble complex formation reaction between 1,3-diamino-4-(5-bromo-2-pyridylazo)benzene and a cobalt ion in a neutral aqueous solution, and the like.

The measuring method using the formation reaction of an optically detectable substance, which includes the formation reaction of a by-product insoluble in a reaction solvent, or the measuring method using the formation reaction of an electrochemically detectable substance, which includes the formation reaction of a by-product insoluble in a reaction solvent is rarely used because of inconvenience described in the above section of the related art. Therefore, examples of the above measuring methods are not enumerated herein. However, it is to be understood that the present invention is not limited by this.

It is a usually observed phenomenon that an insoluble substance separates out from a liquid phase immediately and is adsorbed to a solid phase nearby when it is formed in a solvent that does not dissolve it. If the solid phase does not exist nearby, the insoluble substance forms an assembly of molecules in a liquid phase, the assembly of molecules further grows and settles as an aggregate or precipitate. The layered inorganic compound of the present invention is a fine particle which is fine enough to be uniformly dispersed. Since insoluble detectable substances such as an insoluble detectable substance and a by-product in the present invention are a single molecule or a very small assembly of molecules immediately after they are formed, the insoluble substances are efficiently adsorbed to the layered inorganic compound and uniformly dispersed together.

The fourth measuring method of the present invention is a measuring method which causes a layered inorganic compound having a function to adsorb various kinds of substances and disperse uniformly to exist in a detection reaction system which forms an insoluble substance, thereby adsorbing the insoluble substance, and which overcomes such inconvenience produced by the insoluble substance as described in the section of the related art. In addition, the existence of the layered inorganic compound does not interrupt the proceeding of a detection reaction and detection. In the fourth measuring method of the present invention, the reaction system including the formation reaction of an insoluble substance is particularly preferably the reduction reaction of a tetrazolium salt.

Examples of the analyte which can be measured by the first to fourth measuring methods of the present invention include biological components in the body fluid such as urine and blood, trace amounts of substances existent in foods, medicines, or natural environment, industrial chemical substances, trace amounts of substances contained in waste, and the like.

3. Layered Inorganic Compound

The measuring method of the present invention is characterized in that a layered inorganic compound is caused to exist in the reaction system including the formation reaction of the detectable substance. A description is subsequently given of the layered inorganic compound.

The layered inorganic compound used in the present invention is an inorganic compound having a crystal structure of sheet-structured layers piled up one upon another, each layer composed of a set of polyhedrons such as Si tetrahedrons or Al octahedrons arranged on the same plane, as exemplified by layered clay minerals and hydrotalcite.

Clay minerals refer to aluminum silicate minerals which form the most part of clay (fine soil-like inorganic granular substance having plasticity in a wet state). They are generally composed of minimum structural units which are Si tetrahedrons having Si surrounded by 4 O's (oxygen atoms) and Al or Mg octahedrons having Al or Mg surrounded by 6 OH groups or O's.

The structure of the layered clay mineral is one in which a hexagonal net sheet is formed with Si tetrahedrons sharing one plane and O's at the remaining vertices oriented in the same direction (tetrahedral sheet), or a sheet is formed with Al (or Mg) octahedrons sharing ridgeangles (octahedral sheet), and these sheets are laminated one upon another. Minerals having such a structure that a plurality of 1:1 layers, each layer consisting of one tetrahedral sheet layer and one octahedral sheet layer, are laminated one upon another are called 1:1 type minerals, minerals having such a structure that a plurality of 2:1 layers, each layer consisting of one octahedral sheet layer and two tetrahedral sheet layers sandwiching the octahedral sheet layer, are laminated one upon another are called 2:1 type minerals, and minerals having such a structure that another octahedral sheet layer inserted between the layers of 2:1 type are called 2:1:1 type minerals. Minerals which comprises $Mg(OH)_2$ octahedral sheets and have metal ions at all octahedral positions are called trioctahedral type minerals and minerals which comprise $Al(OH)_3$ octahedral sheets and ⅓ of the octahedral positions are empty holes are called dioctahedral type minerals. The layered inorganic compound used in the present invention is preferably a 2:1 type mineral.

The layered inorganic compound used in the present invention preferably contains at least one element selected from lithium, sodium, potassium, magnesium, aluminum, silicon, oxygen, hydrogen, fluorine and carbon. The layered inorganic compound may be a compound represented by any one of the following formulas. The compound represented by any one of the following formulas may contain crystal water. These formulas are the formulas of mineralogically and chemically pure compounds. Since the actual layered inorganic compound may contain impurities such as sodium silicate, the chemical formula of the layered inorganic compound determined by elemental analysis does not always agree with one of these formulas as described in the document (D. W. Thompson, J. T. Butterworth, J. Colloid Interf. Sci., 151, 236–243 (1992)).

$$M_xSi_4(Al_{2-x}Mg_x)O_{12}X_2 \qquad (1)$$

wherein, M is any one of H, Li, Na and K, X is any one of OH and F, and x is a positive number of less than 2.

$$M_x(Si_{4-x}Al_x)Al_2O_{10}X_2 \qquad (2)$$

wherein, M is any one of H, Li, Na and K, and X is any one of OH and F, and x is a positive number of less than 4.

$$M_xSi_4(Mg_{3-x}Li_x)O_{10}X_2 \qquad (3)$$

wherein, M is any one of H, Li, Na and K, X is any one of OH and F, and x is a positive number of less than 3.

$$M_x(Si_{4-x}Al_x)Mg_3O_{10}X_2 \qquad (4)$$

wherein, M is any one of H, Li, Na and K, X is any one of OH and F, and x is a positive number of less than 4.

$$MSi_4Mg_{2.5}O_{10}X_2 \qquad (5)$$

wherein, M is any one of Li and Na, preferably Na, and X is any one of OH and F, preferably F.

$$M_2Si_4Mg_2O_{10}X_2 \qquad (6)$$

wherein, M is any one of Li and Na, preferably Li, and X is any one of OH and F, preferably F.

$$Mg_6Al_2(OH)_{16}X_x \qquad (7)$$

wherein, X is any one of halogen, $NO_3$, $SO_4$, $CO_3$ and OH or an anion of an organic acid, preferably $CO_3$, and x is 2 when X is halogen, OH, $NO_3$ or a monovalent organic acid and 1 when X is $SO_4$, $CO_3$ or a divalent organic acid.

$$Na_{0.33}Si_4(Mg_{2.67}Li_{0.33})O_{10}X_2 \qquad (8)$$

wherein, X is either OH or F, preferably OH.

$$Na_{a-b}(Si_{4-a}Al_a)(Mg_{3-b}Al_b)O_{10}X_2 \qquad (9)$$

wherein, X is either OH or F, preferably OH, a is a positive number of less than 4, and b is a positive number of less than 3, provided that a−b>0.

Examples of the layered inorganic compound used in the present invention include 1:1 type clay minerals such as kaolinite, halloysite and serpentine; 2:1 type clay minerals such as talc, pyrophyllite, smectite, vermiculite (represented by the formula 2 out of the above formulas) and mica including fluorotetrasilicic mica (formula 5) and taeniolite (formula 6); 2:1:1 type clay minerals such as chlorite; 2:1 to 2:1:1 type intermediate minerals; para-amorphous clay minerals such as imogolite; amorphous clay minerals such as allophane; hydrotalcite (formula 7); and the like.

According to ion species contained in the isomorphously substituted tetrahedron and octahedron, the smectite is divided into a dioctahedral type such as montmorillonite (formula 1), bentonite which is a natural product containing 40 to 80% of montmorillonite, and beidellite (formula 2); a trioctahedral type such as hectorite (formula 3, preferably formula 8), saponite (formula 4, preferably formula 9), and nontronite; and the like.

The hydrotalcite is a layered mineral represented by the above formula 7, specifically $Mg_6Al_2(OH)_{16}CO_3.4H_2O$ in which part of $Mg^{2+}$ of $Mg(OH)_2$ (brucite having a laminate structure consisting of oxygen octahedral layers having $Mg^{2+}$ at the center) is substituted by $Al^{3+}$ isomorphously. The hydrotalcite has a positive charge, maintains electrical neutrality by $CO_3^{2-}$ between layers and has anion exchangeability. It is not a silicate mineral but is often treated as a clay mineral.

The compositions of some of the above-described layered inorganic compounds used in the present invention are shown in Table 1 below.

TABLE 1

| Name of mineral | Composition* |
|---|---|
| Kaolinite | $Si_2Al_2O_5(OH)_4$ |
| Halloysite | $Si_2Al_2O_5(OH)_4 \cdot 2H_2O$ |
| Serpentine | $Si_2(Mg^{2+}, Fe^{2+})_3O_5(OH)_4$ |
| Talc | $Si_4Mg_3(OH)_2O_{10}$ |
| Pyrophyllite | $Si_4Al_2(OH)_2O_{10}$ |
| Montmorillonite | $MI_xSi4(Al_{2-x}Mg_x)O_{10}(OH)_2 \cdot nH_2O$ |
| Beidellite | $MI_x(Si_{4-x}Al_x)Al_2O_{10}(OH)_2 \cdot nH_2O$ |
| Hectorite | $MI_xSi_4(Mg_{3-x}Li_x)O_{10}(OH, F)_2 \cdot nH_2O$ |
| Saponite | $MI_x(Si_{4-x}Al_x)Mg_3O_{10}(OH)_2 \cdot nH_2O$ |
| Nontronite | $MI_x(Si_{4-x}Al_x)Fe_2O_{10}(OH)_2 \cdot nH_2O$ |
| Vermiculite | $MI_x(Si_{4-x}Al_x)Al_2O_{10}(OH)_2 \cdot nH_2O$ |
| Hydrotalcite | $Mg_6Al_2(OH)_{16}CO_3 \cdot 4H_2O$ |

*MI is an exchangeable cation represented by a monovalent cation.

The average particle diameter of the layered inorganic compound used in the present invention is not particularly limited if it is small enough to enable the uniform dispersion of the compound. Since the layered inorganic compound is generally a planer particle and has dynamic equilibrium that the aggregation and cleavage of several particles are repeated, it is difficult to define the average particle diameter thereof. It is not easy to specify a preferable average particle diameter range. Daring to say, the value measured by means such as light scattering method or observation through an electron microscope is preferably 1 nm or more and 20 μm or less, more preferably 10 nm or more and 2 μm or less when the layered inorganic compound is dispersed in water. Since the layered inorganic compound has ion exchangeability, it is considered that the layered inorganic compound adsorbs according to the charge and polarity of a dyestuff or the like. The ion exchangeability of the layered inorganic compound is derived from layer charge produced by the substitution of metal ions constituting a layer. Then, the absolute value of layer charge is preferably about 0.2 to 1 for groups of atoms of the compositions of the formulas shown in Table 1.

A layered inorganic compound containing transition metal ions such as iron ions as substituent ions in the structure or impurities is colored by the metal ions and further shows oxidizing/reducing properties and produces a side reaction with the result that it has poor transparency. Therefore, the layered inorganic compound is preferably not substituted by transition metal ions, but the present invention is not limited by this.

In the above layered inorganic compounds such as clay minerals, the distance, charge and polarity between layers can be adjusted in advance by establishing a pillar such as a quaternary ammonium salt.

Out of the above layered inorganic compounds used in the present invention, more preferred are 2:1 type clay minerals and particularly preferred are swelling clay minerals having ion exchangeability.

Out of the swelling clay minerals, more preferred are bentonite, smectite, vermiculite and synthetic fluorine mica, and particularly preferred are synthetic smectite such as synthetic hectorite and synthetic saponite, and synthetic mica (natural mica is generally a non-swelling clay mineral) such as swelling synthetic mica (Na type mica) typified by synthetic fluoro-mica. The swelling function of the swelling clay minerals is derived from an exchangeable cation or anion. A swelling layered inorganic compound is preferably used because the detectable substance is quickly adsorbed by the surface of the interlayers and the surface of a clay association called card house. Clay minerals may adsorb anionic substances, cationic substances and nonionic polar organic compounds, and hydrotalcite may adsorb anionic compounds. Compounds which can be adsorbed by the layered inorganic compounds are detailed in Chapter 11 "Interaction of Clays and Organic Compounds" of "An Introduction to Clay Colloid Chemistry, Second Edition" written by H. Van Olphen (Krieger Publishment, Malabar). They may be used alone or in combination of two or more in the present invention.

The above layered inorganic compound used in the present invention may be either synthetic or natural but is preferably synthetic. Unlike natural layered inorganic compounds, synthetic layered inorganic compounds is chemically uniform and make it possible to quantitatively handle the detectable substance which has been adsorbed and quantitatively and optically handle the detectable substance because they do not contain colored metals such as iron between layers and accordingly, have high transparency. "Synthetic" as used herein means that layered inorganic compounds are produced mainly by a hydrothermal synthetic method or melting method at least in the case of smectite. Swelling clay minerals obtained by purifying natural products are also preferably used.

These layered inorganic compounds are commercially available. Examples thereof include Lucentite SWN and Lucentite SWF (synthetic hectorite) and ME (fluoro-mica) of Co-op Chemical Co., Smecton SA (synthetic saponite) of Kunimine Kogyo Co., Thixopy W (synthetic hectorite) and Kyoword 500 (synthetic hydrotalcite) of Kyowa Chemical Industry Co., Raponite (synthetic hectorite) of Laporte Co., natural bentonite marketed by Nacalai Tesque Co., Multigel (bentonite) of Toyojun Kogyo Co., and the like (Names with captial initials are trade names.).

It is known that the above layered inorganic compounds adsorb organic compounds such as amines, polyenes and various dyestuffs. They have been used as a water treatment agent which adsorbs oil, dyestuffs and the like, a protein removing agent used in the production of wine, sweet sake and the like, as a decoloring and purifying agent which adsorbs and removes impurities, and the like. These layered inorganic compounds are known as a substance providing a specific reaction site by causing a phenomenon called "metachromasy" and further known as a substance improving the optical stability of a natural dyestuff in recent years.

However, in the first method of the present invention, it has been found that measurement sensitivity can be increased by allowing the detectable substance to be adsorbed by the layered inorganic compound. Therefore, by the addition of the layered inorganic compound, the measurement of hydrogen peroxide in the above reaction system using 4-AA and a hydrogen donor, for example, can be carried out more quantitatively. A case in which the sensitivity of measurement is increased by using a layered inorganic compound such as a clay mineral in the measurement of a substance has not been reported yet.

In the second method of the present invention, an attempt has been made to add these layered inorganic compounds to a reaction system based on the assumption that there are such effects that a complex is formed by the adsorption of the detectable substance to the layered inorganic compound, the detectable substance is protected from the reaction system, and the electron level which involves in a decomposition reaction is changed by adsorption. As a result, it has been found that the detectable substance is adsorbed by the layered inorganic compounds and the adsorbed detectable substance can exist fully stably in the presence of excessive hydrogen peroxide or ascorbic acid. By the addition of the layered inorganic compound, the measurement of hydrogen peroxide in the above reaction system using 4-AA and a hydrogen donor, for example, can be carried out with higher accuracy. A case in which a layered inorganic compound such as a clay mineral is added to a reaction system for measuring an analyte, to stabilize the formed detectable substance and improve the sensitivity and accuracy of the measurement of the analyte has never been reported yet.

In the third method of the present invention, it has been found that the formation reaction of the detectable substance is allowed to proceed in the presence of the layered inorganic compound for the purpose of analysis, and though its mechanism is not fully known, the reaction precursor of the detectable substance is adsorbed by the layered inorganic compound and concentrated on the surface of the layered inorganic compound to improve the rate of the formation reaction of the detectable substance, thereby making it possible to quicken measurement.

In the fourth method of the present invention, it has been found that even if an insoluble substance is formed, high-sensitivity quick detection can be made by dispersing the layered inorganic compound in the solvent of the reaction system including the formation reaction of the detectable substance. A case in which the layered inorganic compound such as a clay mineral is dispersed in a solvent to measure a substance has never been reported yet.

More surprisingly, measurement accuracy is not impaired by the addition of a layered inorganic compound as a detection reaction is not interrupted even when the layered inorganic compound is caused to exist in a reaction system.

A method for causing the layered inorganic compound to exist in the reaction system in the method of the present invention, depends on the reaction system used, and preferably, the layered inorganic compound is dispersed in the reaction medium of the reaction system in the form of any one selected from dispersion, sol, gel, slurry, agglomerate, aggregate and sintered porous body. The reaction medium of the reaction system may be the reaction solvent of the formation reaction of the detectable substance. In the fourth method of the present invention, it is the reaction solvent of the formation reaction of a substance insoluble in the reaction solvent.

To cause the layered inorganic compound to exist in the reaction system, more preferably, the layered inorganic compound is dispersed in a solvent and the resulting dispersion is added to the reaction system. The solvent is not particularly limited and any conventionally known solvents may be used. Examples of the solvent include water such as distilled water, alcohols such as ethanol, ketones such as acetone, ethers such as diethyl ether, esters such as ethyl acetate, halogenated hydrocarbons such as chloroform, aromatic hydrocarbons such as benzene and toluene, and the like, from which one suitable for an analyte and a detection reaction system thereof can be selected. Preferably, the layered inorganic compound is dispersed in a buffer which will be described hereinafter and the resulting buffer dispersion is added to the reaction system. It is known in dry chemistry that a sample solution such as blood, saliva and urine containing an analyte can be used as a reaction solvent.

The amount of the layered inorganic compound added is determined according to a reaction system used. Depending on the layered inorganic compound used, it is preferably such as to eliminate a case where the number of adsorption sites is too small for a detectable substance and the detectable substance cannot be adsorbed completely and remains in the solution, or a case where the number of adsorption sites is too large and there are differences in the concentration of the detectable substance adsorbed at these sites.

The preferable amount of the layered inorganic compound added to the reaction system is determined as follows. That is, since the layered inorganic compound adsorbs a dyestuff or the like in an amount corresponding mainly to the degree of the above layer charge, the total number of adsorption sites of the dyestuff or the like can be obtained for each type of layered inorganic compound. When the concentration of a reagent in a detection reaction system is determined, the approximate maximum amount of a formed dyestuff or the like can be calculated, and each type of layered inorganic compound can be added so that the maximum amount of the dyestuff or the like which can be formed does not exceed the whole adsorption sites of the layered inorganic compound.

The time for adding the layered inorganic compound is not particularly limited and may be before or after the formation reaction of the detectable substance. Preferably, the layered inorganic compound is added to a reaction system before the formation reaction of the detectable substance and dispersed in the reaction system.

The reason why the layered inorganic compound is dispersed in the reaction system is that interaction such as adsorption between the reaction starting substance, the reaction intermediate or the reaction product involved in the formation reaction of the detectable substance and the layered inorganic compound can readily occur. Another reason is that a state where the layered inorganic compound is uniformly dispersed without differences in concentration is suitable for detection. Therefore, the term "dispersion" as used herein means a state where the layered inorganic compound is dispersed in a solution or a state of a sol or gel, or a state suitable for detection where the above interaction readily occurs.

In the fourth method of the present invention, an insoluble substance can be adsorbed by the layered inorganic compound by uniformly dispersing the layered inorganic compound in the reaction solvent to make it existent in the reaction system.

The dispersion medium in which the layered inorganic compound is dispersed is not always the same as a reaction solvent in which a reaction takes place. The layered inorganic compound may be dispersed in a dispersion comprising a reaction solvent as a dispersion medium, or a sol, a gel, an agglomerate, an aggregate or a sintered porous body which the reaction solvent can permeate. The dispersion medium is not particularly limited if the layered inorganic compound can be uniformly dispersed therein.

The layered inorganic compound in the form of sol, gel, agglomerate, aggregate or sintered porous body which the reaction solvent can permeate can be used as a detection portion which also serves as a reaction portion in a testing piece in dry chemistry or the like. If the layered inorganic compound can be uniformly dispersed, the measuring method of the present invention can be applied to the testing piece.

When the layered inorganic compound having an exchangeable cation or exchangeable anion is dispersed in water by agitation or ultrasonication, an uniform dispersion can be obtained if it has an appropriate concentration. However, by the addition of an electrolyte or an organic compound or by long-time standing or temperature variations, the particles of the layered inorganic compound may agglomerate, aggregate or form a gel or precipitate. The agglomeration is generally caused by the gentle interaction of the particles and the particles can be re-dispersed by agitation easily.

The dispersion, agglomeration and re-dispersion of the layered inorganic compound are detailed, for example, in Chapter III "The Theory of Stability of Hydrophobic Sols", Chapter IV "Successes of the Theory of Stability—Further Theories and Refinement", Chapter VII "Electric Double-Layer Structure and Stability of Clay Suspensions" and Chapter VIII "Peptization of Clay Suspensions" of "An Introduction to Clay Colloid Chemistry, Second Edition" written by H. Van Olphen (Krieger Publishment, Malabar).

The degree of adsorption is influenced by the composition of a buffer (pH, ionic strength, components forming a complex, and the like). For example, smectite dispersed in purified water hardly adsorbs brilliant blue FCF whereas smectite dispersed in a bis-tris buffer solution having a pH of 6.5 (prepared from bis(2-hydroxyethyl)iminotris(hydroxymethyl)methane and hydrochloric acid] quickly adsorbs this dyestuff.

Examples of the buffer or buffer solution used in the method of the present invention include a phosphoric acid buffer solution, citric acid buffer solution, N-(2-acetoamide) imino diacetic acid buffer solution and the like, besides the above bis-tris buffer solution. The present invention is not limited to these and a suitable one is suitably selected according to the reaction system used. The pH, concentration and the like of the buffer are preferably suitably selected according to the reaction system used.

The time for adding the buffer is not particularly limited and may be before or after the addition of the layered inorganic compound. It is preferably added as a buffer solution containing the layered inorganic compound dispersed therein to a reaction system together with the layered inorganic compound.

4. Surfactant

In measurement with the method of the present invention, various surfactants can be added to the reaction system. Addition of a surfactant makes it possible to uniformly disperse a sample containing a hardly soluble substance and uniformly and quickly infiltrate the sample into the test portion of a testing piece by improving the wettability by the sample. Since the surfactant has a function to disperse or dissolve a substance adsorbed to the interface, it conflicts with the adsorption of the formed detectable substance to the layered inorganic compound or dissolve the formed detectable substance. Therefore, it may weaken the effect of the present invention. As the surfactant used in combination with the layered inorganic compound in the present invention, a surfactant which does not interfere the adsorption of the formed detectable substance to the layered inorganic compound is preferably selected. The amount of the surfactant used is preferably small enough to prevent the interference of the adsorption. To adjust the adsorption strength between the detectable substance such as a dyestuff and the layered inorganic compound, a known surfactant suitable for the reaction system may be used and the amount of the surfactant added may be controlled.

The type of surfactant which does not interfere the adsorption may be one of which molecular weight is not much larger than that of the formed dyestuff and the organicity and the inorganicity of which satisfy the following equation:

$$(\text{inorganicity})=(2.37\pm0.23)\times(\text{organicity})-186.2\pm117.1$$

The above equation is obtained by studying the adsorption interference effect and the relationship between the inorganicity and the organicity of each of various surfactants having known structures. That is, the number of points is allotted to each functional group or atom, for example, 20 is allotted to a single carbon atom as an organicity, 100 to a hydroxyl group as an inorganicity, 30 to polyethylene oxide as an organicity and 60 to the polyethylene oxide as an inorganicity, 70 to a nitro group as an organicity and 70 to the nitro group as an inorganicity. Then, the total of inorganicity values and the total of organicity values are obtained by summing the numbers of points for functional groups and atoms constituting a compound. There is known an organic conceptional diagram in which a total inorganicity and a total organicity are plotted on rectangular coordinates, compounds having similar properties are located in the same area of the rectangular coordinates, and common properties appears without depending on the structure of a compound (Yoshio Kohda, "Organic Conceptional Diagram—Basis and Application—", p. 11, Sankyo Shuppan (1984)). The inventors of the present invention have studied the adsorption interference effects and the relationship between the inorganic values and organic values of many surfactants having known structures and have found that surfactants which do not interfere the adsorption satisfy the above equation in the organic conceptional diagram. Although calculation data on the above organic conceptional diagram in the above book can be used for the calculation of the inorganicity and the organicity, the above equation was obtained from calculation data provided in "Personal Computer Organic Conceptional Diagram" program manufactured by Dr. Yoshio Honma (The Chemical Software Society of Japan and the like).

The type and amount of a surfactant which does not interfere adsorption can be selected as follows.

(1) Hydrogen peroxide is added to a reaction solution containing a predetermined amount of smectite, 4-AA and N-ethyl-N-(2-hydroxy-3-sulfopropyl)-3,5-dimethoxyaniline to develop color.

(2) A surfactant is added to a reaction solution having he same composition as in (1) above to the same concentration and hydrogen peroxide is added to develop color.

(3) Smectite is separated by appropriate means such as settling, centrifugal sedimentation or filtration, the color tone of the supernatant or filtrate is measured by a spectrophotometer, and the amounts of the formed dyestuff absorbed by the smectite are compared between (1) and (2). Alternatively, when flocculation caused by adsorption is observed, the amount of adsorption is evaluated with the degree of flocculation or settling.

(4) The type and amount of a surfactant which does not produce any difference between when it is added and when it is not added are selected.

Preferred examples of the surfactant which is selected by the above methods include sugar-alkyl ethers such as n-octyl-β-D-glucopyranoside; sugar-alkyl thioethers such as n-octyl-β-D-thioglucopyranoside and n-heptyl-β-D-thioglucopyranoside; super amides such as n-octanoyl-N-methylglucamide and n-nonanoyl-N-methylglucamide, sugar esters such as β-D-fructopyranosyl-α-D-glucopyranoside monodecanoate; N,N-bis(3-D-gluconamidepropyl)deoxycolamide and the like.

The amount of the surfactant added is not particularly limited and the proportion of the surfactant to the total amount of the layered inorganic compounds is not particularly limited as well. An amount suitable for the types of the surfactant and the layered inorganic compound and the reaction system may be selected. The surfactant is used in an amount that its effect can be exhibited sufficiently, for example, an amount which does not greatly exceed the critical micell concentration of the surfactant used in an aqueous solution. For example, a 0.3% aqueous solution of n-octyl-β-D-thioglucopyranoside, a 0.3% aqueous solution of β-D-fructopyranosyl-α-D-glucopyranoside monodecanoate and a 0.3% aqueous solution of N,N-bis(3-D-gluconamidepropyl)deoxycolamide are preferably used.

The surfactant is preferably used particularly when measurement is carried out by the first to third methods of the present invention.

5. Embodiments of Measuring Method

In a preferred embodiment of the measuring method of the present invention, the layered inorganic compound is added to the reaction system and dispersed in the reaction system in advance. In the dispersion, a translucent colloidal agglomerate may be produced but the agglomerate does not always need to be produced in the present invention. This agglomerate can be considered as a complex comprising the layered inorganic compound and the detectable substance adsorbed thereby. This agglomerate may be uniformly redispersed by stirring. When this agglomerate is inconvenient, the dispersibility of the layered inorganic compound is improved by using a phosphate buffer solution, thereby making it possible to suppress the production of an agglomerate.

It is also possible to further improve measurement sensitivity by allowing the detectable substance used finally for detection to be adsorbed by the layered inorganic compound, thereby settling it, and separating the detectable substance from the reaction system and concentrating it. The method for separating the layered inorganic compound by which the detectable substance has been adsorbed is not particularly limited and selected from, for example, settling, centrifugation, filtration, chromatography, electrophoresis, solvent evaporation and the like. Specifically, the filtration of a dispersion of the layered inorganic compound exemplified in the present invention can be carried out, for example, by using a polysulfone ultrafiltration membrane having an exclusion limit of about 10,000 or a pore size of about 5 nm.

In the present invention, the detectable substance adsorbed by the layered inorganic compound is measured. The measuring method may be selected from an absorption measuring method, fluorescence measuring method, luminescence measuring method, electrochemical measuring method, light scattering measuring method, reflectance measuring method or the like. Preferably, it is an optical measuring method such as colorimetry typified by absorptiometry using an absorptiometer or the like. Since the layered inorganic compound used in the present invention rarely absorbs light of a visible to near infrared range, even in the form of colloidal dispersion or gel, optical measurement can be carried out. When the dispersion is measured directly, such means as an opal glass method can be selected as the system. Since a porous structure which a reaction solvent can permeate can be fabricated using the layered inorganic compound as described later, a testing piece having this portion as a detection portion which also serves as a reaction portion is used to carry out reflectance measurement, absorption measurement, fluorescence measurement and the like. An electrochemical measuring method for measuring an oxidation/reduction current or a membrane potential with an electrode can also be used. The electrode is contacted to the layered inorganic compound by which the detectable substance has been adsorbed to measure electrochemical response with high sensitivity.

II. Testing Piece of the Invention

The testing piece of the present invention is an analytical testing piece for measuring an analyte by measuring a detectable substance which is formed when the analyte contained in a sample reacts with a reagent. The testing piece comprises at least one test portion having a detection portion for detecting the detectable substance.

The test portion is a functional portion responsible for a series of analytical processes of the absorption, diffusion, reaction, detection and the like of the sample in the testing piece. The test portion, whose structure is not particularly limited, generally comprises the detection potion for detecting the detectable substance such as a dyestuff with reflectance, transmission/absorption, fluorescence or the like; a sample suction portion, provided at the end or near the end of the test portion, for sucking and introducing the sample into the test portion; a diffusion/infiltration portion for uniformly infiltrating and diffusing the sample into the test portion; a reagent portion containing a reagent which reacts with the analyte contained in the sample; a reaction portion where a reaction such as a detection reaction takes place; a developing portion for separating a component contained in the sample or a dyestuff formed by the detection reaction by a function similar to chromatography; a time control portion for controlling the proceeding of a reaction by utilizing the time during which the sample moves; a holding portion for trapping or removing a component contained in the sample or the formed dyestuff by an adsorption function; an absorption portion, provided at the end or near the end of the test portion on a side opposite to the sample suction portion with respect to the detection portion, for absorbing excess of a sample solution, a washing solution and a developing solution to prevent a back flow; and the like.

These portions bearing the functions of the test portion may overlap with one another in function. A single portion may have a plurality of functions, for example, the detection portion may also serve as the reagent portion and the reaction portion, and the detection portion may also serve as the holding portion.

A preferred embodiment of the testing piece of the present invention is a testing piece comprising at least one multi-layered test portion composed of two or more layers including a detection layer for detecting the detectable substance as the detection portion. Layers other than the detection layer include a sample suction layer for sucking a sample and introducing it into the test portion; a diffusion layer for uniformly infiltrating and diffusing the sample into the test portion; a reagent layer containing a reagent which reacts with the analyte contained in the sample; a reaction layer where a reaction such as a detection reaction takes place; a developing layer or holding layer, formed between the reaction layer and the detection layer, having a function to remove an interfering component; an absorption layer for absorbing excess of the sample, a washing solution or a developing solution added to prevent a back flow; an adhesive layer for fixing the test portion on the support; and the like. Particularly preferably, it is a testing piece comprising a diffusion layer for diffusing the sample in addition to the detection layer so that the sample passes through the diffusion layer to be diffused and reaches the detection layer. The testing piece of the present invention may be a testing piece having a single test portion or a multi-item testing piece having two or more test portions. In the case of the multi-item testing piece, a plurality of samples can be analyzed at the same time, and two or more analytes contained in the sample can be analyzed at the same time by using different reagents for different items.

Another preferred embodiment of the testing piece of the present invention is a testing piece comprising at least one test portion having a detection area for detecting the detectable substance as the detection portion. On the testing piece can be formed areas other than the detection area, such as a sample suction area for sucking and introducing a sample into the test portion; a diffusion area for uniformly infiltrating and diffusing the sample into the test portion; a reagent area containing a reagent which reacts with an analyte contained in the sample; a reaction area where a reaction such as a detection reaction takes place; a developing area for separating a component contained in the sample or a dyestuff formed by a detection reaction by a function similar to chromatography such as adsorption or distribution; a time control area for controlling the proceeding of a reaction using the time during which the sample moves; a holding area for trapping or removing a component contained in the sample or the formed dyestuff by an adsorption function; an absorption area for absorbing excess of a sample solution, a washing solution or a developing solution to prevent a back flow; and the like. Particularly preferably, it is a testing piece which comprises a diffusion area for diffusing the sample in addition to the detection area so that the sample dropped onto the end or the like of the testing piece can pass through the diffusion area, move over the plane of the testing piece mainly by a capillary infiltration action and reach the detection area. In this case, the detection area may have the above multi-layer structure composed of two or more layers including the detection layer for detecting the detectable substance. The testing piece of the present invention may be a testing piece comprising only one test portion composed of one set of the detection area and the reagent area, or a multi-item testing piece comprising two or more test portions thereon. In the case of the multi-item testing piece, a plurality of samples can be analyzed at the same time, and two or more analytes contained in the sample can be analyzed at the same time by using different reagents for different items.

In the present invention, the reaction portion where the analyte contained in the sample reacts with the reagent may be provided separately from the detection portion so that the detectable substance is formed in the reaction portion and then introduced and detected in the detection portion. In this case, the detection portion is preferably provided at a position which the sample reaches after it is diffused and passes through the reaction portion. Specifically, the detection layer is preferably formed at a position which the sample reaches after it permeates from the surface of the multi-layered test portion, passes through the diffusion layer to be diffused, moves to the reaction layer as an intermediate layer and passes through the reaction layer. The detection area, the reaction area and the diffusion area are formed on the testing piece, and the detection area is preferably formed in an area which the sample reaches after it moves over the plane, permeates through the diffusion area, moves to the reaction area and passes through the reaction area.

In the present invention, the detection portion may also serve as the reaction portion where the analyte contained in the sample reacts with the reagent so that the detectable substance can be formed by a reaction between the analyte contained in the sample and the reagent in the detection portion.

The detection portion in the present invention is a portion where the detectable substance such as a dyestuff formed by a reaction between the analyte contained in the sample and the reagent is actually detected. However, the detection portion may also serve as the reaction portion where the above reaction takes place or the reagent portion containing the reagent as described above. In this case, the reagent is generally contained in the detection portion in advance. Meanwhile, in the present invention, the testing piece may have a detection portion independent from the reaction portion and the reagent portion. In this case, the reagent may not be contained in the test portion and may be added before and/or after the addition of the sample. Or, a solution of the detectable substance such as a dyestuff formed by a reaction between the analyte and the reagent may be added.

The testing piece of the present invention generally comprises the test portion and a support portion shaped like a sheet, a tube or a rod for supporting the test portion, and optinally a sensor such as an electrode, a sample solution suction device and the like.

The present invention is preferably applied to a testing piece which uses a reagent which can form the detectable substance such as a dyestuff and the reaction system as described hereinafter.

The reagent is not particularly limited if it can form a complex by interaction such as adsorption between the detectable substance such as a dyestuff formed by a reaction and the layered inorganic compound used in the present invention as described in the section of the measuring method of the present invention.

The reagent for forming the detectable substance to be adsorbed by the layered inorganic compound or the like can be widely found in compounds such as a dyestuff precursor for forming an optically detectable substance such as a dyestuff or a fluorescent dyestuff through an oxidation-reduction reaction, an acid-base reaction, a condensation reaction, a complex formation reaction and the like, compounds for forming the electrochemically detectable oxidized/reduced form of an electron carrier or a complex compound, and the like.

Since the sample, the reagent or the reaction product is often in the form of a solution comprising water as a solvent, if the detectable substance is water-soluble, it is readily diffused and eluted. Therefore, when the detectable substance is water-soluble, the effect of the present invention is particularly marked. Therefore, the used reagent is preferably a reagent for forming a water-soluble detectable compound. In fact, a large number of such reagents are used. However, the reagent is not limited to these. The sample, the reagent or the reaction product may be dissolved in a solvent other than water. In this case, the used reagent may be a reagent for forming a detectable substance which is diffused and eluted by that solvent. A reagent for forming a detectable substance insoluble in the solvent of the sample, the reagent or the reaction product may be used.

Any reagents are acceptable if they form detectable substances as listed in the description of the measuring method of the present invention. Preferred examples of the reagent include compounds having a conjugate system such as an aromatic ring, specifically reagents (which form quinone dyestuffs when oxidation-condensed) for a coupler typified by 4-amino-1,2-dihydro-1,5-dimethyl-2-phenyl-3H-pyrazol-3-one and a hydrogen donor (N-ethyl-N-(3-sulfopropyl)-3,5-dimethylaniline and the like) as dyestuff precursors; dyestuff precursors for forming color-producing dyestuffs by oxidation such as o-tolidine and benzidines (3,3',5,5'-tetramethylbenzidine and the like); leuco substances (developing color when oxidized) of dyestuffs such as 2,6-dichloro-4-[(4-hydroxyphenyl)imino]-2,5-cyclohexadien-1-one; compounds for forming fluorescent substances when oxidized, such as 4-hydroxyphenylacetic acid; luminescent substances such as chemiluminescent substances; reagents for forming dyestuffs when reduced, such as tetrazolium salt (forming formazan when reduced) and 1,1'-dimethyl-4,4'-bipyridinium salt; compounds which develop color or change their colors by pH variations, such as Bromocresol Green; known reagents for coloration reactions such as diazonium salts (forming azo dyestuffs by coupling) including 2-methoxy-4-morpholinobenzenediazonium salt and 2,3-dimethyl-2,3-bis(hydroxyamino)butane (developing color when reacting with aldehyde); known reaction reagents such as o-phthalaldehyde (forming a fluorescent substance when reacting with histamine); enzyme substrates such as 4-methylumbelliferyl phosphate; compounds which develop color or change their colors by forming a complex such as 2-(5-bromo-2-pyridylazo)-5-[N-propyl-N-(3-sulfopropyl)amino]aniline salt; and compounds capable of forming the above detectable substances.

Reaction systems for forming the above detectable substances are those used in the measuring method as described in the section of the measuring method of the present invention. The reaction systems include the following.
(a) A reaction system including a reaction for forming hydrogen peroxide or an oxidation reaction using hydrogen peroxide as an oxidizing agent.
(b) A reaction system including a reaction for forming nicotinamide adenine dinucleotide (NADH) or nicotinamide adenine dinucleotide phosphate (NADPH) or a reaction in which NADH or NADPH functions as a reducing agent.
(c) A reaction system using a reaction for forming a diazonium salt by allowing nitrous acid to react with an aromatic primary amine in the presence of an acid.
(d) A reaction system including a reaction in which a fluorescent enzyme substrate such as 4-methyl-umbelliferone having a phosphoric acid ester forms a fluorescent substance by separating a phosphate by the function of alkali phosphatase.
(e) A reaction system including a reaction for forming an oxidized/reduced form of an electron carrier by oxidizing/reducing the electron carrier such as 1,4-diaminobenzene with an oxidizing/reducing enzyme.

Analytical methods using the above reaction systems include immunoassay such as ELISA, immunochromatography, urine examination, biochemical blood examination, colorimetry and the like. Testing pieces used in these analytical methods are detailed in such documents as H. G. Curme, et al., Clinical Chemistry, 24 (8), 1335–1342 (1978); B. Walter, Analytical Chemistry, 55 (4), 498A (1983); Asaji Kondo, Bunseki, 1984 (7), 534; Asaji Kondo, Bunseki, 1986 (6), 387; Bunseki Kagaku Binran, p.8 (edited by the Japan Society for Analytical Chemistry: fourth revised edition, Maruzen (1991)); Japanese Patent Application Laid-open No. 6-213886 (1994) (Masao Kitajima, et al.); M. P. Allen, et al., Clinical Chemistry, 36 (9), 1591–1597 (1990); D. Noble, Analytical Chemistry, 65 (23), 1037A (1993); R. F. Zuk, et al., Clinical Chemistry, 31 (7), 1144–1150 (1985) and the like. Analytes which can be analyzed by these methods include biological components contained in the body fluid such as urine and blood, trace amounts of substances existent in foods, medicines or natural environment, industrial chemical substances, trace amounts of substances contained in waste, and the like. The testing piece of the present invention can be used in the analysis of these substances.

A sample to which the testing piece of the present invention can be applied may contain only one analyte or two or more analytes.

A known compound which is generally used in an analytical testing piece, such as a hydrophilic polymer, can be contained in the test portion of the testing piece of the present invention as required.

In the present invention, a layered inorganic compound must be contained in the test portion of the testing piece, preferably the detection portion which is a portion where a formed dyestuff exists of the test portion.

That is, the layered inorganic compound must be contained in at least one detection layer or detection area constituting the test portion. Specifically, in a multi-layered test portion composed of two or more layers including the detection layer, the layered inorganic compound is contained at least in the detection layer. In this case, the layered inorganic compound may be further contained in a layer other than the detection layer, for example, the sample suction layer, the diffusion layer, the reagent layer, the reaction layer, the adhesive layer, the holding layer, the developing layer, the absorption layer or the like.

When the test portion has the detection area, the layered inorganic compound is contained at least in the detection area. Further, the layered inorganic compound may be further contained in an area other than the above detection area, for example, the sample suction area, the diffusion area, the reagent area, the reaction area, the developing area, the time control area, the holding area, the absorption area or the like. In this case, the detection area may have a multi-layer structure. In this case, the layered inorganic compound is contained at least in the detection layer out of layers constituting the detection area. The layered inorganic compound may be further contained in other layer.

When the test portion has a reaction portion where an analyte contained in a sample reacts with a reagent besides the detection portion, the detection portion is preferably provided at a position which the sample reaches after it is diffused and passes through the reaction portion so that the detectable substance formed in the reaction portion moves to the detection portion containing the layered inorganic compound to be detected.

Examples of the layered inorganic compound used in the testing piece of the present invention include those listed in the above description of the measuring method of the present invention. Like the measuring method of the present invention, out of these layered inorganic compounds, preferred are 2:1 type clay minerals and particularly preferred are swelling clay minerals having ion exchangeability. Out of the swelling clay minerals, more preferred are bentonite, smectite, vermicullite, and synthetic mica (natural mica is generally a non-swelling clay mineral) such as swelling synthetic mica (or Na type mica) typified by synthetic fluoro-mica, and particularly preferred are synthetic smectite such as synthetic hectorite and synthetic saponite, and synthetic fluoro-mica. They may be used alone or in combination of two or more. No attempt has been made so far to contain a layered inorganic compound in a testing piece utilizing its effect of suppressing the diffusion or elution of a dyestuff or the like.

Surprisingly, when the layered inorganic compound is added to the test portion such as the detection portion, a detection reaction is not interfered. Thereby, addition of this layered inorganic compound makes it possible to carry out examination making use of, for example, the above reaction system using 4-AA and a hydrogen donor more accurately and easily without being worried by elution.

A portion containing the layered inorganic compound of the test portion is preferably a porous structure, though its substance is not particularly limited, but it is preferably formed mainly by the layered inorganic compound, or the layered inorganic compound and at least one porous substance selected from the group consisting of hydrophilic polymers, membrane filters, fiber assemly such as filter paper, cloth, and glass filters, and organic and inorganic compound fine powders such as cellulose and diatomaceous earth.

The porous structure formed by the layered inorganic compound is a sol, a gel, an agglomerate or aggregate of the layered inorganic compound, or a porous body obtained by drying or sintering these. A buffer to be described later may be added to the porous structure. For example, a drop of a 1% dispersion of the layered inorganic compound is let fall upon a support, cast and lyophilized to obtain an absorptive porous layer.

The support may be shaped like a sheet, a tube or a rod. The material of the support is not particularly limited and may be selected from fiber assembly such as filer paper, nonwoven cloths, cloths and glass filters; granular substances such as glass beads, polymer beads and titanium dioxide; granular substances and fine powders such as cellulose, diatomaceous earth, soluble salt and hydrophobic polysaccharide powders; membrane filters; organic polymers such as plates of plastic including polyethylene terephthalate (PET) and polystyrene; and the like. More preferably, the substance is a gel of a hydrophilic polymer, or a membrane filter or a plastic plate whose surface is made hydrophilic.

The hydrophilic polymer may be a polymer, a copolymer, an associated substance or the like containing a chemical structure such as an polyalkylene oxide exemplified by polethylene oxide and polypropylene oxide; cellulose derivative exemplified by carboxymethyl cellulose and hydroxyethyl cellulose; gelatin or derivative thereof (such as phthalated gelatin); other polysaccharide or derivative thereof (agarose, carrageenan, chitin, chitosan or the like); polyvinyl alcohol; polyvinyl pyrrolidone; polyacrylate (sodium polyacrylate, copolymer thereof with maleic acid or the like); polyacrylamide; polymethacrylic acid (polyhydroxyethyl methacrylate or the like); methacrylamide; polysulfone; polyimide; polystyrene; polycarbonate; polyether ether ketone; polyoxymethylene; sodium alginate; or polyolefin resin exemplified by polyethylene, polypropylene or polyfluoroethylene which is made hydrophilic (by exposure to ultraviolet light, silanol treatment or the like).

Preferably, the above hydrophilic polymer has a network structure produced by graft polymerization using a crosslinking agent or association due to hydrophobic affinity and is insoluble in water.

Examples of the hydrophilic polymer include polylysine crosslinked by glutaraldehyde, polyethylene oxide crosslinked product, polyacrylamide graft polymer, polyacrylate graft polymers, starch-acrylate graft polymers and the like.

At least one porous substance selected from the group consisting of hydrophilic polymers, membrane filters, fiber assembly and organic and inorganic compound fine powders and the layered inorganic compound may be both contained in the test portion to form the porous structure. To form this porous structure, a method in which a mixture solution of a porous structure forming substance and the layered inorganic compound is prepared and cast on or impregnated into the above-described support, a method in which a porous structure forming substance is used to form a porous support such as a porous film and a dispersion or a mixture solution of the layered inorganic compound is cast or impregnated into the porous support, or the like may be used.

To mix the layered inorganic compound at the time of production of the porous structure, for example, a method in which the layered inorganic compound is kneaded with a hydrophilic polymer or fine powders and formed into a film is used. Alternatively, a buffer solution having the layered inorganic compound dissolved or dispersed in a buffer to be described later may be dried and the obtained dried product may be mixed with a raw substance.

When the dispersion or the mixture solution of the layered inorganic compound is impregnated into the porous support, the type of solvent used is not particularly limited and conventionally known solvents can be used. A solvent suitable for the detection reaction system used can be selected from water such as distilled water, alcohols such as ethanol, ketones such as acetone, ethers such as diethyl ether, esters such as ethyl acetate, halogenated hydrocarbons such as chloroform, and aromatic hydrocarbons such as benzene and toluene. Preferably, the porous support is impregnated with a buffer solution comprising the layered inorganic compound dissolved or dispersed in a buffer to be described later. The concentration of the solution or dispersion can be suitably selected according to a reaction system or the like and is not particularly limited.

A method for forming a layer or an area containing the layered inorganic compound will be described below.

To form the layer or the area containing the layered inorganic compound, a porous structure obtained by drying or sintering a sol, a gel, an agglomerate or an aggregate of the layered inorganic compound can be used. For example, a drop of a 1% dispersion of the layered inorganic compound is cast on a plastic sheet, and lyophilized to obtain a porous layer having high absorptivity.

At least one porous structure forming substance selected from the group consisting of the above hydrophilic polymers, membrane filters, fiber assembly and organic and inorganic powders can be used in the formation.

The hydrophilic, polymer is particularly preferably gelatin, polyacrylic acid or derivative thereof, polyacrylamide, polyvinyl alcohol, polyvinylpyrrolidone, polyethylene glycol, polysaccharide or derivative thereof, polypeptide, or polyamine or derivative thereof. The hydrophilic polymer may be used as a gel or a dried product thereof. The hydrophilic polymer may be a gel whose degree of crosslinking is controlled by the addition of a known crosslinking agent such as glutaraldehyde. These hydrophilic polymers may be used alone or in combination.

To obtain a porous structure comprising the above substance and the layered inorganic compound, various methods already described in the section of the method for containing the layered inorganic compound in the test portion can be used. For example, a 1% dispersion of the layered inorganic compound dispersed in a buffer solution is impregnated into filter paper and dried with hot air to obtain a porous area. A small piece of the filter paper is affixed to a plastic sheet to obtain a porous layer.

The following procedure, for example, can be employed. The same amount of an aqueous solution of a polyacrylamide having a predetermined concentration is mixed with a 3% dispersion of the layered inorganic compound in a polyacrylamide/layered inorganic compound weight ratio of 1:1 to 4:1 and stirred well for several hours. pH of the resulting mixture solution is adjusted to about 5 to 9 by adding a diluted aqueous solution of sodium carbonate or acetic acid if necessary. If necessary, the mixture solution is made alkaline, N,N-methylenebisacrylamide is added to a concentration of 2%, and the mixture solution is exposed to electron beams to cause a crosslinking reaction. The thus obtained mixture solution is coated on a plastic plate and dried to obtain a porous film.

The thus formed porous structure containing the layered inorganic compound is excellent particularly in absorptivity and preferably used as the test portion of a testing piece. As a matter of course, the formation example of the test portion is not limited to this. For example, the formation of the test portions of various known testing pieces can be applied. These testing pieces are described in such documents as H. G. Curme, et al., Clinical Chemistry, 24 (8), 1335–1342 (1978); B. Walker, Analytical Chemistry, 55 (4), 498A (1983); Asaji Kondo "Bunseki" 1984 (7), 534; R. F. Zuk, et al., Clinical Chemistry, 31 (7), 1144–1150 (1985); Asaji Kondo, Bunseki, 1986 (6), 387; Japanese Patent Application Laid-open No. 2-6541(1990) (K. Hildenbrand); M. P. Allen, et al., Clinical Chemistry, 36 (9), 1591–1597 (1990); Japanese Patent Application Laid-open No. 3-163361(1991) (E. J. Kiser, et al.); Bunseki Kagaku Binran, p. 8 (edited by the Japan Society for Analytical Chemistry: Fourth Revised Edition, Maruzen (1991)); D. Noble, Analytical Chemistry, 65 (23), 1037A (1993); Japanese Patent Application Laid-open No. 5-157745(1993) (Hidehiko Manabe, et al.); Japanese Patent Application Laid-open No. 6-213886(1994) (Masao Kitajima, et al.); Japanese Patent Application Laid-open No. 6-222061(1994) (H. Brandt, et al.); and the like.

The concentration of a dispersion of the layered inorganic compound, the mixing ratio thereof to the hydrophilic polymer and a pH value to be controlled are suitably selected based on parameters such as the type of the layered inorganic compound, the type of a dyestuff to be adsorbed, the type and amount of the hydrophilic polymer used, the type and amount of the buffer and the viscosity of the mixture solution so as to obtain a porosity, a film thickness of the porous layer and a mechanical strength of the test portion which are required.

By adding a reagent which reacts with an analyte contained in a sample solution to form the detectable substance to the porous structure thus formed, the porous structure can be used as the test portion of the testing piece.

The amount of the layered inorganic compound added is determined according to a reaction system used. Depending on the layered inorganic compound used, it is preferably such as to eliminate a case where the number of adsorption sites is too small for the formed substance and the formed substance cannot be adsorbed completely and remains in the solution, or a case where the number of adsorption sites is too large and there are differences in the concentration of the formed substance adsorbed at these sites, as in the measuring method of the present invention. As for the preferred amount of the layered inorganic compound to be added to the reaction system, the total number of adsorption sites for a dyestuff or the like can be obtained for each type of layered inorganic compound, and each type of layered inorganic compound can be added so that the maximum amount of the dyestuff or the like which can be formed does not exceed the whole adsorption sites of the layered inorganic compound.

As described above, since the degree of adsorption is influenced by the composition (pH, ion strength, complex forming components and the like) of a buffer, it can be adjusted to a desired degree by changing the composition, concentration or pH of the buffer, or changing the amount of a compound added which can compete with a dyestuff or the like in adsorption to the layered inorganic compound. Examples of the competitive compound include metal ions, organic amines, carboxylic acids, phosphates and the like. Surfactants and soluble polymers can also be used.

The type of a buffer or a buffer solution used, the pH and concentration of the buffer, and the like are the same as those described in the section of the measuring method of the present invention.

The method of adding a buffer is not particularly limited. A buffer may be added as a buffer solution having the layered inorganic compound dissolved or dispersed therein or contained as a dried product together with the layered inorganic compound.

In the production of a testing piece, although a translucent colloidal agglomerate may be formed in a dispersion of the layered inorganic compound, this agglomerate is uniformly re-dispersed by stirring the dispersion. When the agglomerate is particularly inconvenient, it is recommended to use a phosphate buffer solution to improve the dispersibility of the layered inorganic compound, thereby making it possible to suppress the formation of the agglomerate.

Various surfactants can be further contained in the test portion. Addition of a surfactant improves the coating properties of the test portion or the like on the support. Since the surfactant has functions to adsorb to the interface and disperse or dissolve a substance, it conflicts with the adsorption of the formed detectable substance to the layered inorganic compound or dissolve the formed detectable substance, whereby the effect of the present invention may be weakened. Therefore, a surfactant which does not interfere the adsorption of the formed detectable substance to the layered inorganic compound is preferably selected as the surfactant to be used in combination of the layered inorganic compound in the present invention. The amount of the surfactant used is preferably so small as to avoid the above interruption. The type and amount of the surfactant are the same as those described in the above section of the measuring method of the present invention.

EXAMPLES

The following examples are given to further illustrate the present invention.

Example 1

Peroxidase (POD), 4-AA and N-ethyl-N-(2-hydroxy-3-sulfopropyl)-3,5-dimethoxyaniline (to be abbreviated as EHSDA hereinafter) as dyestuff precursors, bis-tris buffer (pH 6.5) as a buffet, and smectite as a layered inorganic compound were taken to final concentrations shown in Table 2, and hydrogen peroxide was added to these to a final concentration of 120 μmol/l and allowed to react to obtain a reaction solution. The absorption spectrum of an agglomerated portion of the obtained reaction solution was measured at a wavelength of 450 to 750 nm.

POD, 4-AA, EHSDA and a bis-tris buffer were taken to final concentrations shown in Table 3, and hydrogen peroxide was added to these to a final concentration of 120 μmol/l and allowed to react to obtain a reaction solution. The absorption spectrum of the obtained reaction solution was measured at a wavelength of 450 to 750 nm as well.

The measurement of absorbance was carried out using the JascoV-550 (Japan Spectroscopic Co. Ltd.) at intervals of 0.5 nm. The scanning rate was 200 nm/min and the bandwidth was 1.0 nm. A disposable cell having a cell length of 1 cm (made from polymethyl methacrylate) was used and a 0.1-ml slit was used to measure only an agglomerated portion as an agglomerate was produced when smectite was added. The results of measurement are shown in FIG. 1.

TABLE 2

| Reagent | Final concentration |
| --- | --- |
| POD (peroxidase) | 1 U/mil |
| 4-AA*1 | 2 mmol/l |
| EHSDA*2 | 2 mmol/l |
| Bis-tris buffer*3 | 100 mmol/l |
| Smectite*4 | 0.1% |
|  | (total amount of 3 ml) |

*1) 4-aminoantipyrine(4-amino-1,2-dihydro-1,5-dimethyl-2-phenyl-3H-pyrazol-3-one)
*2) N-ethyl-N-(2-hydroxy-3-sulfopropyl)-3,5-dimethoxyaniline
*3) bis(2-hydroxyethyl)iminotris(hydroxymethyl)methane
*4) Lucentite SWN (synthetic smectite: manufactured by Co-op Chemical Co.)

The reagents used are shown in Table 4 below.

TABLE 3

| Reagent | Final concentration |
| --- | --- |
| POD | 1 U/ml |
| 4-AA | 2 mmol/l |
| EHSDA | 2 mmol/l |
| Bis-tris buffer | 100 mmol/l |
|  | (total amount of 3 ml) |

TABLE 4

| Reagent | Reagent concentration | Maker | Reagent purity |
| --- | --- | --- | --- |
| POD | 30 U/ml | Toyobo |  |
| 4-AA | 60 mmol/l | Wako Chamicals | Guaranteed reagent grade |
| EHSDA | 60 mmol/l | SIGMA |  |
| Bis-tris buffer | 0.25 mmol/l | Nacalaitesque | Specially prepared |

TABLE 4-continued

| Reagent | Reagent concentration | Maker | Reagent purity |
| --- | --- | --- | --- |
| Smectite | 0.3% | Co-op Chemical |  |
| Hydrogen peroxide |  | Santoku Kagaku Kogyo | Guaranteed reagent grade |

As seen from the results of FIG. 1, it could be confirmed that a reaction proceeded under the condition that a dyestuff was adsorbed to smectite like the condition that no smectite was added. The absorption maximum when no smectite was added was about 593 nm and the absorption maximum when smectite was added was about 578 nm.

Example 2

POD, 4-AA, EHSDA and a bis-tris buffer (pH 6.5) were taken into a quartz cell having a cell length of 1 cm to final concentrations shown in Table 3 and incubated at 37° C. for 3 minutes. After the temperature was adjusted, hydrogen peroxide having a concentration shown in Table 5 was added to start a reaction and absorbance was measured 3 minutes after the start of the reaction. This reaction reached a termination completely 3 minutes after the measurement.

The instrument used was the JascoV-550 (Japan Spectroscopic Co. Ltd.), and the measurement wavelength was 593 nm (wavelength near the absorption maximum). A calibration curve of hydrogen peroxide when no smectite was added could be obtained from this result.

TABLE 5

| Concentration of hydrogen peroxide (μmol/l) | Absorbance | | |
| --- | --- | --- | --- |
|  | First time | Second time | Average |
| 200 | 1.70 | 1.70 | 1.70 |
| 100 | 0.85 | 0.85 | 0.85 |
| 50 | 0.42 | 0142 | 0.42 |
| 25 | 0.21 | 0.21 | 0.21 |
| 13 | 0.10 | 0.10 | 0.10 |
| 6.3 | 0.04 | 0.04 | 0.04 |
| 4.2 | 0.01 | 0.01 | 0.01 |
| 1.6 | 0.01 | 0.01 | 0.01 |

Example 3

<Experimental Method>

POD, 4-AA, EHSDA, a bis-tris buffer (pH 6.5) and synthetic smectite were taken into a disposable cell having a cell length of 1 cm (made from polymethyl methacrylate) to final concentrations shown in the above Table 2, and the temperature was adjusted to 37° C. for 180 seconds. After the temperature adjustment, hydrogen peroxide was added to a final concentration shown in Table 6, and absorbance was measured from 10 seconds after the addition of hydrogen peroxide for 1,800 seconds at intervals of 2 seconds. The JascoV-550 (Japan Spectroscopic Co. Ltd.) was used as a measuring device, and the measurement wavelength was 577 nm (wavelength near the maximum absorption wavelength). To measure only an agglomerated portion, a 0.1-ml slit was used. The measurement result at a hydrogen peroxide concentration of 0 μmol/l was made blank, the difference of absorbance (ΔAbs) from the blank at 1,800 seconds after the start of measurement was obtained, and a calibration curve of hydrogen peroxide when smectite was added was obtained.

<Result>

Figure 3:
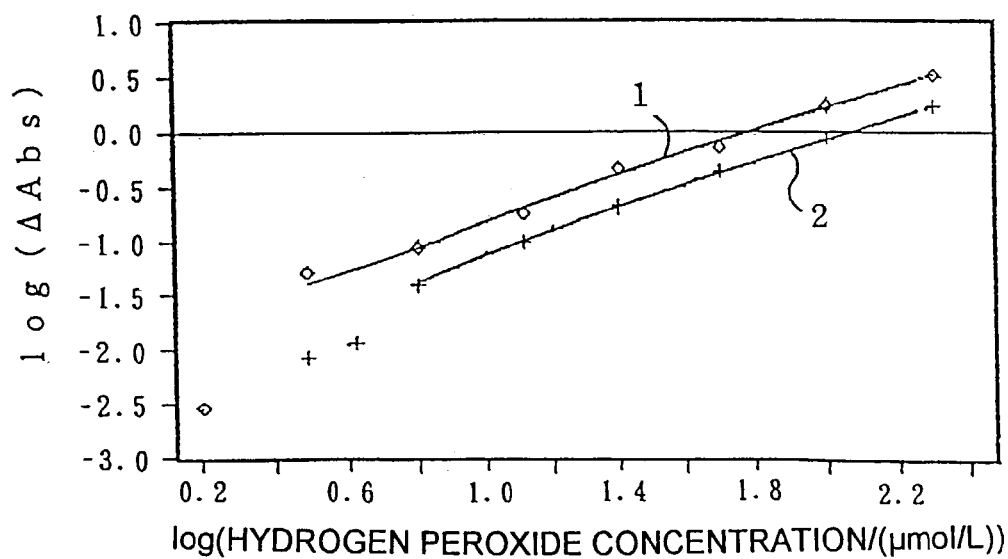
FIG. 3 shows logarithmic representation in both the axis of ordinate and the axis of abscissa of the calibration curves of FIG. 2.

The result is shown in FIG. 2 together with the result when no smectite was added in Example 2. A calibration curve showing the logarithmic representation in both of the axis of ordinates and the axis of abscissa of the calibration curve of FIG. 2 is shown in FIG. 3. It is understood from Tables 5 and 6 and FIGS. 2 and 3 that there is a correlation between absorbance resulted by the adsorped dyestuff and hydrogen peroxide. When smectite was added, a calibration curve of r=0.999 (r=correlation coefficient) was obtained at a hydrogen peroxide concentration of 0 to 200 µmol/l.

It is seen from FIGS. 2 and 3 that when no smectite was added, the minimum detection limit was about 6 µmol/l whereas when smectite was added, the minimum detection limit was improved to 3 µmol/l. The slope of the calibration curve was about 2 times that when no smectite was added.

TABLE 6

| Concentration of hydrogen peroxide (µmol/l) | Absorbance | ΔAbs |
|---|---|---|
| 200 | 3.61 | 3.30 |
| 100 | 2.02 | 1.71 |
| 50 | 1.01 | 0.70 |
| 25 | 0.76 | 0.45 |
| 13 | 0.49 | 0.18 |
| 6.3 | 0.40 | 0.09 |
| 3.1 | 0.36 | 0.05 |
| 1.6 | 0.31 | 0.00 |
| 0 | 0.31 | |

Example 4

<Experimental Method>

POD, 4-AA, EHSDA, a bis-tris buffer (pH 6.5) and synthetic smectite were taken into a disposable cell having a cell length of 1 cm (made from polymethyl methacrylate) to final concentrations shown in the above Table 2, and the temperature was adjusted to 37° C. for 180 seconds. After the temperature adjustment, hydrogen peroxide was added to a final concentration of 100 µmol/l, and absorbance was measured from 20 seconds after the addition of hydrogen peroxide for 600 seconds at intervals of 2 seconds. The JascoV-550 (Japan Spectroscopic Co. Ltd.) was used as a measuring instrument, and the measurement wavelength was 577 nm (wavelength near the maximum absorption wavelength). To measure only an agglomerated portion, a 0.1-ml slit was used. The measurement result at a hydrogen peroxide concentration of 0 µmol/l was made blank.

POD, 4-AA, EHSDA and a bis-tris buffer (pH 6.5) were taken into a disposable cell having a cell length of 1 cm (made from polymethyl methacrylate) to final concentrations shown in the above Table 3, and the temperature was adjusted to 37° C. for 180 seconds. After the temperature adjustment, hydrogen peroxide was added to a final concentration of 100 µmol/l, and absorbance was measured from 20 seconds after the addition of hydrogen peroxide for 600 seconds at intervals of 2 seconds. The JascoV-550 (Japan Spectroscopic Co. Ltd.) was used as a measuring instrument, and the measurement wavelength was 593 nm (wavelength near the maximum absorption wavelength). A 0.1-ml slit was used.

<Results>

Figure 4:
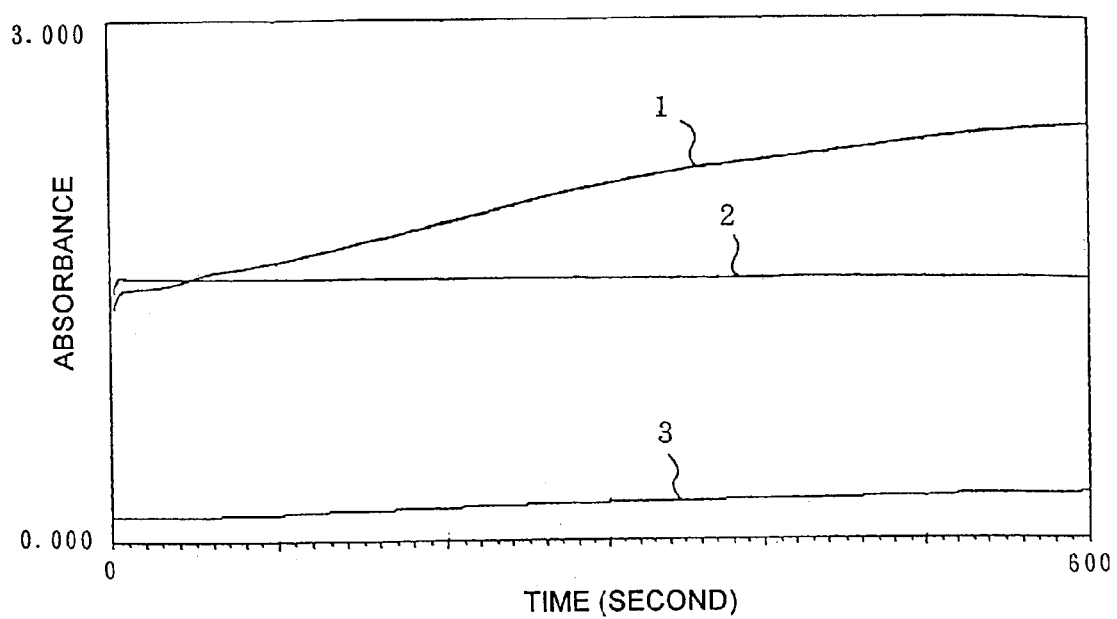
FIG. 4 shows time-cource of absorbance after the addition of hydrogen peroxide in Example 4.

The results are shown in FIG. 4. It is understood from FIG. 4 that the addition of smectite is effective in increasing sensitivity. It is confirmed that a color developing reaction reaches a termination in about 30 seconds after the addition of hydrogen peroxide. Even when smectite was added after color was developed without addition of smectite, the adsorption and agglomeration of a dyestuff were observed.

Example 5

3,3'-(3,3'-Dimethoxy-4,4'-bisphenylene)-bis[2-(p-nitro-phenyl)-5-phenyl-2H-tetrazolium chloride (to be abbreviated as "tetrazolium salt" hereinafter) as a tetrazolium salt, a phosphate buffer (a mixture of disodium hydrogenphosphate and sodium dihydrogenphosphate having a pH of 8.5) as a buffer, L-ascorbic acid and smectite (trade name: Lucentite SWN: synthetic smectite manufactured by Co-op Chemical Co.) were taken into a disposable tube to final concentrations shown in Table 7 and allowed to react with one another to develop color. This reaction is known as a reaction for forming water-insoluble formazan. The obtained color developing solution was diluted 10 times, and the absorption spectrum of the solution was measured at a wavelength of 400 to 800 nm.

For comparison, the tetrazolium salt, the phosphate buffer and L-ascorbic acid were taken into a disposable tube to final concentrations shown in Table 7 as described above without addition of smectite and allowed to react with one another to develop color. The absorption spectrum of the obtained color developing solution was measured at a wavelength of 400 to 800 nm.

Figure 5:
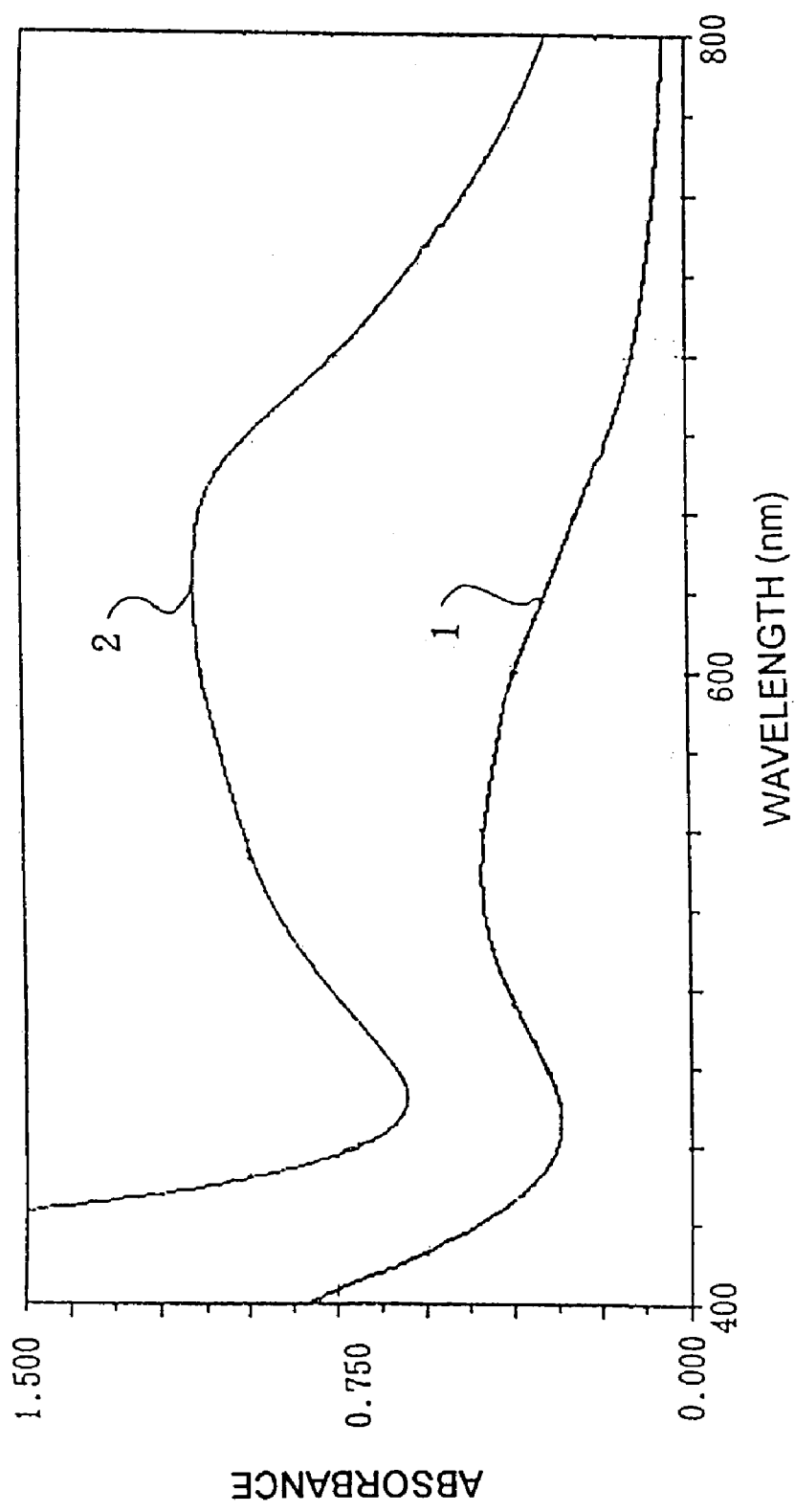
FIG. 5 shows absorption spectra measured in Example 5.

The JascoV-550 spectrophotometer of Japan Spectroscopic Co. Ltd. was used to measure absorbance. A disposable cell (made from polymethyl methacrylate) having a cell length of 1 cm was used. The measurement results are shown in FIG. 5.

TABLE 7

| Reagent | Final concentration |
|---|---|
| Tetrazolium salt | 1 mmol/l |
| Phosphate buffer | 100 mmol/l |
| L(+)-Ascorbic acid | 333 µmol/l |
| Smectite | 0.1% or 0% (total amount of 3 ml) |

Blue was developed, and the absorption maximum wavelength was about 633 nm in the smectite-non-added system. Red purple was developed, and the absorption maximum wavelength was about 535 nm in the smectite-added system. It could be confirmed that a reaction proceeded under the condition that smectite was added like the condition that no smectite was added. Further, a deposit considered as formazan separated out on the inner surface of the cell in the smectite-non-added system whereas neither a precipitate nor an agglomerate was observed in the cell in the smectite-added system. Since the absorption maximum shifts to a short wavelength side, it is understood that when the same color developing reaction system as that of this example is used, it is better to carry out the measurement of absorbance at 633 nm (for the smectite-non-added system) and 535 nm (for the smectite-added system) which are wavelengths near the absorption maximum wavelengths of the smectite-added system and the smectite-non-added system, respectively.

Example 6

The same tetrazolium salt, phosphate buffer (pH 8.5) and smectite as those used in Example 5 were taken into a disposable tube to final concentrations shown in Table 8 and incubated at 30° C. for 3 minutes. After incubation, L-ascorbic acid was added to final concentrations (0 to 333 μmol/l) shown in Table 9 and allowed to react at 30° C. for 30 minutes, and absorbance was measured (measurement wavelength of 535 nm). A sample obtained when ascorbic acid was not added was made blank, and a calibration curve was drawn from the measurement results.

For comparison, the tetrazolium salt and the phosphate buffer were taken into a disposable tube to final concentrations shown in Table 8 in the same manner as described above except that smectite was not added and incubated at 30° C. for 3 minutes. After incubation, ascorbic acid was added to final concentrations (0 to 333 mol/l) shown in Table 10 and allowed to react at 30° C. for 30 minutes, and absorbance was measured (measurement wavelength of 633 nm). A sample obtained when ascorbic acid was not added was made blank, and a calibration curve was drawn from the measurement results.

Figure 6:
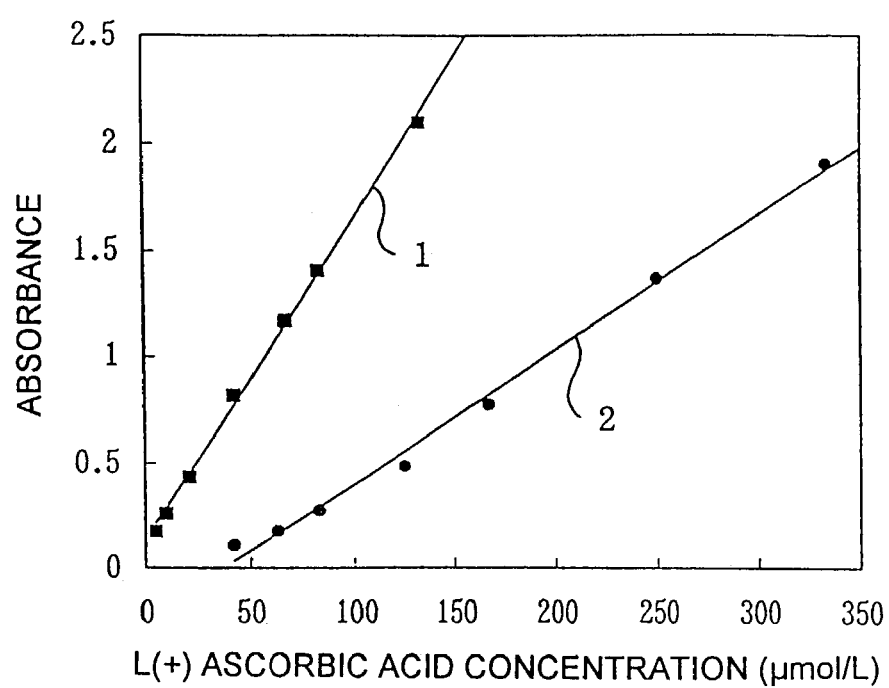
FIG. 6 shows the calibration curves of the concentration of ascorbic acid obtained in Example 6.

FIG. 6 shows the obtained calibration curves. In the smectite-non-added system, a calibration curve of r (correlation coefficient)=0.9972 was obtained at an ascorbic acid final concentration of 41.7 to 333.3 μmol/l. In the smectite-added system, a calibration curve of r=0.9985 was obtained at an ascorbic acid final concentration of 5.2 to 133.3 μmol/l. It is seen that the slope of the obtained calibration curve in the smectite-added system was about 2.5 times that of the smectite-non-added system and that a sensitivity improving effect could be obtained by the addition of smectite. Further, a deposit considered as formazan separated out on the inner surface of the tube in the smectite-non-added system whereas neither a precipitate nor an agglomerate was observed in the tube in the smectite-added system.

The JascoV-550 spectrophotometer of Japan Spectroscopic Co. Ltd. was used to measure absorbance. A disposable cell (made from polymethyl methacrylate) having a cell length of 1 cm was used.

TABLE 8

| Reagent | Final concentration |
| --- | --- |
| Tetrazolium salt | 800 μmol/l |
| Phosphate buffer (pH 8.5) | 100 mmol/l |
| L(+)-Ascorbic acid | 0–333.3 μmol/l |
| Smectite | 0.1% or 0% |
|  | (total amount of 3 ml) |

TABLE 9

Smectite-added system

| Final concentration of ascorbic acid (μmol/l) | Absorbance(Abs) |
| --- | --- |
| 5.2 | 0.174 |
| 10.4 | 0.259 |
| 20.8 | 0.437 |
| 41.7 | 0.818 |
| 66.7 | 1.165 |
| 83.3 | 1.404 |
| 133.3 | 2.097 |

TABLE 10

Smectite-non-added system

| Final concentration of ascorbic acid (μmol/l) | Absorbance(Abs) |
| --- | --- |
| 41.7 | 0.103 |
| 62.5 | 0.178 |
| 83.3 | 0.271 |
| 125.0 | 0.480 |
| 166.7 | 0.773 |
| 250.0 | 1.358 |
| 333.3 | 1.903 |

Example 7

Figure 7:
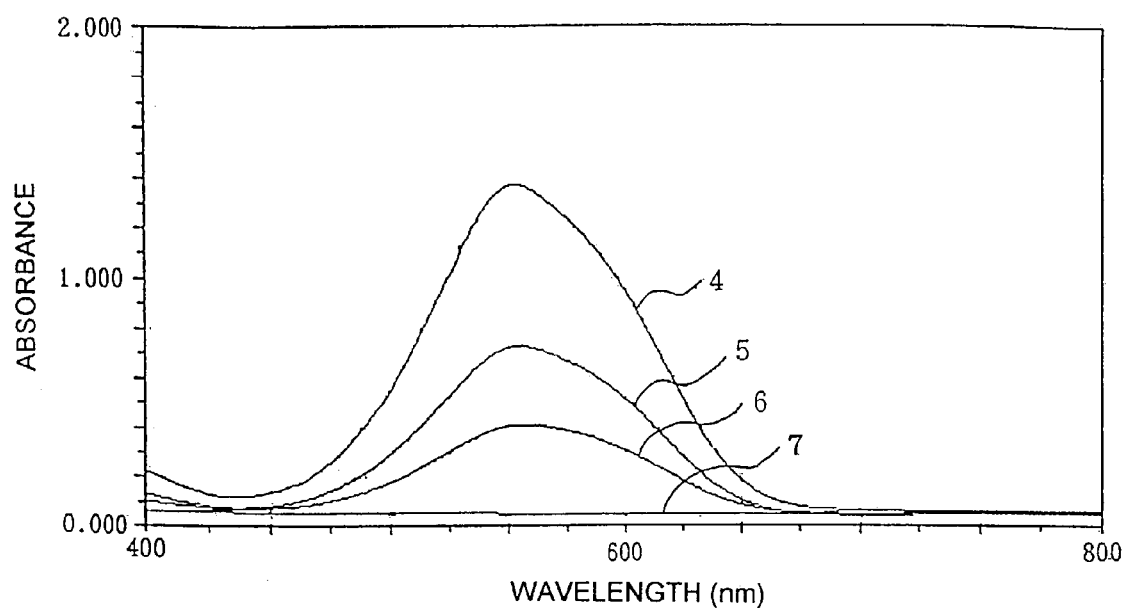
FIG. 7 shows absorption spectra (smectite-added system) measured in Example 7.

Hydrochloric acid, smectite (Lucentite SWN of Co-op Chemical Co.), 2,4-dichloroaniline and sodium nitrite were taken to final concentrations shown in Table 11 in the mentioned order and mixed together, and a Tsuda reagent (N,N-diethyl-N'-1-naphthylnaphthylethylene-diamine oxalate) was added and allowed to react with the mixture. Thus, an azo dyestuff was formed and caused to develop color. The absorption spectrum of this dyestuff was measured at a wavelength of 400 to 800 nm. The sodium nitrite was added in four different concentrations (0, 8, 16 and 33 μmol/l). The results are shown in FIG. 7.

Figure 8:
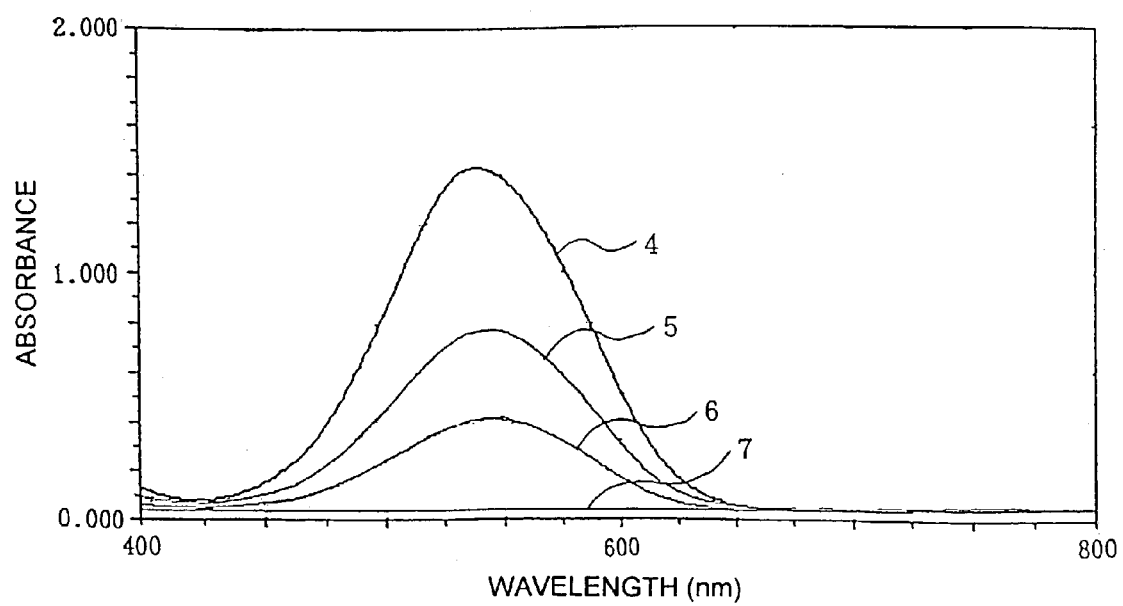
FIG. 8 shows absorption spectra (smectite-non-added system) measured in Example 7.
Figure 9:
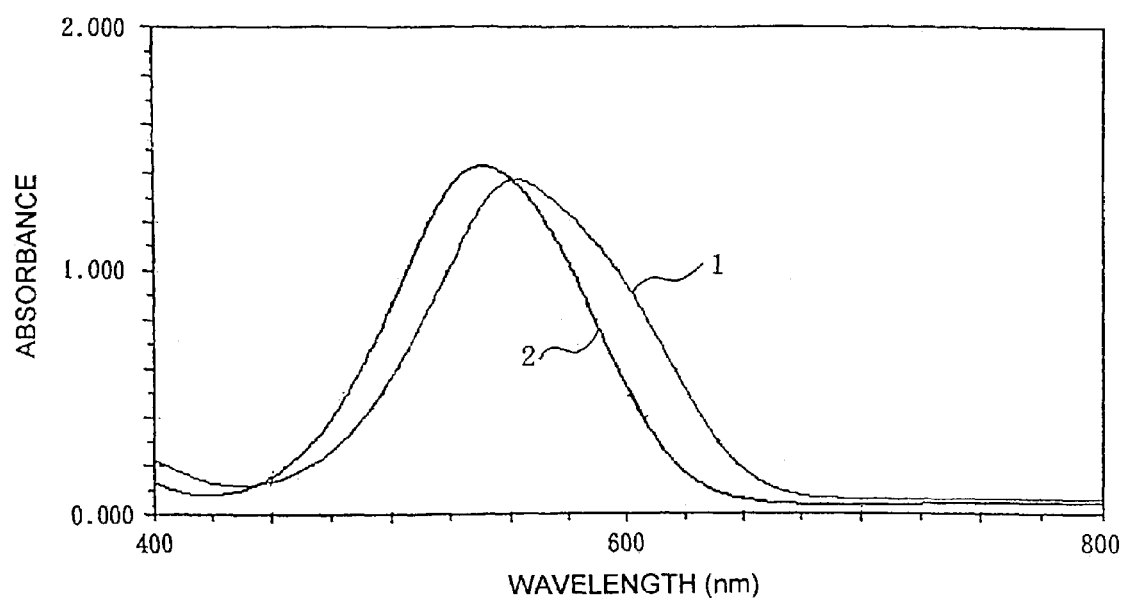
FIG. 9 shows absorption spectra (smectite-added system and non-added system) at a sodium nitrite concentration of 33 µmol/l measured in Example 7.

For comparison, hydrochloric acid, 2,4-dichloroaniline and sodium nitrite were added to final concentrations shown in Table 11 in the same manner as described above except that smectite was not added, and a Tsuda reagent was added to develop color. The absorption spectrum of the resulting mixture was measured at a wavelength of 400 to 800 nm. The sodium nitrite was added in four different concentrations (0, 8, 16 and 33 μmol/l). The results are shown in FIG. 8. The absorption spectra of the smectite-added system and the smectite-non-added system obtained when the concentration of sodium nitrite was 33 μmol/l are shown in FIG. 9. The JascoV-550 spectrophotometer of Japan Spectroscopic Co. Ltd. was used to measure absorbance. A disposable cell (made form polymethyl methacrylate) having a cell length of 1 cm was used.

TABLE 11

| Reagent | Final concentration |
| --- | --- |
| Hydrochloric acid | 1 mol/l |
| 2,4-Dichloroaniline | 200 μmol/l |
| Sodium nitrite | 0–33 μmol/l |
| Tsuda reagent | 200 μmol/l |
| Smectite | 0.1% or 0% |
|  | (total amount of 3 ml) |

In the smectite-non-added system, red purple was developed and the absorption maximum wavelength was about 540 nm. In the smectite-added system, purple was developed and the absorption maximum wavelength was about 555 nm. It could be confirmed that a reaction proceeded under the condition that smectite was added like the condition that no smectite was added. Since the absorption maximum shifts to a long wavelength side, it is understood that when the same color developing reaction system as that of this example is used, it is better to carry out the measurement of absorbance at 540 nm (for the smectite-non-added system) and 555 nm (for the smectite-added system) which are wavelengths near the absorption maximum wavelengths of the smectite-added system and the smectite-non-added system, respectively.

Example 8

The same hydrochloric acid, 2,4-dichloroaniline, sodium nitrite and Tsuda reagent as those used in Example 7 were taken into a disposable cell (made from polymethyl methacrylate) to final concentrations shown in Table 12 and allowed to react with one another at 30° C. for 10 minutes. After color was fully developed, smectite was added to form and precipitate an agglomerate. From 30 seconds after the addition of smectite, the absorbance of the agglomerate was measured for 20 minutes at intervals of 1 second (measurement wavelength of 555 nm). To measure only the absorbance of the agglomerate, a 0.1-ml slit was used. Sodium nitrite was added to final concentrations shown in Table 13 (0 to 50 μmol/l). The result of a sample obtained when the final concentration of sodium nitrite was 0 μmol/l was made blank, and the difference of absorbance from the blank (ΔAbs) 20 minutes after the start of measurement was obtained to draw a calibration curve.

As a smectite-non-added system, hydrochloric acid, 2,4-dichloroaniline and sodium nitrite were taken into a disposable cell to final concentrations shown in Table 12 in the same manner as described above and incubated at 30° C. for 3 minutes. A Tsuda reagent was added, and absorbance was measured from 10 seconds after the addition for 10 minutes at intervals of 1 second (measurement wavelength of 540 nm). Sodium nitrite was added to final concentrations shown in Table 14 (0 to 50 μmol/l). Absorbance 10 minutes after the start of measurement was obtained to draw a calibration curve. The result of a sample obtained when the final concentration of sodium nitrite was 0 μmol/l was made blank. The reaction system used in this experiment reached a termination completely in 10 minutes.

Figure 10:
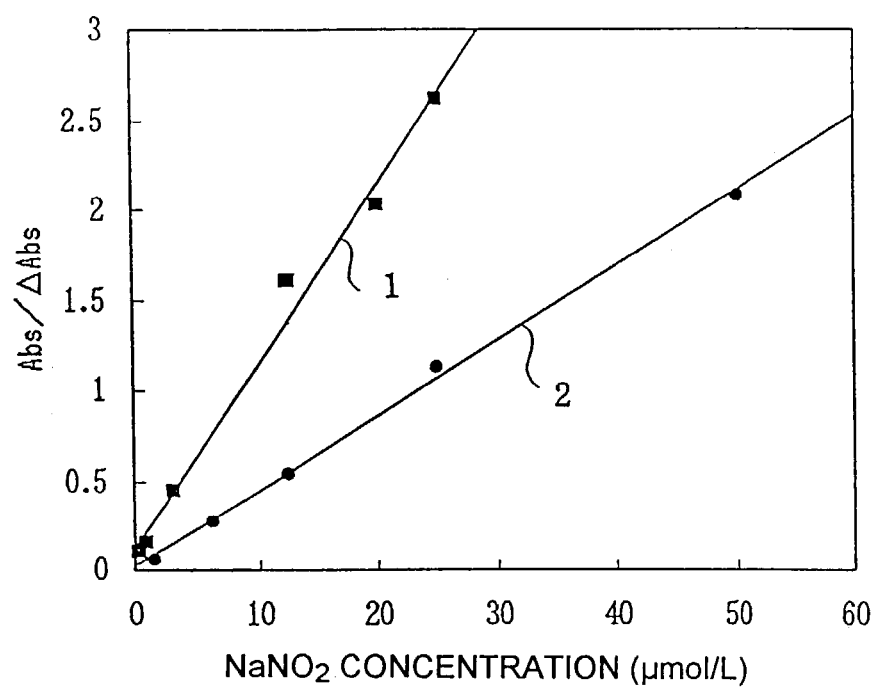
FIG. 10 shows the calibration curves of the concentration of sodium nitrite obtained in Example 8.

FIG. 10 shows the obtained calibration curves. In the smectite-non-added system, a calibration curve of r (correlation coefficient)=0.9991 was obtained at a sodium nitrite final concentration of 1.6 to 50.0 μmol/l. In the smectite-added system, a calibration curve of r=0.9940 was obtained at a sodium nitrite final concentration of 0.4 to 25.0 μmol/l. The inclination of the obtained calibration curve in the smectite-added system was about 2.5 times that of the smectite-non-added system. It is understood that a sensitivity increasing effect can be obtained by the addition of smectite.

The JascoV-550 spectrophotometer of Japan Spectroscopic Co. Ltd. was used to measure absorbance. A disposable cell (made from polymethyl methacrylate) having a cell length of 1 cm was used.

TABLE 12

| Reagent | Final concentration |
| --- | --- |
| Hydrochloric acid | 1 μmol/l |
| 2,4-Dichloroaniline | 200 μmol/l |
| Sodium nitrite | 0–50 μmol/l |
| Tsuda reagent | 200 μmol/l |
| Smectite | 0.1% or 0% |
| | (total amount of 3 ml) |

TABLE 13

Smectite-added system

| Final concentration of sodium nitrite (μmol/l) | Absorbance (ΔAbs) |
| --- | --- |
| 0.4 | 0.099 |
| 0.8 | 0.161 |
| 3.1 | 0.445 |
| 12.5 | 1.610 |
| 20.0 | 2.034 |
| 25.0 | 2.620 |

TABLE 14

Smectite-non-added system

| Final concentration of sodium nitrite (μmol/l) | Absorbance (Abs) |
| --- | --- |
| 1.6 | 0.103 |
| 6.3 | 0.178 |
| 12.5 | 0.271 |
| 25.0 | 0.480 |
| 50.0 | 1.358 |

Example 9

POD, 4-AA and N-ethyl-N-(2-hydroxy-3-sulfopropyl)-3,5-dimethylaniline (to be abbreviated as EHSDMeA hereinafter) as dyestuff precursors, a bis-tris buffer (pH 6.5) as a buffer and smectite as a layered inorganic compound were taken into a disposable cell (made from methacrylate) having a cell length of 1 cm to final concentrations shown in Table 15, and this sample was incubated at 37° C. for 180 seconds. As another sample, the above components excluding smectite were prepared to the same concentrations and incubated likewise.

After temperature adjustment, hydrogen peroxide was added to each of these samples to a final concentration shown in Table 15, and absorbance was measured from 20 seconds after the addition of hydrogen peroxide for 1,800 seconds at intervals of 2 seconds. The JascoV-550 spectrophotometer of Japan Spectroscopic Co. Ltd. was used, and the measurement wavelength was 630 nm. Since an agglomerate was formed when smectite was added, a 0.1-ml slit was used to measure only an agglomerated portion. As a background for the smectite-added system, a sample was prepared by adding smectite to the same concentration without adding hydrogen peroxide, and this reaction solution was measured likewise.

TABLE 15

| Reagent | Final concentration |
| --- | --- |
| POD | 1 U/mL |
| 4-AA*1 | 0.05 mmol/L |
| EHSDMeA*2 | 5 mmol/L |
| Bis-tris buffer*3 | 100 mmol/L |
| Smectite | 0.1% |
| Hydrogen peroxide | 100 mmol/L |
| | (total amount of 3 ml) |

*1) 4-aminoantipyrine (4-amino-1,2-dihydro-1,5-dimethyl-2-phenyl-3H-pyrazol-3-one)
*2) N-ethyl-N-(2-hydroxy-3-sulfopropyl)-3,5-dimethylaniline
*3) bis(2-hydroxyethyl)iminotris(hydroxymethyl)methane
*4) Lucentite SWN (synthetic smectite: manufactured by Co-op Chemical Co.)

The used reagents are shown in Table 16 below.

TABLE 16

| Reagent | Reagent concentration | Maker | Reagent purity |
|---|---|---|---|
| POD | 30 U/mL | Toyobo | |
| 4-AA | 1.5 mmol/L | Wako Chemicals | Guaranteed reagent grade |
| EHSDMeA | 150 mmol/L | Dojin Kagaku | |
| Bis-tris buffer | 0.25 mmol/L | Nacalaitesque | Specially prepared |
| Smectite | 0.3% | Co-op Chemical | |
| Hydrogen peroxide | 300 mmol/L | Santoku Kagaku Kogyo | Guaranteed reagent grade |

Figure 11:
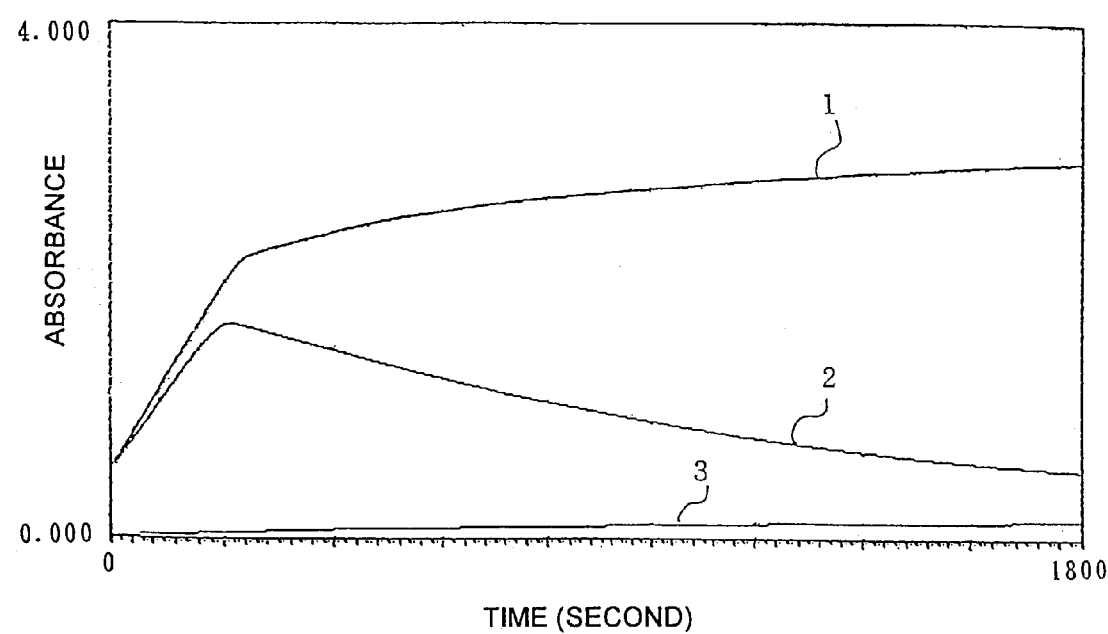
FIG. 11 shows time-cource of absorbance in experiments showing a smectite addition effect in a POD color developing system conducted in Example 9.

The results are shown in FIG. 11. As seen from FIG. 11, a reduction in absorbance was observed about 3 minutes after the start of a reaction in the smectite-non-added system whereas no reduction in absorbance was observed in the smectite-added system. Therefore, it could be confirmed that the detection reaction proceeded when smectite was added like when no smectite was added and further that a dyestuff formed by an oxidation condensation between 4-AA and EHSDMeA was not oxidized and decomposed by hydrogen peroxide and its discoloration was suppressed due to its adsorption to smectite.

Example 10

POD, 4-AA and EHSDMeA, a bis-tris buffer (pH 6.5) and smectite were taken into a disposable cell (made from methacrylate) having a cell length of 1 cm to final concentrations shown in Table 17 and Table 18 to prepare five different samples (Sample Nos. 1 to 5), and each sample was incubated at 37° C. for 180 seconds.

After temperature adjustment, hydrogen peroxide was added to each of these samples in an amount shown in Table 18 to start a reaction. Ascorbic acid was also added in an amount shown in Table 18, 60 seconds after the addition of hydrogen peroxide, and absorbance was measured 20 seconds after the addition for 300 seconds at intervals of 1 seconds. The JascoV-550 spectrophotometer of Japan Spectroscopic Co. Ltd. was used as a measuring device, and the measurement wavelength was 630 nm. A 0.1-ml slit was used to measure only an agglomerated portion.

TABLE 17

| Reagent | Final concentration |
|---|---|
| POD | 1 U/mL |
| 4-AA | 2 mmol/L |
| EHSDMeA | 2 mmol/L |
| Bis-tris buffer | 100 mmol/L |
| Smectite*1 | (see Table 18) |
| Hydrogen peroxide | (see Table 18) |
| L(+)-Ascorbic acid | (see Table 18) |
| | (total amount of 3 ml) |

*1) Lucentite SWN (synthetic smectite manufactured by Co-op Chemical Co.)

TABLE 18

| Sample No. | Smectite (%) | Ascorbic acid (mg/dl) | Hydrogen peroxide (µmol/l) |
|---|---|---|---|
| 1 | 0 | 0 | 100 |
| 2 | 0 | 5 (284 µmol/L) | 100 |
| 3 | 0.1 | 0 | 100 |

TABLE 18-continued

| Sample No. | Smectite (%) | Ascorbic acid (mg/dl) | Hydrogen peroxide (µmol/l) |
|---|---|---|---|
| 4 | 0.1 | 5 (284 µmol/L) | 100 |
| 5 | 0.1 | 0 | 0 |

The used reagents are shown in Table 19 below.

TABLE 19

| Reagent | Reagent concentration | Maker | Reagent purity |
|---|---|---|---|
| POD | 30 U/mL | Toyobo | |
| 4-AA | 60 mmol/L | Wako Chemicals | Guaranteed reagent grade |
| EHSDAMeA | 60 mmol/L | Dojin Kagaku | |
| Bis-tris buffer | 0.25 mmol/L | Nacalaitesque | Specially prepared |
| Smectite | 0.3% | Co-op Chemical | |
| Hydrogen peroxide | 3 mmol/L | Santoku Kagaku Kogyo | Guaranteed reagent grade |
| Ascorbic acid | 150 mg/dl | Nacalaitesque | Guaranteed reagent grade |

Figure 12:
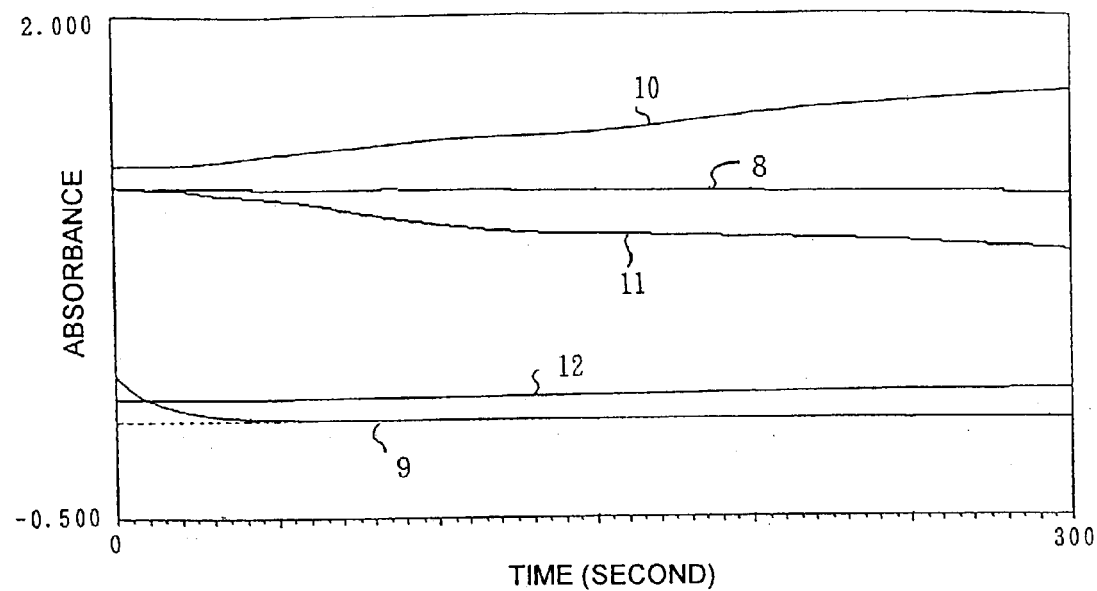
FIG. 12 shows time-cource of absorbance in experiments showing a smectite addition effect in a POD color developing system containing ascorbic acid conducted in Example 10.
Figure 13:
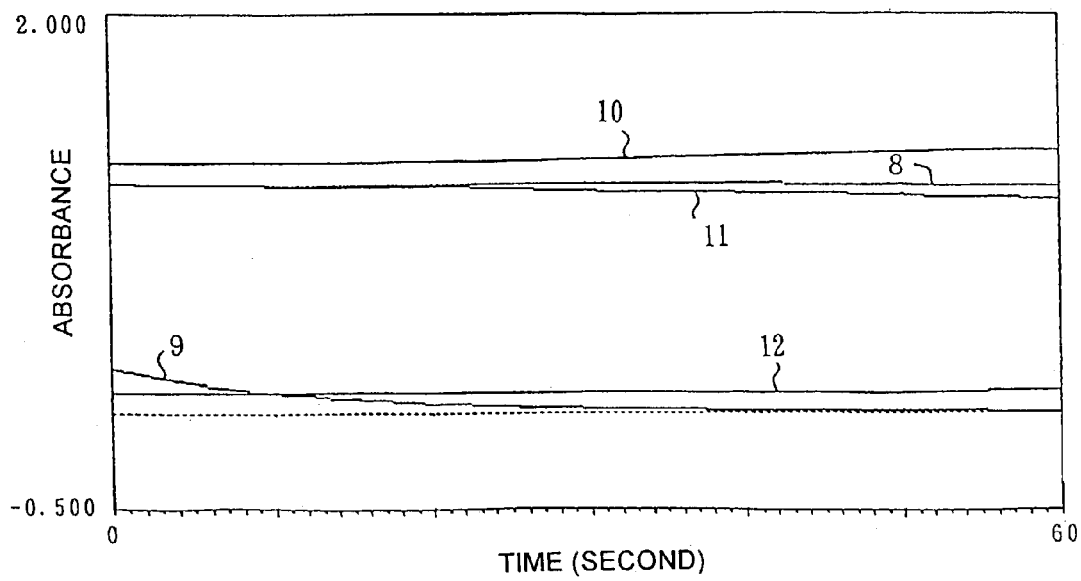
FIG. 13 is an enlarged view of a section for 0 to 60 seconds of FIG. 12.

The results are shown in Table 18 and FIG. 12. FIG. 13 is an enlarged view of a section for 0 to 60 seconds in FIG. 12. Absorbances (Abs) 0, 60 and 300 seconds after the start of measurement are shown in Table 20. Further, to subtract the influence of agglomeration, ΔAbs was obtained for Sample Nos. 3 and 4 from the difference from the absorbance of Sample No. 5. The results are shown as data within parentheses in Table 20.

As seen from FIGS. 12 and 13, in the smectite-non-added system, discoloration occurred immediately after ascorbic acid was added. At the time of the start of measurement (20 seconds after the addition of ascorbic acid), only about 20% of color development when ascorbic acid was not added was seen and the sample became achromatic 60 seconds after the start of measurement (80 seconds after the addition of ascorbic acid).

To contrary, in the smectite-added system, about 90% of color development was seen at the time of the start of measurement (20 seconds after the addition of ascorbic acid), about 80% of color development was seen 60 seconds after the start of measurement (80 seconds after the addition of ascorbic acid), and about 50% of color development was seen 300 seconds after the start of measurement (320 seconds after the addition of ascorbic acid).

It could be confirmed from this result that the reduction and decomposition of a formed dyestuff by ascorbic acid was suppressed by the addition of smectite.

TABLE 20

| Sample No. | 0 second after (ΔAbs) | 60 seconds after (ΔAbs) | 300 seconds after (ΔAbs) |
|---|---|---|---|
| 1 | 1.15 | 1.14 | 1.11 |
| 2 | 0.23 | 0.00 | 0.00 |
| 3 | 1.26(1.16) | 1.33(1.23) | 1.63(1.49) |
| 4 | 1.16(1.06) | 1.07(0.97) | 0.84(0.70) |
| 5 | 0.10 | 0.10 | 0.14 |

Example 11

3,3'-(3,3'-Dimethoxy-4,4'-biphenylene)-bis[2-(p-nitrophenyl)-5-phenyl-2H-tetrazolium]chloride (to be abbreviated as "tetrazolium salt" hereinafter) as a tetrazolium salt, a phosphate buffer (a mixture of disodium hydrogenphosphate and sodium dihydrogenphosphate having a pH of 8.5) as a buffer, L-ascorbic acid and smectite (trade name: Lucentite SWN, synthetic smectite manufactured by Co-op Chemical Co.) were taken into a disposable cell (made from polymethyl methacrylate) to final concentrations shown in Table 21 and incubated at 30° C. for 180 seconds. Thereafter, L-ascorbic acid was added to start a reaction. Absorbance was measured from 10 seconds after addition for 300 seconds at intervals of 1 second to observe time-cource of absorbance. The measurement wavelength was 535 nm, and the reaction temperature was 30° C.

For comparison, the tetrazolium salt and the phosphate buffer were taken into a disposable cell (made from polymethyl methacrylate) to final concentrations shown in Table 21 in the same manner as described above except that smectite was not added and incubated at 30° C. for 180 seconds. Thereafter, L-ascorbic acid was added to start a reaction. Absorbance was measured from 10 seconds after addition for 300 seconds at intervals of 1 second to observe time-cource of absorbance. The measurement wavelength was 633 nm, and the reaction temperature was 30° C.

The JascoV-550 spectrophotometer of Japan Spectroscopic Co. Ltd. was used to measure absorbance, and a disposable cell (made from polymethyl methacrylate) having a cell length of 1 cm was used. Both of the above measurement wavelengths are near the absorption maximum wavelengths. FIG. 14 is a graph showing absorbance with respect to elapsed time. The reaction became stable about 50 seconds after the start of measurement in the smectite-added system whereas the reaction became stable about 300 seconds after the start of measurement in the smectite-non-added system. It is understood from this that the reaction rate is increased by the addition of smectite.

This reaction is known as a reaction for forming water-insoluble formazan. In the smectite-added system, precipitation or agglomeration was not observed in the cell.

TABLE 21

| Reagent | Final concentration |
| --- | --- |
| Tetrazolium salt | 800 µmol/l |
| Phosphate buffer (pH 8.5) | 100 mmol/l |
| L(+)-ascorbic acid | 83.3 µmol/l |
| Smectite | 0.1% or 0% |
|  | (total amount of 3 ml) |

Example 12

Hydrochloric acid, smectite (Lucentite SWN of Co-op Chemical Co.), 2,4-dichloroaniline and sodium nitrite were taken into a disposable cell (made from polymethyl methacrylate) to final concentrations shown in Table 22 and incubated at 30° C. for 180 seconds. The concentration of sodium nitrite was 1.6, 6.3, 12.5, 35.0 and 50.0 µmol/l within the range of 0 to 50 µmol/l.

After incubation, a Tsuda reagent (N,N-diethyl-N'-1-naphthylnaphthylethylenediamine oxalate) was added, and absorbance was measured from 10 seconds after addition for 600 seconds at intervals of 1 second to observe time-cource of absorbance. The measurement wavelength was 555 nm, and the reaction temperature was 30° C.

For comparison, hydrochloric acid, 2,4-dichloroaniline and sodium nitrite were taken into a disposable cell (made from polymethyl methacrylate) to final concentrations shown in Table 22 in the same manner as described above except that smectite was not added and incubated at 30° C. for 180 seconds. Thereafter, a Tsuda reagent was added, and absorbance was measured from 10 seconds after addition for 600 seconds at intervals of 1 second to observe time-cource of absorbance. The measurement wavelength was 540 nm, and the reaction temperature was 30° C.

The JascoV-550 spectrophotometer of Japan Spectroscopic Co. Ltd. was used to measure absorbance, and a disposable cell (made from polymethyl methacrylate) having a cell length of 1 cm was used. Both of the measurement wavelengths are near the absorption maximum wavelengths.

Figure 15:
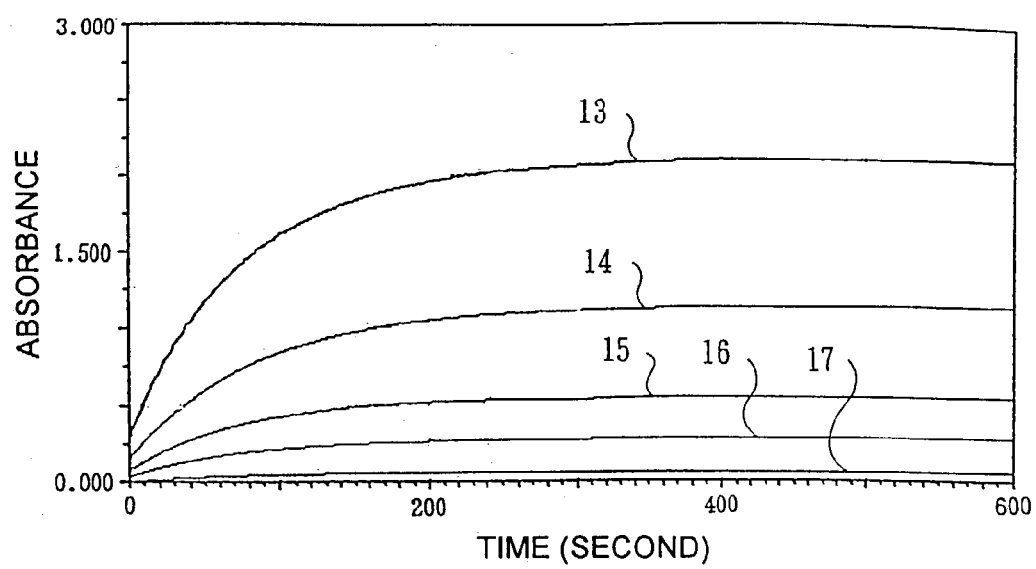
FIG. 15 shows time-cource of absorbance in a smectite-non-added system measured in Example 12.
Figure 16:
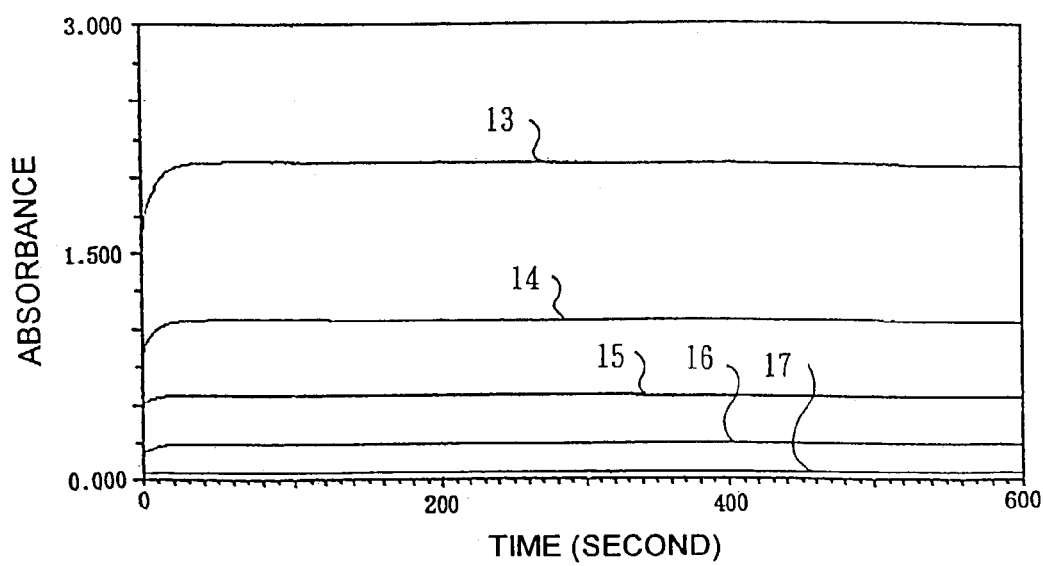
FIG. 16 shows time-cource of absorbance in a smectite-added system measured in Example 12.
Figure 17:
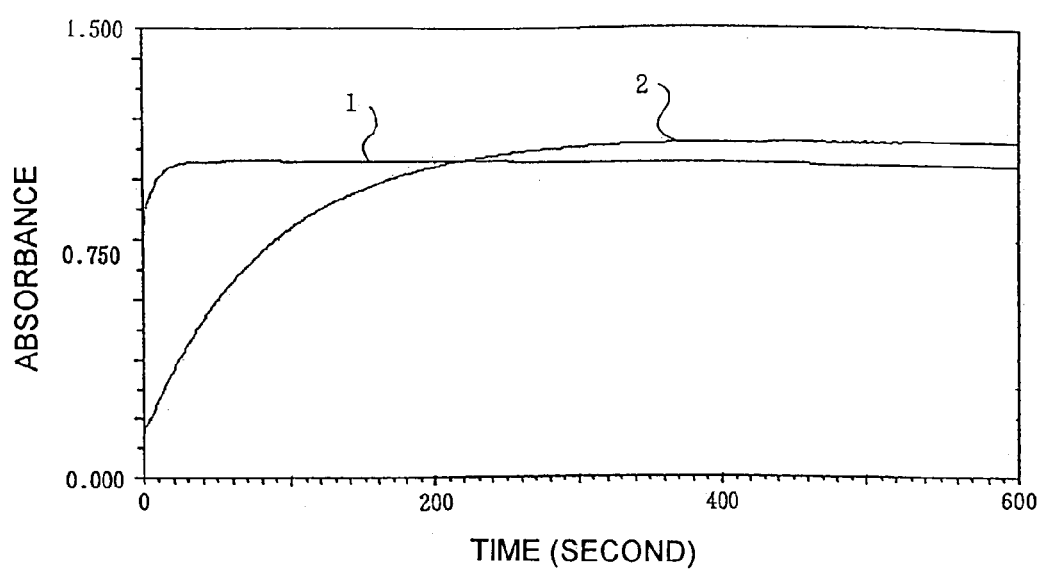
FIG. 17 shows time-cource of absorbance in a smectite-added system and a smectite-non-added system when the concentration of sodium nitrite is 25.0 μmol/l measured in Example 12.

FIGS. 15 to 17 are graphs showing the measurement results of absorbance with respect to elapsed time. Out of these, FIG. 15 is a graph in the smectite-non-added system, FIG. 16 is a graph in the smectite-added system, FIG. 17 is a graph in the smectite-added system and smectite-non-added system when the concentration of sodium nitrite is 25.0 µmol/l. According to these figures, the reaction reaches a termination in about 300 seconds after the start of measurement in the smectite-non-added system whereas the reaction reaches a termination in about 30 seconds after the start of measurement in the smectite-added system. It is understood from this that the reaction rate is increased by the addition of smectite.

TABLE 22

| Reagent | Final concentration |
| --- | --- |
| Hydrochloric acid | 1 mol/l |
| 2,4-Dichloroaniline | 200 µmol/l |
| Sodium nitrite | 0–50 µmol/l |
| Tsuda reagent | 200 µmol/l |
| Smectite | 0.1% or 0% |
|  | (total amount of 3 ml) |

Example 13

POD, 4-AA and N-ethyl-N-(2-hydroxy-3-sulfopropyl)-3,5-dimethoxylaniline (to be abbreviated as EHSDA hereinafter) as dyestuff precursors and a bis-tris buffer (pH 6.5) as a buffer were taken to final concentrations shown in Table 23, and hydrogen peroxide was added to these to obtain a color developing solution. 30 µl of the obtained color developing solution was dropped onto filter paper (No.2 of Toyo Roshi Co.) which was impregnated with a 1% dispersion (solvent: distilled water) of a layered inorganic compound (synthetic smectite: trade name Lucentite SWN of Co-op Chemical Co.) and dried, and untreated filter paper to observe the diffusion of the color developing solution. Assuming that the color developing solution was infiltrated and diffused in a circle, the maximum portion and the minimum portion of the diameter of the circle were measured to obtain the area of a dyestuff-diffused spot from a mean value of these.

TABLE 23

| Reagent | Final concentration |
| --- | --- |
| POD | 1 U/mL |
| 4-AA*1 | 2 mmol/L |
| EHSDA*2 | 2 mmol/L |

TABLE 23-continued

| Reagent | Final concentration |
|---|---|
| Bis-tris buffer solution*3 | 100 mmol/L |
| Hydrogen peroxide | 100 gmol/L (total amount of 3 ml) |

*1) 4-aminoantipyrine(4-amino-1,2-dihydro-1,5-dimethyl-2-phenyl-3H-pyrazol-3-one)
*2) N-ethyl-N-(2-hydroxy-3-sulfopropyl)-3,5-dimethoxyaniline
*3) bis(2-hydroxyethyl)iminotris(hydroxymethyl)methane The used reagents are shown in Table 24 below.

TABLE 24

| Reagent | Reagent concentration | Maker | Reagent purity |
|---|---|---|---|
| POD | 30 U/mL | Toyobo | |
| 4-AA | 60 mmol/L | Wako Chemials | Guaranteed reagent grade |
| EHSDA | 60 mmol/L | SIGMA | |
| Bis-tris buffer | 0.25 mmol/L | Nacalaitesque | Specially prepared |
| Smectite | 1% | Co-op Chemical | |
| Hydrogen peroxide | | Santoku Kagaku Kogyo | Guaranteed reagent grade |

Figure 18:
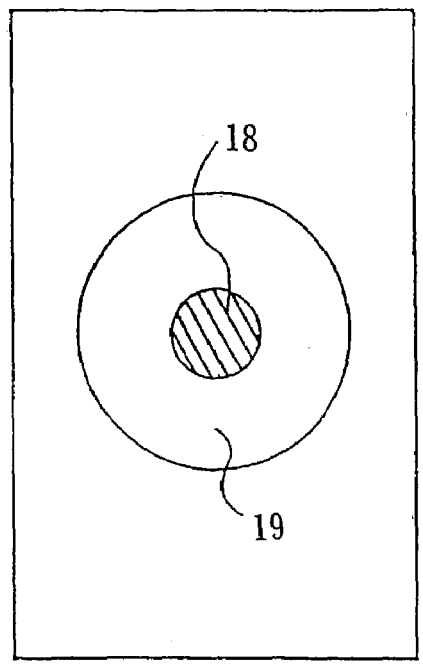
FIG. 18 schematically shows the diffusion state of a dyestuff on smectite-impregnated filter paper in Example 13.
Figure 19:
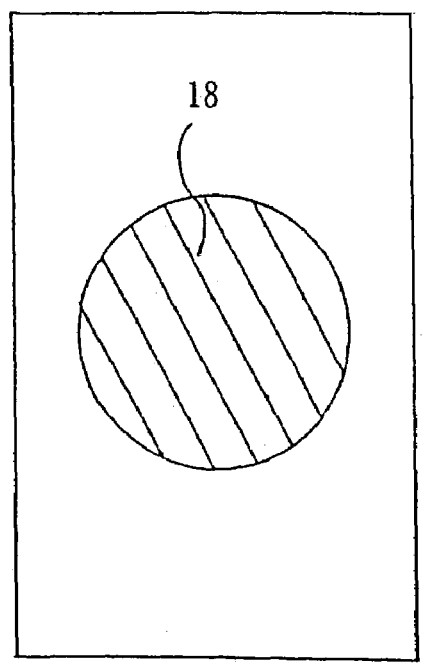
FIG. 19 schematically shows the diffusion state of a dyestuff on untreated filter paper in Example 13.

The obtained diameter, area and color tone of the spot are shown in Table 25. FIG. 18 and FIG. 19 schematically show filter paper in which the color developing solution is diffused.

TABLE 25

| | Diameter (mm) | Area (mm²) | Color |
|---|---|---|---|
| Filter paper impregnated with smectite | 7–8 | 44 | Blue purple |
| Untreated filter paper | 20–22 | 350 | Blue |

In the filter paper impregnated with a dispersion of smectite, the diffusion of a dyestuff was suppressed more and the spot was smaller (about ⅛ in area) compared with the untreated filter paper. However, an achromatic portion devoid of a dyestuff of the color developing solution was diffused to the same extent as that of the untreated filter paper. It was confirmed from this that the dyestuff was selectively adsorbed to smectite contained in the filter paper.

It was observed visually that the color tone of the spot was darker in the filter paper impregnated with smectite than in the untreated filter paper and that the color tone shifted to a short wavelength side. Further, even when the filter paper impregnated with smectite was washed with water, the dyestuff did not elute.

It was found that the dyestuff was adsorbed to the filter paper by the addition of smectite to the filter paper and that the diffusion of the dyestuff was thereby prevented and the elution of the dyestuff was also prevented.

Therefore, it is understood that, when the testing piece of the present invention is used, the formed dyestuff does not move or elute and the accuracy and sensitivity of measurement can be improved. It is also understood that measurement can be carried out with ease because the dyestuff is not moved or concentrated by the drying of the test portion and the formed dyestuff does not elute even if the testing piece is kept immersed in the sample.

Example 14

Urine test paper (multi-item test paper for measuring nitrite, glucose, occult blood, bilirubin and urobilinogen contained in the urine: general test paper available on the market, prepared by forming a test portion by impregnating filter paper with each reagent and affixing the filter paper to a plastic film together with a test portion for calibration) was immersed in control urine prepared by general formulation, pulled up immediately and left to stand for about 30 seconds until coloration was observed, and a piece of the same smectite-impregnated filter paper as used in Example 13 was pressed against the test paper to transfer a dyestuff to the piece of the smectite-impregnated filter paper. The spreading of the dyestuff on the piece of the filter paper was observed visually. The piece of the filter paper was washed well with running water to observe visually whether color came out.

As controls, Toyo Filter Paper No.2 and Toyo Filter Paper No. 131 not treated with smectite were used to carry out the same operation.

The measuring method and formulation in each test are as follows. The results are shown in Table 26 below.

Nitrite Test: Griess Method

4-Aminobenzenearsonic acid was allowed to react with a nitrite under an acidic condition to form a diazonium salt and the diazonium salt was then coupled with N-1-naphthylethylenediamine dihydrochloride to form an azo dyestuff. As for formulation, one sheet of filter paper was impregnated with 0.26 mg of N-1-naphthylethylenediamine dihydrochloride and 0.57 mg of 4-aminobenzenearsonic acid and divided into 100 portions. One of them was made a test portion. One portion absorbed about 6 µl of a solution.

Glucose Test:

Hydrogen peroxide formed by glucose oxidase was allowed to react with a color indicator (tetrabase and guaiac as chromogens) by the catalytic function of peroxidase to develop color by oxidation. As for formulation, one sheet of filter paper was impregnated with 470 IU of glucose oxidase, 219 PU of peroxidase, 13.0 mg of tetrabase and 4.3 mg of guaiac and divided into 100 portions. One of them was made a test portion. One portion absorbed about 6 µl of a solution.

Occult Blood Test:

This is a method making use of the decomposition of cumene hydroperoxide by hemoglobin and the oxidation color development of o-tolidine by the oxygen of a formed active group. The same effect can be expected when a benzidine (such as 3,3',5,5'-tetramethyl-benzidine) is used in place of o-tolidine. As for formulation, one sheet of filter paper was impregnated with 52.6 mg of cumene hydroperoxide and 7.6 mg of o-tolidine and divided into 100 portions. One of them was made a test portion. One portion absorbed about 6 µl of a solution.

Bilirubin Test:

This is a method making use of a reaction in which a diazonium salt was formed from 2-methyl-5-nitroaniline or sulfanilic acid and sodium nitrite as a diazo reagent under an acidic condition and coupled with bilirubin in the presence of dyphylline to form azobilirubin. As for formulation, one sheet of filter paper was impregnated with 3.8 mg of 2-methyl-5-nitroaniline, 2.1 mg of sodium nitrite and a small amount of dyphylline and divided into 100 portions. One of them was made a test portion. One portion absorbed about 6 µl of a solution.

Urobilinogen Test:

This is a method making use of an azo-coupling reaction between urobilinogen and a 3,3'-dimethoxybiphenyl-4,4'-diazonium boron tetrafluoride salt under an acidic condition. As for formulation, one sheet of filter paper was impregnated with 0.36 mg of 3,3'-dimethoxybiphenyl-4,4'-diazonium tetrafluoride borate and divided into 100 portions. One of them was made a test portion. One portion absorbed about 6 μl of a solution.

TABLE 26

| Test | Spreading of dyestuff | | | Coming-out of color by washing | | |
|---|---|---|---|---|---|---|
| | Smectite impregnated | Untreated No. 2 | Untreated No. 131 | Smectite impregnated | Untreated No. 2 | Untreated No. 131 |
| Nitrite test | ○ | X | X | ○ | X | X |
| Glucose test | ○ | X | X | ○ | X | X |
| Occult blood test | ○ | X | X | ○ | X | X |
| Bilirubin test | ○ | X | X | ○ | X | X |
| Urobilinogen test | ○ | X | X | ○ | X | X | spreading of dyestuff ...
○: no spreading,
X: much spreading.
coming-out of color ...
○: color does not come out,
X: color comes out.

As shown by the results of Table 26, a dyestuff was adsorbed to filter paper impregnated with a layered inorganic compound without spreading and color did not come out by washing. Therefore, it is understood that the diffusion of the dyestuff is suppressed and the elution of the dyestuff is prevented in the filter paper impregnated with the layered inorganic compound. Therefore, in the testing piece of the present invention, the formed dyestuff does not move or elute and improvement in the accuracy and sensitivity of measurement can be expected. Since the concentration and movement of the dyestuff by drying the test portion do not occur and the formed dyestuff does not elute while the testing piece is kept immersed in the sample, measurement can be carried out with ease. Further, since the formed dyestuff does not pollute the adjacent test portion in the multi-item testing piece, the interval between adjacent test portions is reduced, thereby making it possible to reduce the size of the testing piece.

When the formed dyestuff was exposed to the air at room temperature without shielding light while the dyestuff was infiltrated into untreated filter paper, color change and discoloration were observed and coloration completely different from that right after a reaction was seen about 1 month later. On the other hand, even when the formed dyestuff adsorbed to filter paper containing a layered inorganic compound was exposed to the air at room temperature without shielding light, color change and discoloration were not observed for at least 3 months.

The above facts show the applicability of the present invention. That is, when the testing piece of the present invention is used, a sample is taken at a patient's home, reaction coloration is caused on the testing piece, and this testing piece is mailed to an examination center at a remote place, the same measurement result as that right after reaction coloration can be obtained. In other words, the testing piece of the present invention is stable in coloration, is free from the concentration of a dyestuff caused by drying and the elution thereof caused by water leakage. Therefore, it can be used as a mailable testing piece.

Example 15

Figure 20:
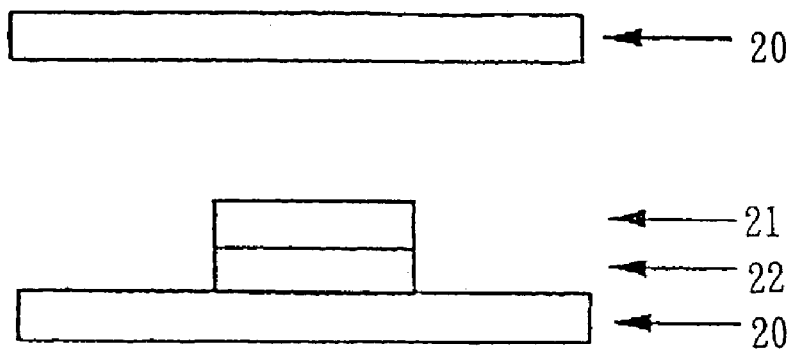
FIG. 20 schematically shows a reaction cell in Example 15.

A solution prepared as shown in Table 27 below was applied to a polyethylene terephthalate (PET) film treated with ultraviolet light by a doctor knife to a film thickness of 100 μm and dried. This coating film was cut into a 1-cm square piece together with the PET film, and the piece was sandwiched between glass plates with 500-μm spacing therebetween as shown in FIG. 20 to prepare a reaction cell. FIG. 20 schematically shows this reaction cell.

2 mmol/l of hydrogen peroxide was added to this reaction cell, and color development at this point was observed. A solution prepared in the same manner as described above except smectite was not added was used to form a reaction cell, and color development was observed.

TABLE 27

| Reagent | Final concentration |
|---|---|
| POD | 1 U/mL |
| 4-AA | 2 mmol/L |
| EHSDA | 2 mmol/L |
| Bis-tris buffer solution | 100 mmol/L |
| Smectite*1 | 0.3% |
| HPC-M*2 | 1% |

*1) Lucentite SWN (synthetic smectite of Co-op Chemical Co.)
*2) hydroxyethylpropyl cellulose The elution of the formed dyestuff from the coating film formed without addition of smectite was observed. On the other hand, when smectite was added, the elution of the formed dyestuff was not observed.

Example 16

An example of formulation of fabricating the testing piece of the present invention having a detection layer composed of a porous structure is shown below. This testing piece is schematically shown in FIG. 21.

Filter paper (2 Chr of Whatman Co.) was immersed in a reagent solution containing GOD (glucose oxidase) and POD as enzymes prepared as shown in Table 28 below and dried at 40° C. for 30 minutes. This filter paper was cut into a 5 mm×5 mm piece which was then bonded to one end of a 5 mm×100 mm white plastic film with adhesive double-coated tape to prepare a testing piece having a test portion composed of the filter paper.

TABLE 28

| Reagent | Final concentration |
|---|---|
| GOD | 100 U/mL |
| POD | 100 U/mL |
| 4-AA | 5 g/L |
| EHSDA | 3 g/L |
| Phosphate buffer solution (pH 7.0) | 0.1 mol/L |
| Smectite | 1% |

In this testing piece, 6 μl of blood plasma was dropped onto the test portion by a pipette, or the testing piece was immersed in the urine collected into a glass, and a reaction was allowed to proceed, and then the intensity of color developed in the detection layer was measured with a reflectometer or the like so that the concentration of glucose contained in the blood plasma or urine can be measured. The porous structure layer containing the layered inorganic compound in the present invention can be used as the detection layer which also serves as the sample suction layer, the reagent layer and the reaction layer in the testing piece of the present invention.

Example 17

Figure 22:
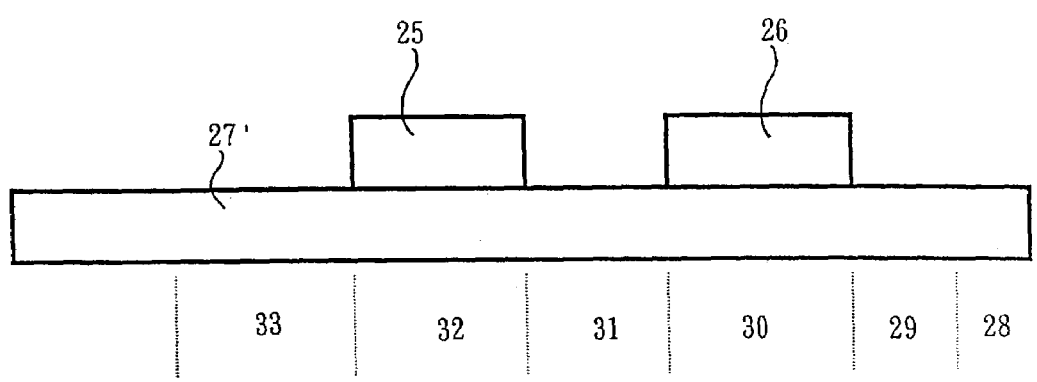
FIG. 22 schematically shows a testing piece in Example 17.

An example of a method for producing the testing piece having a porous structure detection area of the present invention will be described below. FIG. 22 schematically shows this testing piece.

Filter paper (2 Chr of Whatman Co.) was immersed in a reagent solution containing GOD and POD as enzymes prepared as shown in Table 29 below and dried at 40° C. for 30 minutes. This filter paper was cut into a 5 mm×5 mm piece which was then bonded to another 5 mm×100 mm filter paper (2 Chr of Whatman Co.) at a predetermined location (reaction area in FIG. 22) by pressure. Thereafter, another filter paper (2 Chr of Whatman Co.) was immersed in a dispersion of a layered inorganic compound prepared as shown in Table 30 below and dried naturally at room temperature. This filter paper was cut into a 5 mm×5 mm piece which was then bonded to the above 5 mm×100 mm filter paper (2 Chr of Whatman Co.) having a reaction area at a predetermined location (holding area in FIG. 22) by pressure. The thus produced testing piece had a sample suction area, a diffusion area, a reaction area, a holding area for adsorbing a detectable substance and an area for absorbing excess of the sample. The holding area also served as a detection area.

TABLE 29

| Reagent | Final concentration |
|---|---|
| GOD | 100 U/mL |
| POD | 200 U/mL |
| 4-AA | 5 g/L |
| EHSDA | 3 g/L |
| Phosphate buffer solution (pH 7.0) | 0.1 mol/L |

TABLE 30

| Reagent | Final concentration |
|---|---|
| Bis-tris buffer solution (pH 6.5) | 0.1 mol/L |
| Smectite | 1% |

The sample suction area of this testing piece was immersed in the blood plasma collected into a cuvette or the urine collected into a glass. The sample passed through the sample suction area and the diffusion area and reached the reaction area where it was mixed with the reagent to become a reaction solution. After the reaction solution further passed through the reaction time control area and the holding area, the testing piece was pulled up. The intensity of coloration in the holding area was measured with a reflectiometer or the like to measure the concentration of glucose contained in the blood plasma or the urine.

The porous structure containing the layered inorganic compound in the present invention can be used as the detection area which also serves as the holding area for adsorbing a detectable substance (dyestuff) contained in the reaction solution in this example of the testing piece.

INDUSTRIAL APPLICABILITY

The measuring method of the present invention can be used as a method for measuring a substance with high sensitivity and high accuracy. That is, according to the first method of the present invention, high-sensitivity measurement is made possible by measuring a detectable substance after a layered inorganic compound such as a clay mineral is added to a reaction system to adsorbe the detectable substance. According to the second measuring method of the present invention, by adding a layered inorganic compound such as a clay mineral to a reaction system, a detectable substance such as a dyestuff is adsorbed to the layered inorganic compound and protected, whereby the decomposition of the detectable substance by excess of hydrogen peroxide, reducing ascorbic acid or the like can be suppressed and the detectable substance can be stabilized. Therefore, the discoloration or the like can be prevented if a dyestuff is the detectable substance, and stable high-sensitivity and high-accuracy measurement is possible. According to the third method of the present invention, by adding a layered inorganic compound such as a clay mineral to a reaction system which forms a detectable substance, the rate of the formation reaction is increased to enable quick measurement. According to the fourth measuring method of the present invention, by carrying out the formation reaction of a detectable substance by dispersing a layered inorganic compound such as a clay mineral into a reaction solvent, high-sensitivity measurement is made possible even in a reaction system which forms an insoluble substance. According to the testing piece of the present invention, a dyestuff or the like is hardly diffused and eluted, and more sensitive and accurate simple analysis is made possible.

The measuring method of the present invention can be used for the detection, determination or the like of biocomponents contained in the body fluid such as urine and blood, foods, medicines, substances existent in trace amounts in natural environment, industrial chemical substances, substances contained in trace amounts in waste, and the like.

The invention claimed is:

1. A method for measuring an analyte, comprising a step of measuring a detectable substance by using an aqueous reaction system including a formation reaction of the detectable substance based on a chemical reaction of the analyte contained in a sample, wherein a layered inorganic compound is dispersed in the aqueous reaction system to allow the layered inorganic compound to adsorb the detectable substance, thereby increasing measurement sensitivity of the detectable substance.

2. The method according to claim 1, wherein the layered inorganic compound is a 2:1 type clay mineral.

3. The method according to claim 2, wherein the 2:1 type clay mineral is a swelling layered clay mineral.

4. The method according to claim 3, wherein the swelling layered clay mineral is at least one member selected from the group consisting of bentonite, smectite, vermicullite and synthetic fluoro-mica.

5. The method according to claim 4, wherein the smectite is synthetic smectite.

6. The method according to claim 5, wherein the synthetic smectite is at least one member selected from the group consisting of hectorite and saponite.

7. The method according to claim 1, wherein the detectable substance can be detected by an optical method or an electrochemical method.

8. The method according to claim 7, wherein the detectable substance is a dyestuff detectable by an optical method.

9. The method according to claim 8, wherein the dyestuff is an azo compound.

10. The method according to claim 7, wherein the detectable substance is a compound detectable by an electrochemical method and selected from the group consisting of an electron carrier, an electron donor and an electron receptor.

11. The method according to claim 1, wherein the detectable substance is a compound selected from the group consisting of amines, imines, polyenes, aromatic compounds, heterocyclic compounds and complexes between ions and cyclic ligands.

12. The method according to claim 1, wherein the formation reaction of the detectable substance is an oxidation-reduction reaction.

13. The method according to claim 12, wherein the formation reaction of the detectable substance is an oxidation-reduction reaction and the reaction system including the formation reaction of the detectable substance includes a formation reaction of hydrogen peroxide or an oxidation reaction using hydrogen peroxide as an oxidizing agent.

14. The method according to claim 12, wherein the formation reaction of the detectable substance is an oxidation-reduction reaction and the reaction system including the formation reaction of the detectable substance includes the formation reaction of nicotinamide adenine dinucleotide or nicotinamide adenine dinucleotide phosphate or a reaction in which nicotinamide adenine dinucleotide or nicotinamide adenine dinucleotide phosphate acts as a reducing agent.

15. The method according to claim 1, wherein a buffer or a dried product thereof is contained in the reaction system.

16. The method according to claim 1, wherein the layered inorganic compound in the reaction system is added in the form of dispersion to the reaction system.

* * * * *